(12) United States Patent
Shinachi et al.

(10) Patent No.: US 8,062,831 B2
(45) Date of Patent: *Nov. 22, 2011

(54) CARBOXYL-CONTAINING LACTONE COMPOUND, POLYMER, RESIST COMPOSITION, AND PATTERNING PROCESS

(75) Inventors: Satoshi Shinachi, Joetsu (JP); Tsunehiro Nishi, Joetsu (JP); Koji Hasegawa, Joetsu (JP); Takeshi Kinsho, Joetsu (JP); Seiichiro Tachibana, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 64 days.

This patent is subject to a terminal disclaimer.

(21) Appl. No.: 12/434,365

(22) Filed: May 1, 2009

(65) Prior Publication Data

US 2009/0274984 A1 Nov. 5, 2009

(30) Foreign Application Priority Data

May 2, 2008 (JP) ................................. 2008-120465

(51) Int. Cl.
G03F 7/004 (2006.01)
G03F 7/30 (2006.01)
C08F 32/04 (2006.01)

(52) U.S. Cl. ..................... 430/270.1; 430/326; 430/905; 430/910; 526/282

(58) Field of Classification Search .............. 430/270.1, 430/326, 905, 910; 526/282
See application file for complete search history.

(56) References Cited

U.S. PATENT DOCUMENTS

| | | | |
|---|---|---|---|
| 5,650,483 A | 7/1997 | Malik et al. | |
| 6,280,898 B1 | 8/2001 | Hasegawa et al. | |
| 6,312,867 B1 | 11/2001 | Kinsho et al. | |
| 6,329,125 B2 | 12/2001 | Takechi et al. | |
| 6,448,420 B1 | 9/2002 | Kinsho et al. | |
| 6,830,866 B2 | 12/2004 | Kobayashi et al. | |
| 7,833,694 B2 * | 11/2010 | Hasegawa et al. | 430/270.1 |
| 2005/0227174 A1 | 10/2005 | Hatakeyama et al. | |
| 2005/0260525 A1 | 11/2005 | Takemoto et al. | |
| 2007/0128555 A1 | 6/2007 | Harada et al. | |
| 2007/0160929 A1 | 7/2007 | Hasegawa et al. | |
| 2007/0218401 A1 * | 9/2007 | Ando et al. | 430/270.1 |
| 2008/0026331 A1 * | 1/2008 | Hasegawa et al. | 430/327 |
| 2008/0090173 A1 | 4/2008 | Harada et al. | |
| 2009/0023878 A1 | 1/2009 | Maeda et al. | |

FOREIGN PATENT DOCUMENTS

| | | |
|---|---|---|
| JP | 4-39665 A | 2/1992 |
| JP | 9-90637 A | 4/1997 |
| JP | 2000-26446 A | 1/2000 |
| JP | 2000-159758 A | 6/2000 |
| JP | 2000-327633 A | 11/2000 |
| JP | 2000-336121 A | 12/2000 |
| JP | 2001-188346 A | 7/2001 |
| JP | 2002-169289 A | 6/2002 |
| JP | 2003-66612 A | 3/2003 |
| JP | 2005-321765 A | 11/2005 |
| JP | 2005-352466 A | 12/2005 |
| JP | 2007-153982 A | 6/2007 |
| JP | 2007-182488 A | 7/2007 |
| JP | 2007-249192 A | 9/2007 |
| JP | 2008-31298 A | 2/2008 |
| JP | 2008-43501 A | 2/2008 |
| JP | 2008-88343 A | 4/2008 |
| WO | WO 2009/107327 A1 | 9/2009 |

OTHER PUBLICATIONS

Office Action dated Jun. 16, 2010 for Japanese Application No. 2008-064337.
Arimitsu et al., "Sensitivity Enhancement of Chemical-Amplification-Type Photoimaging Materials by Acetoacetic Acid Derivatives", Journal of Photopolymer Science and Technology, vol. 8, No. 1, 1995, pp. 43-44. Arimitsu et al., "Effect of Phenolic Hydroxyl Residues on the Improvement of Acid-Proliferation-Type Phoyoimaging Materials", Journal of Photopolymer Science and Technology, vol. 9, No. 1, 1996, pp. 29-30.
Kudo et al, "Enhancement of the Senesitivity of Chemical-Amplification-Type Photoimaging Materials by β-Tosyloxyketone Acetals", Journal of Photopolymer Science and Technology, vol. 8, No. 1, (1995), pp. 45-46.
Office Action dated Jul. 21, 2010 for Japanese Application No. 2008-120465.

* cited by examiner

*Primary Examiner* — John Chu
(74) *Attorney, Agent, or Firm* — Birch, Stewart, Kolasch & Birch, LLP

(57) ABSTRACT

Carboxyl-containing lactone compounds having formula (1) are novel wherein $R^1$ is H, F, methyl or trifluoromethyl, $R^2$ and $R^3$ are H or monovalent hydrocarbon groups, or $R^2$ and $R^3$ may together form an aliphatic ring, W is $CH_2$, O or S, $k^1$ is an integer of 0 to 4, and $k^2$ is 0 or 1. They are useful as monomers to produce polymers which are transparent to radiation ≦500 nm. Radiation-sensitive resist compositions comprising the polymers as base resin exhibit excellent properties including resolution, LER, pattern density dependency and exposure margin.

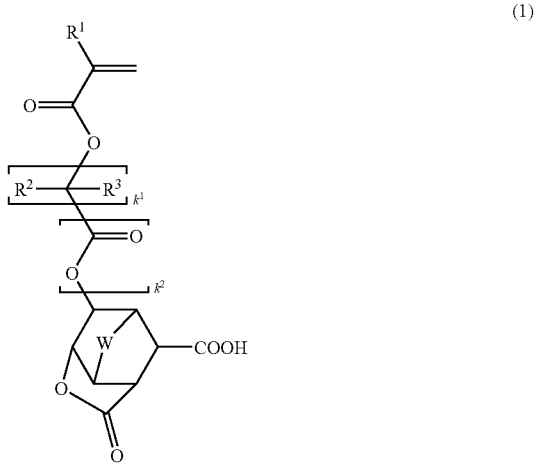

(1)

6 Claims, No Drawings

CARBOXYL-CONTAINING LACTONE COMPOUND, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2008-120465 filed in Japan on May 2, 2008, the entire contents of which are hereby incorporated by reference.

This application is related to the co-pending and commonly-assigned patent applications, U.S. Ser. No. 11/878,759 (US 20080026331 A1, JP-A 2008-031298, inventors: Hasegawa, Nishi, Kinsho, and Tachibana) and U.S. Ser. No. 12/403,317 (JP Appln. 2008-064337, inventors: Hasegawa, Shinachi, Kobayashi, Nishi, and Kinsho).

TECHNICAL FIELD

This invention relates to (1) novel lactone compounds useful as raw materials for the synthesis of functional materials, pharmaceutical and agricultural chemicals, (2) polymers comprising recurring units derived from the lactone compounds, (3) resist compositions comprising the polymers, and (4) a patterning process using the resist compositions.

BACKGROUND ART

The recent drive for higher integration and operating speeds in LSI devices makes it necessary to further reduce the pattern rule. Deep-ultraviolet lithography was developed as an essential technology for micropatterning to a feature size of 0.3 µm or less. Among others, the KrF excimer laser lithography has been fully recognized as a commercial scale production technology.

With respect to chemically amplified resist compositions adapted for the photolithography using ArF excimer laser light of 193 nm wavelength as a light source, the primary requirement is, of course, a high transparency at that wavelength. They are also required to meet a high etch resistance sufficient to comply with film thickness reduction, a high sensitivity sufficient to minimize the burden to expensive optical materials, and among others, a high resolution sufficient to form an exact fine pattern. The key toward these requirements is to develop a base resin featuring high transparency, high rigidity and high reactivity. Active efforts have been devoted for such development.

Typical resins known to be highly transparent to ArF excimer laser light are copolymers of acrylic or methacrylic acid derivatives as disclosed in JP-A 4-39665.

One of the (meth)acrylic resins proposed thus far is a combination of (meth)acrylic units having methyladamantane ester as acid labile group units with (meth)acrylic units having lactone ring ester as adhesive group units as disclosed in JP-A 9-90637. Acid labile groups of exo form are described in U.S. Pat. No. 6,448,420 (JP-A 2000-327633). These groups have so high an acid elimination ability and require a low level of activation energy for acid elimination, affording a high resolution and low dependence on post-exposure bake (PEB). Norbornane lactone is also proposed as an adhesive group having enhanced etching resistance as disclosed in JP-A 2000-26446 and JP-A 2000-159758. These studies have achieved significant improvements in the resolution of ArF resists.

However, in an attempt to form a fine pattern having a pitch of less than 200 nm, prior art resist materials are difficult to form patterns and the patterns, if formed, have insufficient rectangularity and substantial roughness on their surface and sidewalls, and are hardly believed to clear the practically acceptable level. Of the problems associated with prior art resist materials, the most serious problem is the unevenness of fine line size, which is generally referred to as "line edge roughness" (LER). Since the LER has a substantial impact on the performance of semiconductor devices being fabricated, it is strongly desired to overcome this problem. Introducing many acid labile units is advantageous for achieving a higher sensitivity and higher contrast, but entails an enlargement of LER. An approach of reducing the amount of acid labile groups introduced and instead, introducing carboxylic acid units such as (meth)acrylic acid is successful in reducing LER to a certain extent while maintaining a resolution. The introduction of carboxylic acid units, however, gives rise to a new problem of surface roughening due to swelling. This approach does not lead to an essential reduction of LER.

CITATION LIST

Patent Document 1: JP-A H4-39665

Patent Document 2: JP-A H9-90637

Patent Document 3: U.S. Pat. No. 6,448,420 (JP-A 2000-327633)

Patent Document 4: JP-A 2000-26446

Patent Document 5: JP-A 2000-159758

SUMMARY OF THE INVENTION

An object of the present invention is to provide carboxyl-containing lactone compounds useful as monomers for the synthesis of polymers, polymers comprising recurring units derived from the carboxyl-containing lactone compounds, and resist compositions comprising the polymers, the resist compositions exhibiting a high resolution and minimized pattern edge roughness when processed by photolithography using high-energy radiation such as ArF excimer laser radiation as a light source. Another object is to provide a patterning process using the resist compositions.

The inventors have found that a carboxyl-containing lactone compound of the general formula (1) shown below can be readily prepared in high yields, and that a resist composition comprising a polymer derived from the lactone compound as a base resin exhibits satisfactory properties including exposure dose dependency and pattern density dependency as well as minimized pattern edge roughness due to controlled swell when processed by photolithography. Thus the polymer is advantageously used in resist form for precise micropatterning.

Accordingly, the present invention provides a carboxyl-containing lactone compound, polymer, resist composition, and patterning process, as defined below.

In a first aspect, the invention provides a carboxyl-containing lactone compound having the general formula (1).

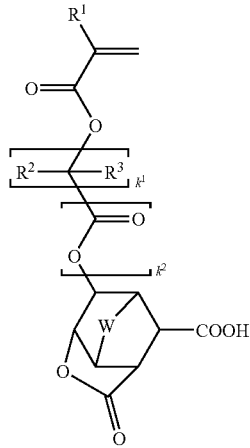
(1)

Herein $R^1$ is hydrogen, fluorine, methyl or trifluoromethyl, $R^2$ and $R^3$ are each independently hydrogen or a straight, branched or cyclic monovalent $C_1$-$C_{10}$ hydrocarbon group, or $R^2$ and $R^3$ may bond together to form an aliphatic hydrocarbon ring with the carbon atom to which they are attached, W is —$CH_2$—, —S— or —O—, $k^1$ is an integer of 0 to 4, and $k^2$ is 0 or 1.

In a second aspect, the invention provides a polymer comprising recurring units having the general formula (2).

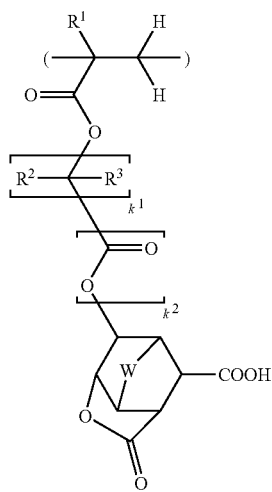
(2)

Herein $R^1$, $R^2$, $R^3$, W, $k^1$, and $k^2$ are as defined above.

The polymer may further comprise recurring units of at least one type selected from the general formulas (3) to (6).

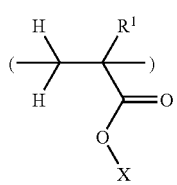
(3)

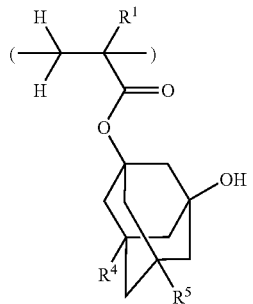
(4)

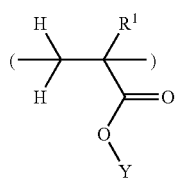
(5)

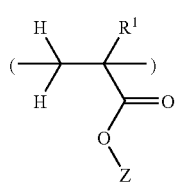
(6)

Herein $R^1$ is as defined above, $R^4$ and $R^5$ are each independently hydrogen or hydroxyl, X is an acid labile group, Y is a substituent group having a lactone structure, and Z is hydrogen, a $C_1$-$C_{15}$ fluoroalkyl group or a $C_1$-$C_{15}$ fluoroalcohol-containing substituent group.

In a third aspect, the invention provides a resist composition comprising the polymer defined above as a base resin.

In a fourth aspect, the invention provides a process for forming a pattern comprising the steps of applying the resist composition defined above onto a substrate to form a resist coating, heat treating the resist coating, exposing the resist coating to high-energy radiation or electron beam through a photomask, optionally heat treating the exposed coating, and developing it with a developer. In a preferred embodiment of the process, the exposing step is performed by immersion lithography including holding a liquid having a refractive index of at least 1.0 between the resist coating and a projection lens. In another preferred embodiment of the process, the process further includes forming a protective film on the resist coating, and the exposing step is performed by immersion lithography including holding a liquid having a refractive index of at least 1.0 between the protective film and a projection lens.

ADVANTAGEOUS EFFECTS OF INVENTION

The carboxyl-containing lactone compounds of the invention are useful as raw materials for the synthesis of functional materials, pharmaceutical and agricultural chemicals. They are most useful as monomers to produce polymers for the manufacture of radiation-sensitive resist compositions which have high transparency to radiation having a wavelength of up to 500 nm, especially up to 300 nm, and exhibit good development properties. Radiation-sensitive resist compositions comprising the polymers as base resin exhibit high resolution and are improved in pattern edge roughness, pattern density dependency (or optical proximity effect) and exposure margin when processed by photolithography. The polymers are advantageously used in resist form for precise micropatterning.

DESCRIPTION OF THE PREFERRED EMBODIMENT

The singular forms "a," "an" and "the" include plural referents unless the context clearly dictates otherwise. The notation (Cn-Cm) means a group containing from n to m carbon atoms per group. In structural formulae, the broken line indicates a valence bond.

It is understood that for many structures represented by chemical formulae, there can exist enantiomers and diastereomers. Unless otherwise stated, a single formula collectively represents all such stereoisomers. The stereoisomers may be used alone or in admixture.

Lactone Compound

The carboxyl-containing lactone compounds of the invention have the general formula (1).

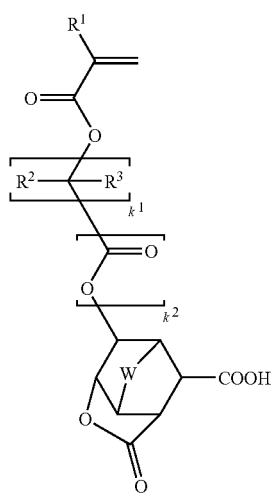

Herein $R^1$ is a hydrogen atom, fluorine atom, methyl group or trifluoromethyl group. $R^2$ and $R^3$ are each independently a hydrogen atom or a straight, branched or cyclic monovalent hydrocarbon group of 1 to 10 carbon atoms, or $R^2$ and $R^3$ may bond together to form an aliphatic hydrocarbon ring with the carbon atom to which they are attached. W is —$CH_2$—, —S— or —O—. The subscript $k^1$ is an integer of 0 to 4, and $k^2$ is equal to 0 or 1.

$R^2$ and $R^3$ may be the same or different. $R^2$ and $R^3$ denote hydrogen or straight, branched or cyclic monovalent $C_1$-$C_{10}$ hydrocarbon groups, typically alkyl groups such as methyl, ethyl, n-propyl, isopropyl, n-butyl, sec-butyl, isobutyl, tert-butyl, cyclopentyl, cyclohexyl, 2-ethylhexyl, and n-octyl. The aliphatic hydrocarbon rings that $R^2$ and $R^3$ together form with the carbon atom to which they are attached are preferably those of 3 to 20 carbon atoms, more preferably 4 to 15 carbon atoms, and examples include cyclopropane, cyclobutane, cyclopentane, cyclohexane, bicyclo[2.2.1]heptane, bicyclo[2.2.2]octane, bicyclo[3.3.1]nonane, bicyclo[4.4.0]decane, and adamantane.

Illustrative examples of the compound having formula (1) are given below.

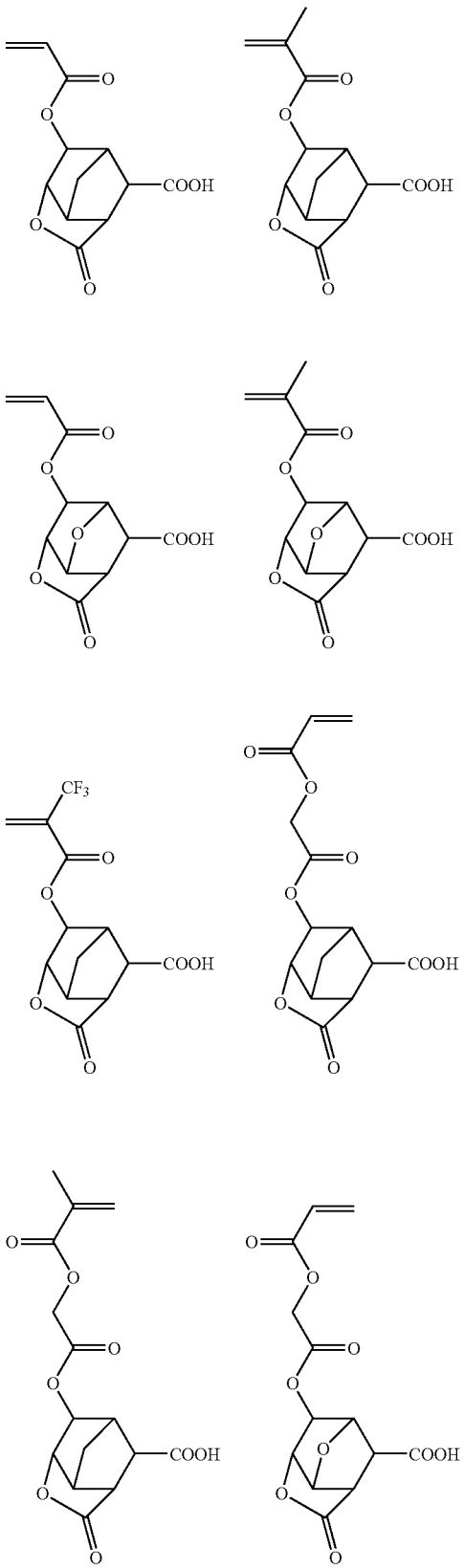

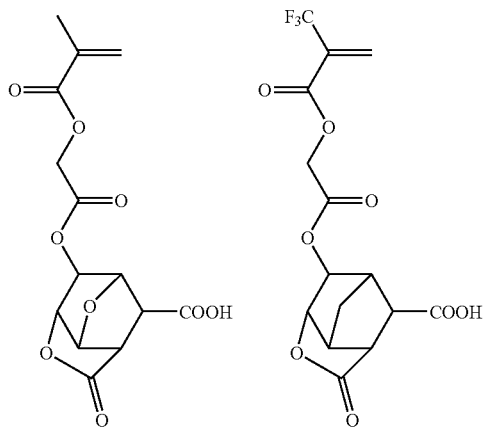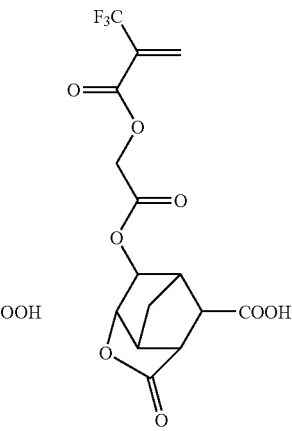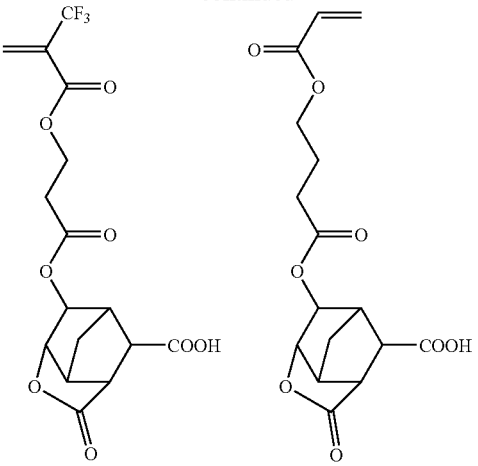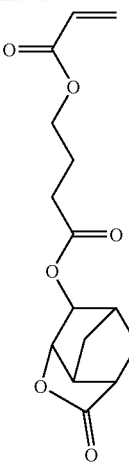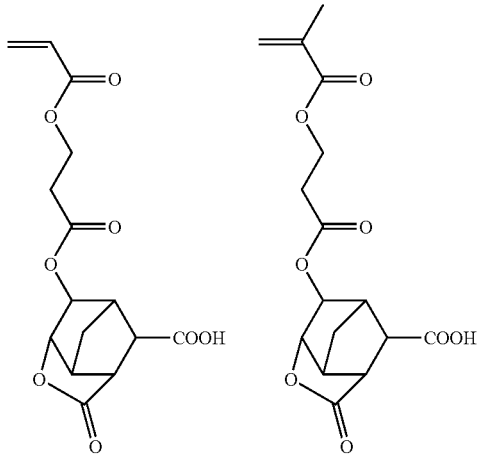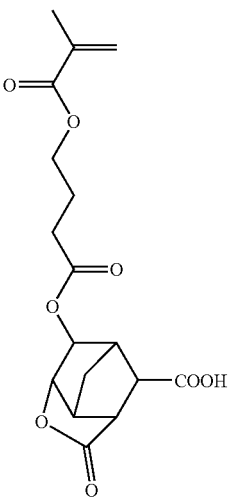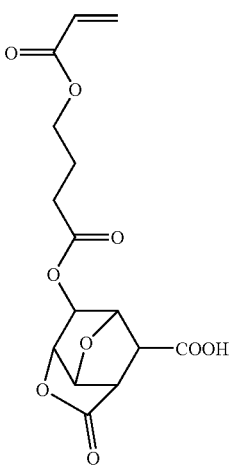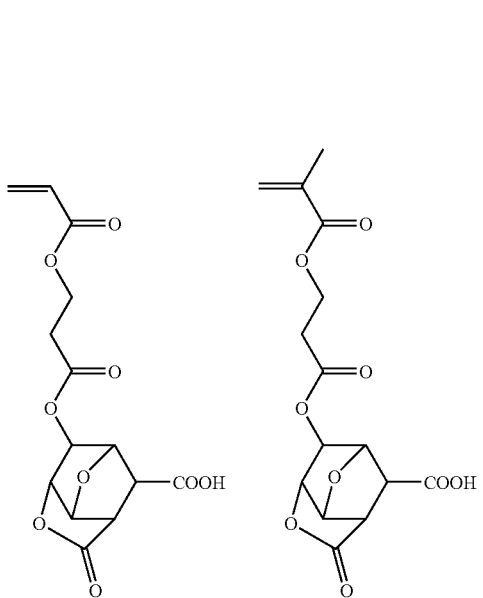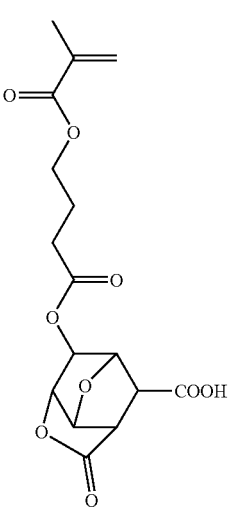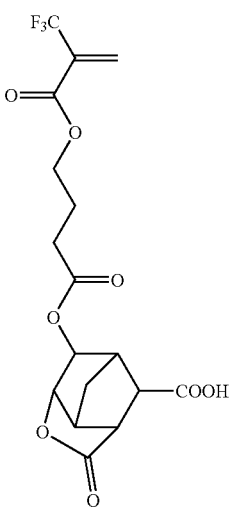

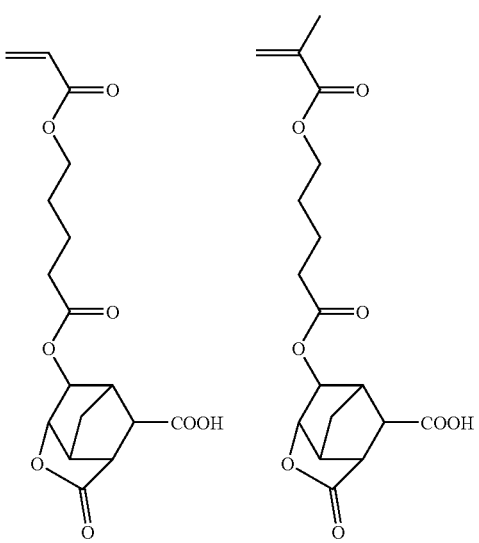
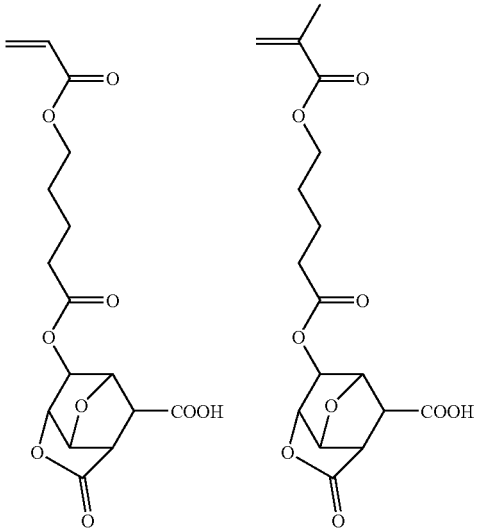
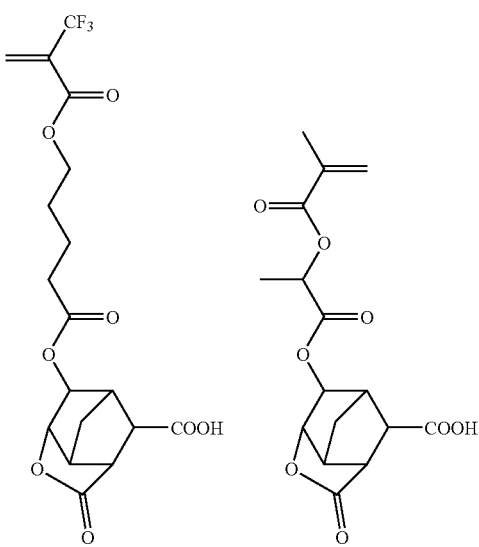
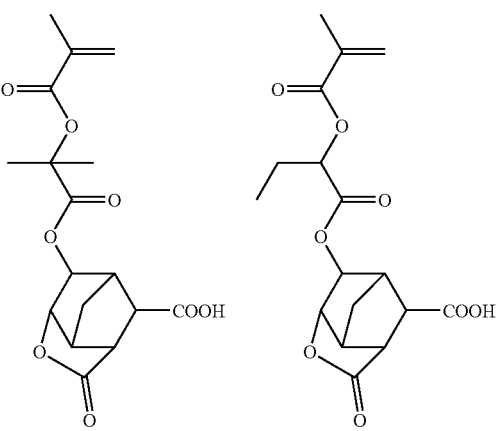
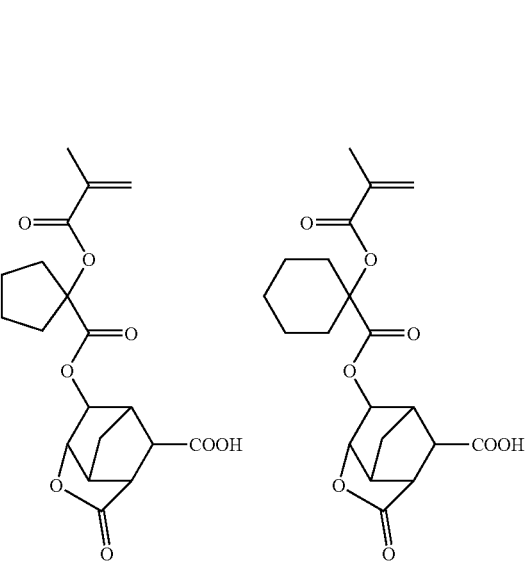
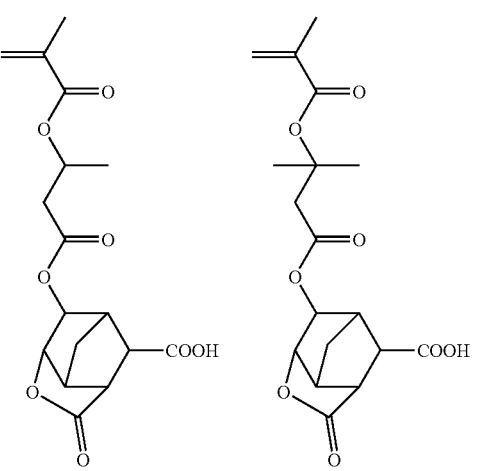

11
-continued
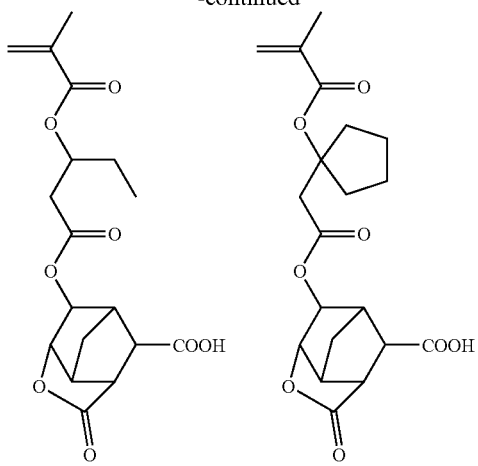
12
-continued
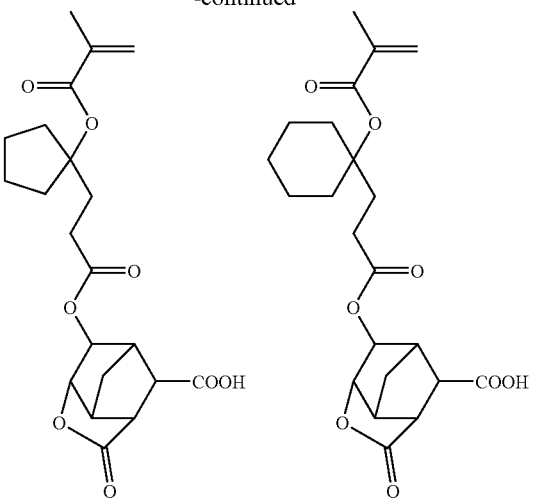
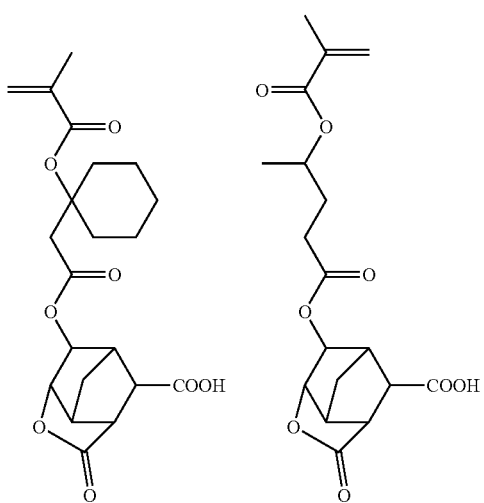
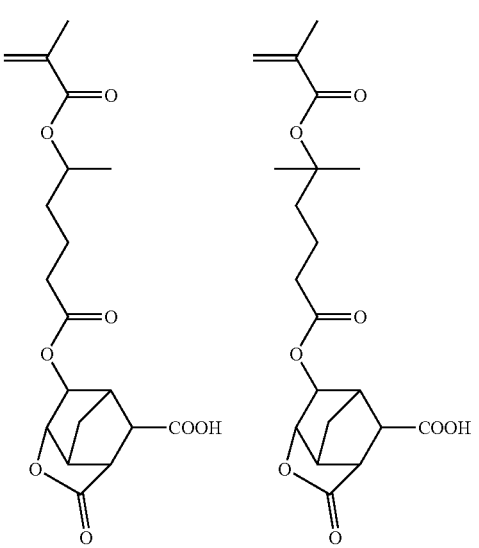
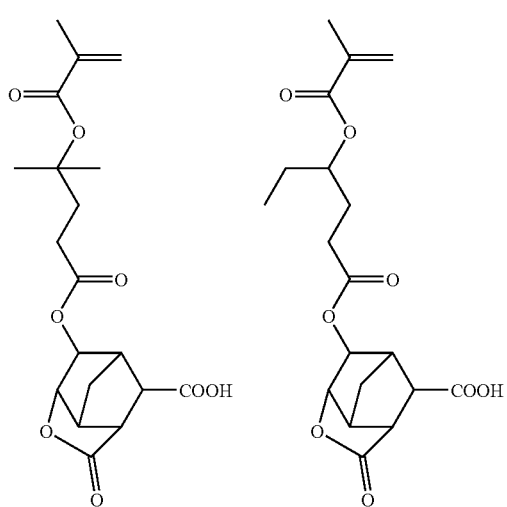
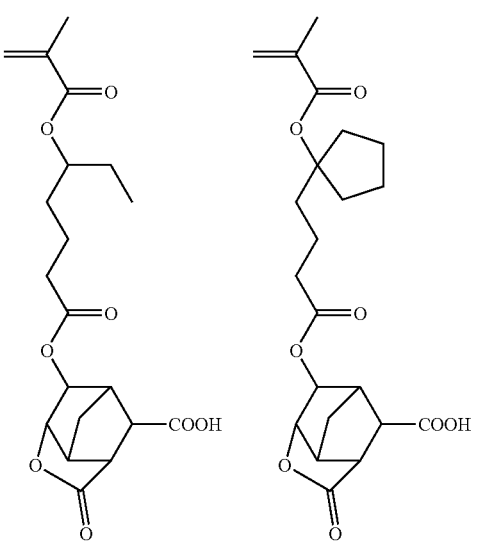

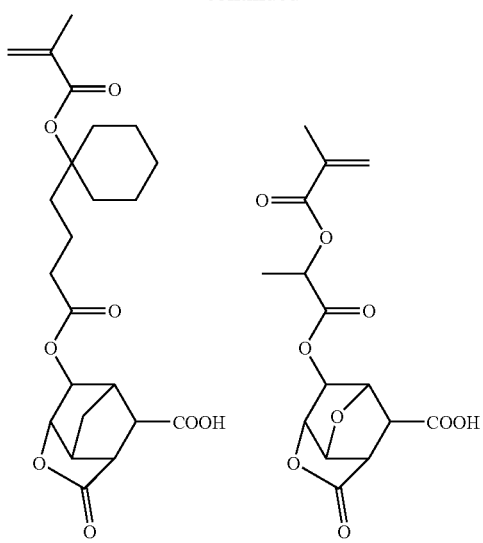
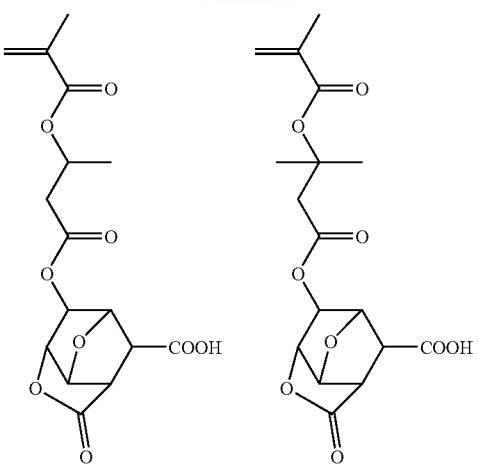
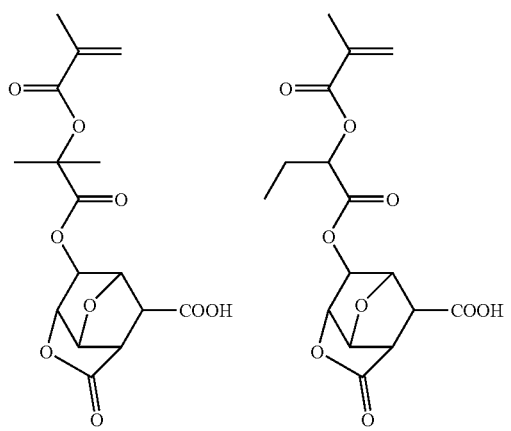
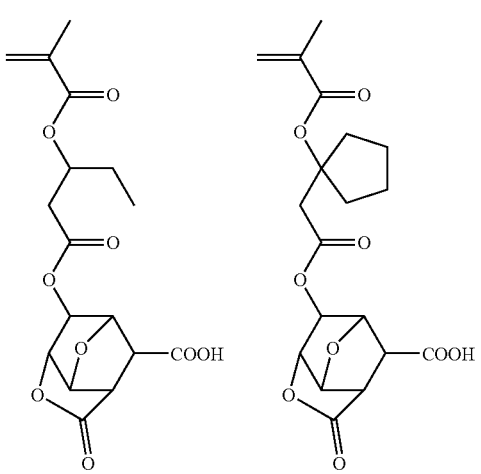
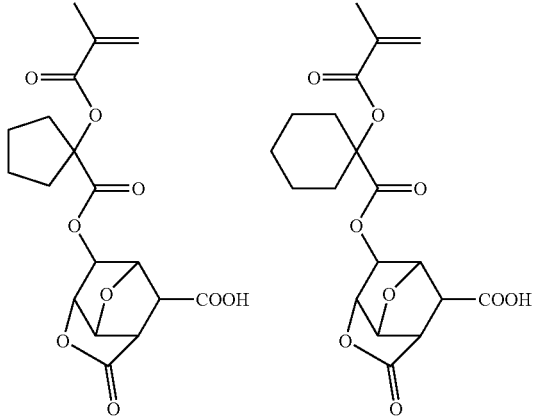
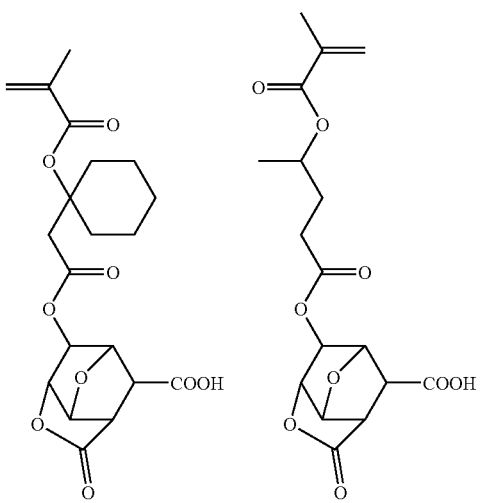

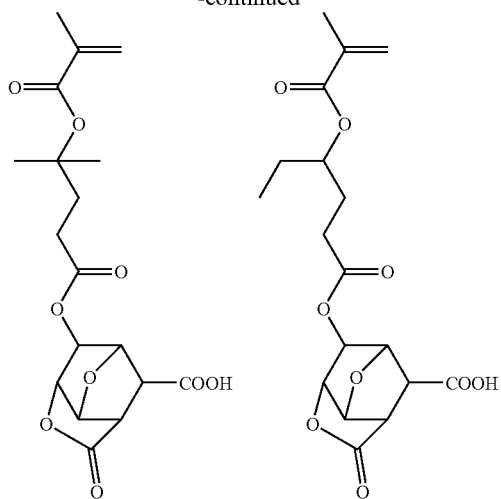
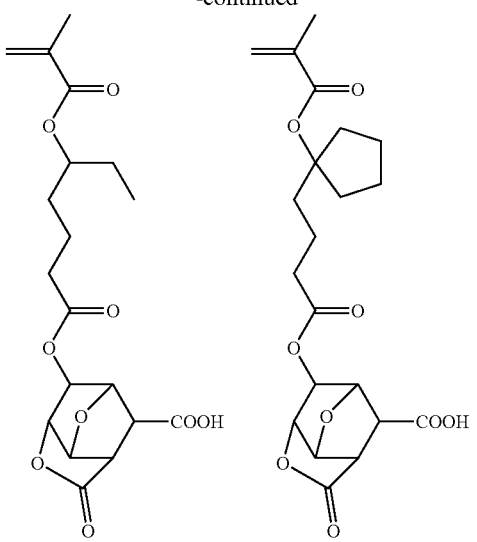
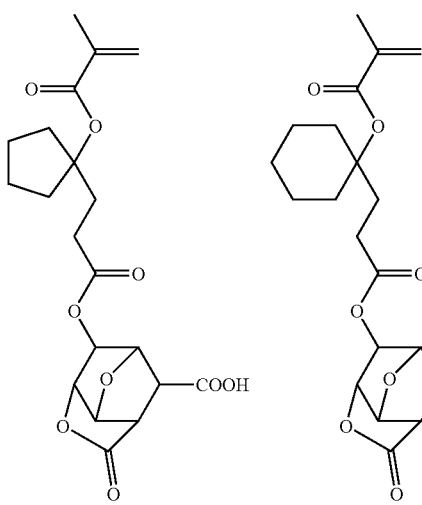
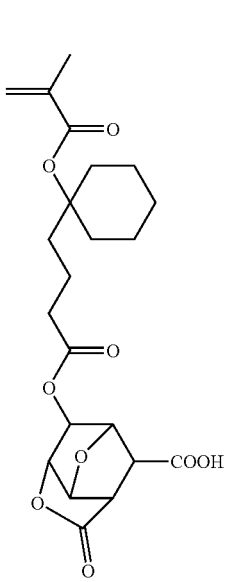
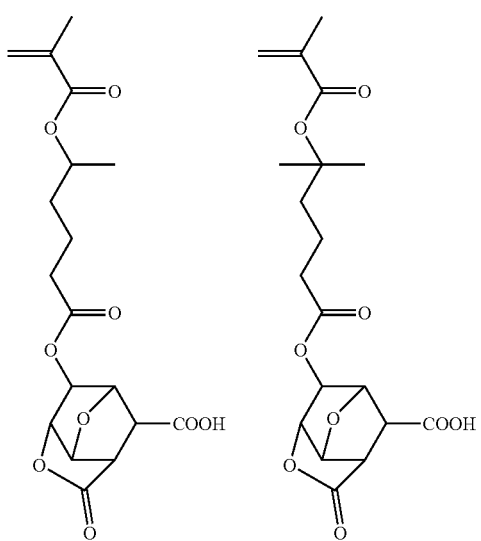
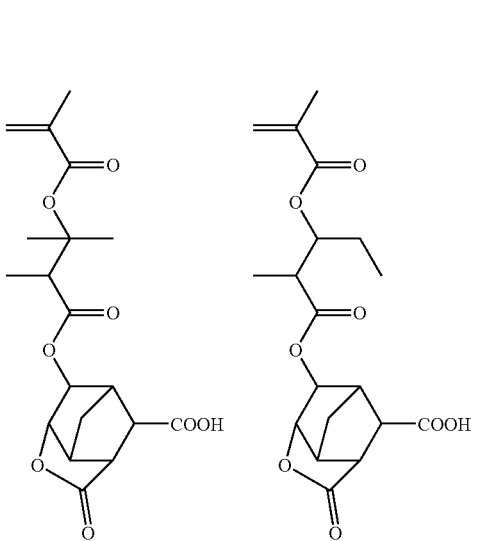

17
-continued
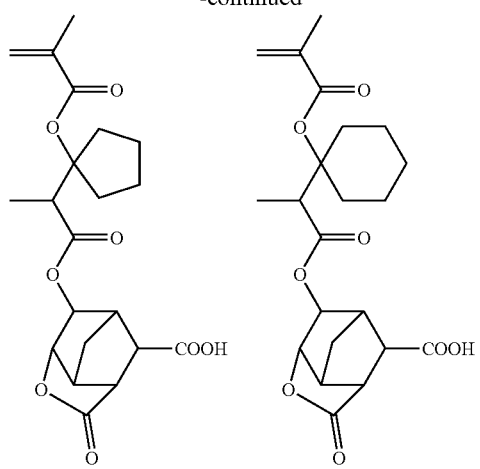
18
-continued
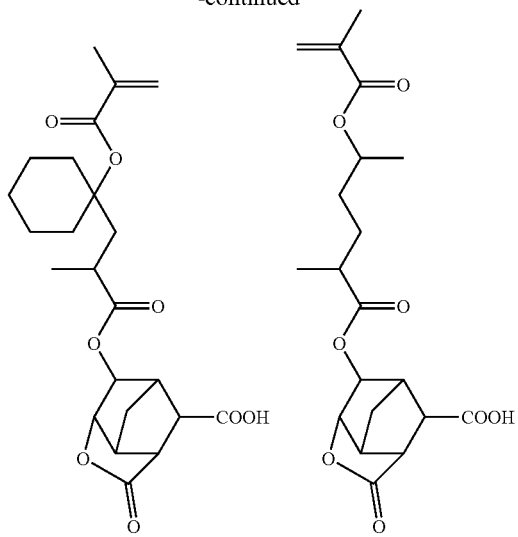
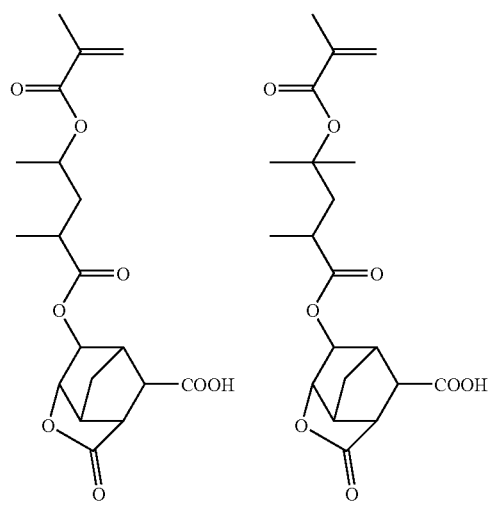
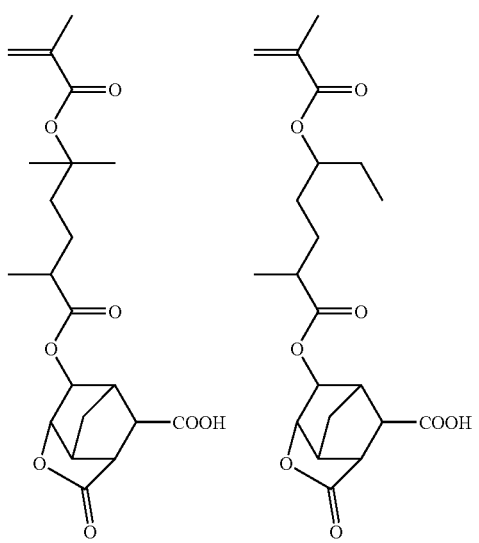
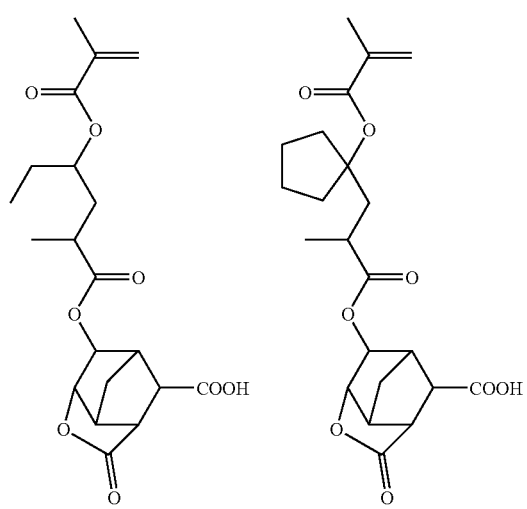
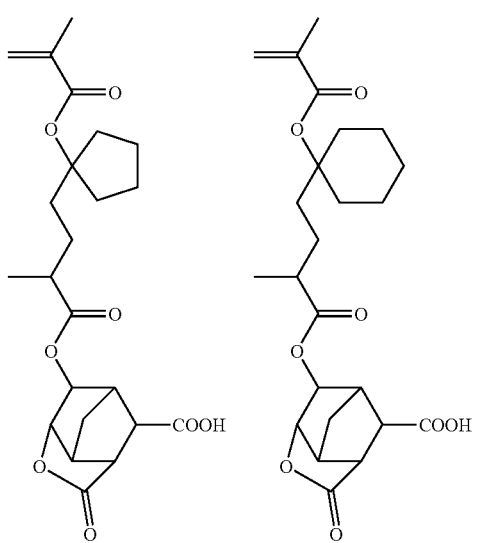

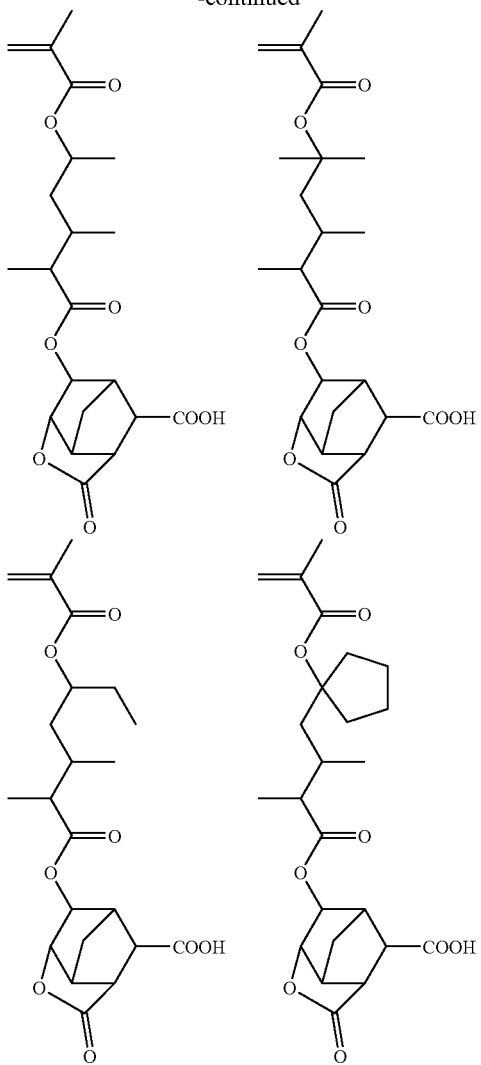
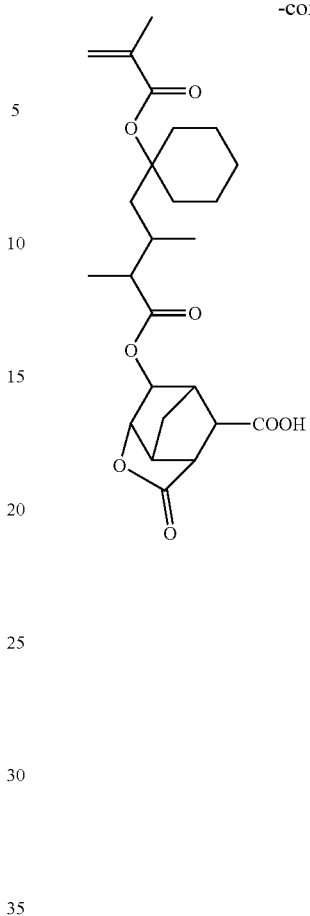
The carboxyl-containing lactone compounds of formula (1) can be produced in accordance with reaction scheme A or B shown below, for example, but their preparation is not limited thereto.
Scheme A
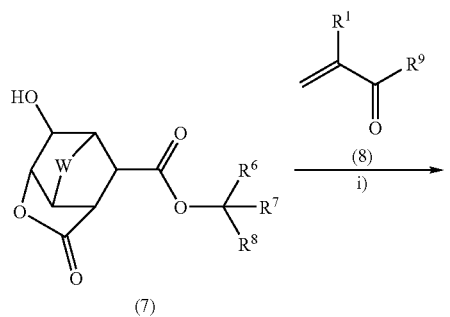

-continued
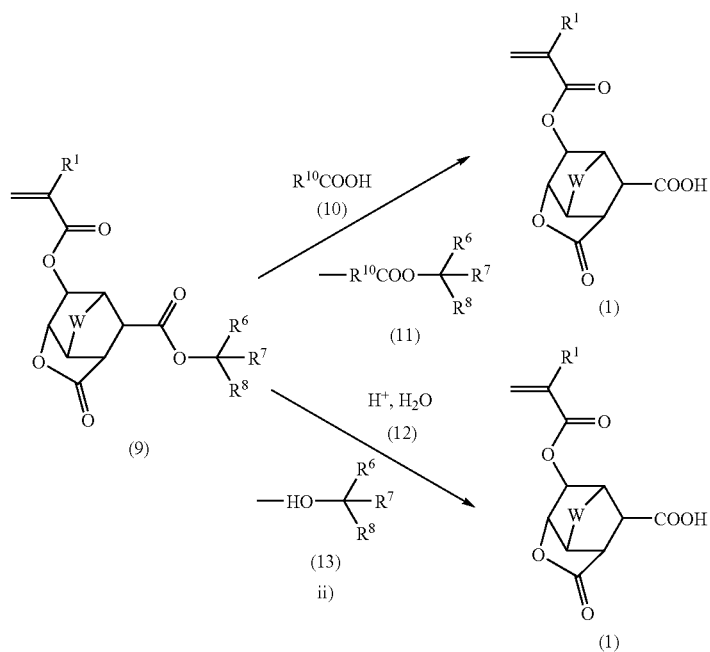
Scheme B
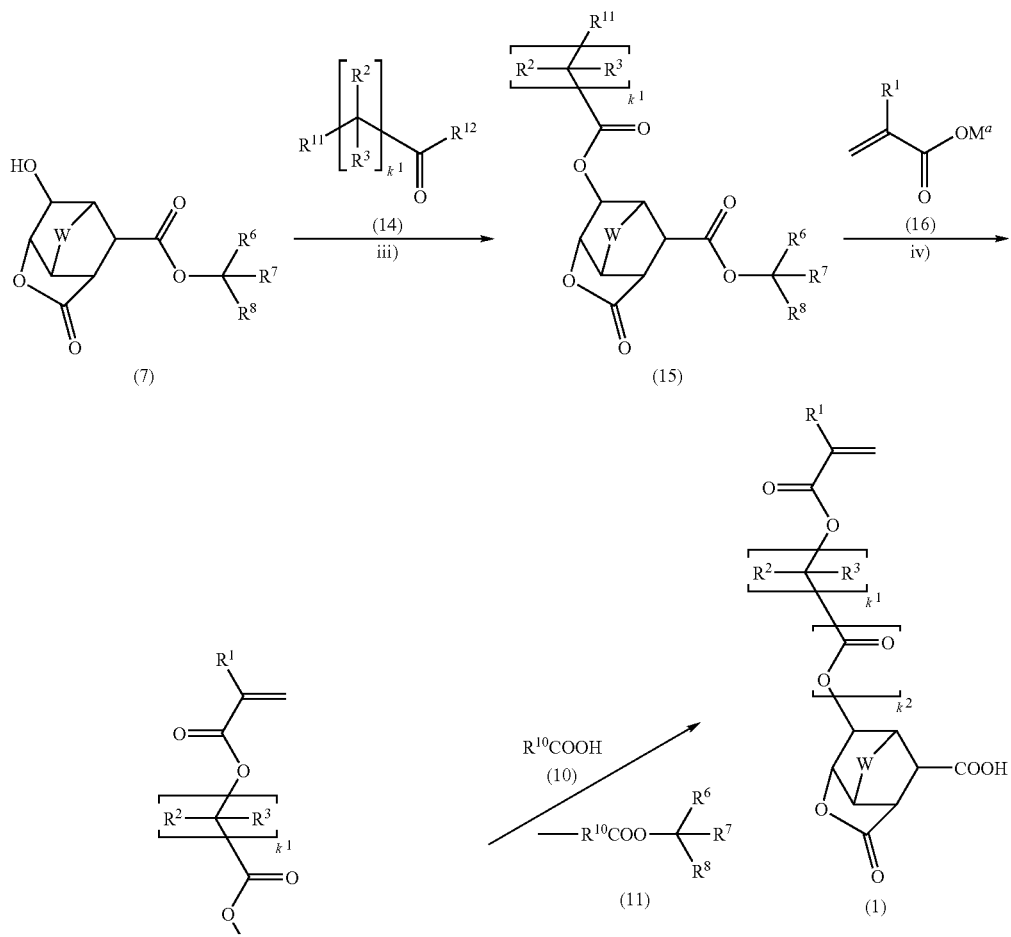

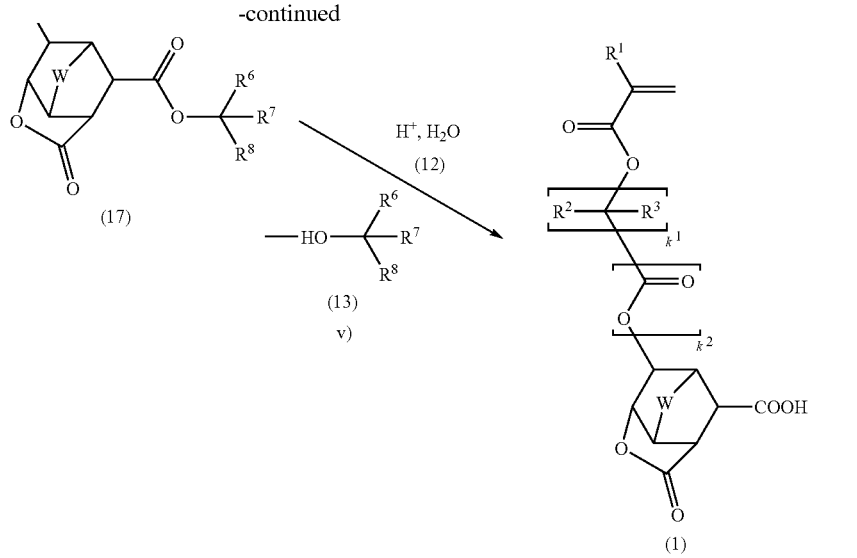

Herein, $R^1$ to $R^3$, W, $k^1$, and $k^2$ are as defined above. $R^6$, $R^7$ and $R^8$ are each independently hydrogen or a straight, branched or cyclic monovalent $C_1$-$C_6$ hydrocarbon group, or $R^6$, $R^7$ and $R^8$ may bond together to form an aliphatic hydrocarbon ring with the carbon atom to which they are attached. $R^9$ is a halogen atom, hydroxyl group or —$OR^{13}$. $R^{10}$ is a straight, branched or cyclic monovalent $C_1$-$C_6$ hydrocarbon group. $R^{11}$ is hydrogen or halogen. $R^{12}$ is a halogen atom, hydroxyl group or —$OR^{14}$. $R^{13}$ is methyl, ethyl or a group of the following formula.

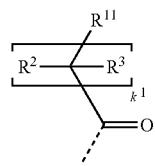

$R^{14}$ is methyl, ethyl or a group of the following formula.

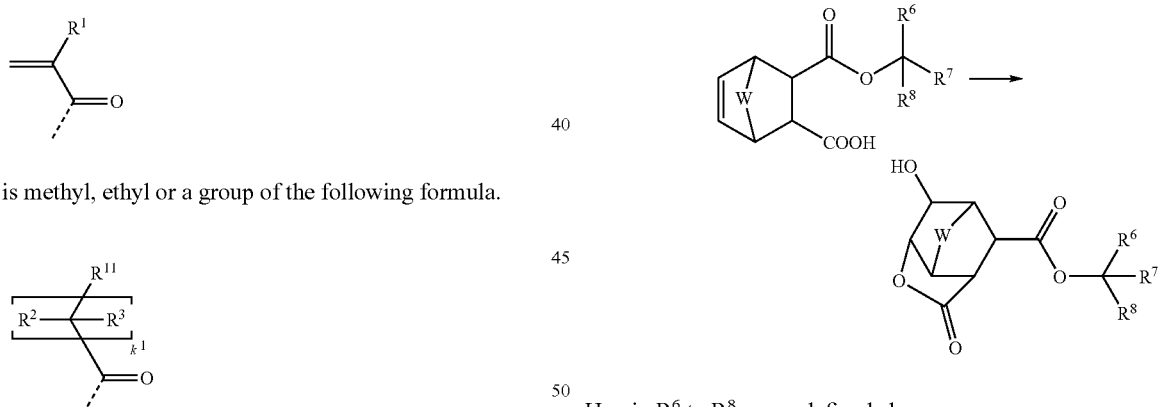

$M^a$ is Li, Na, K, $Mg_{1/2}$, $Ca_{1/2}$ or a substituted or unsubstituted ammonium.

Preferably those carboxyl-containing lactone compounds of formula (1) wherein both $k^1$ and $k^2$ are zero (0) are produced by the process including steps i) to ii) as shown by scheme A, and those carboxyl-containing lactone compounds of formula (1) wherein $k^1$ is 1 to 4 and $k^2$ is 1 are produced by the process including steps iii) to v) as shown by scheme B. The process of preparing lactone compounds is not limited thereto.

More particularly, scheme A includes step i) which is a reaction of a hydroxylactone compound (7) with an esterifying agent (8) to form a lactone-containing compound (9).

Notably, the synthesis of hydroxylactone compound (7) is described in JP-A 2000-159758 and U.S. Ser. No. 11/649,251 (JP-A 2007-182488). For example, hydroxylactone compound (7) may be synthesized according to the following reaction scheme.

Herein $R^6$ to $R^8$ are as defined above.

The reaction of step i) runs readily by any well-known procedure. The preferred esterifying agent (8) is an acid chloride (corresponding to formula (8) wherein $R^9$ is chlorine) or a carboxylic acid (corresponding to formula (8) wherein $R^9$ is hydroxyl). When an acid chloride is used as the esterifying agent, the reaction may be conducted in a solventless system or in a solvent such as methylene chloride, toluene or hexane, by sequentially or simultaneously adding hydroxylactone compound (7), a corresponding acid chloride such as methacrylic acid chloride or acrylic acid chloride, and a base such as triethylamine, pyridine or 4-dimethylaminopyridine, and optionally cooling or heating. When a carboxylic acid is used as the esterifying agent, the reaction may be conducted in a solvent such as toluene or hexane, by heating hydroxylactone compound (7) and a corresponding carboxylic acid such as methacrylic acid or acrylic acid, in the presence of an acid catalyst, and optionally removing the water formed during reaction from the system. Examples of the acid catalyst used herein include mineral acids such as hydrochloric acid, sulfuric acid, nitric acid and perchloric acid, and organic acids such as p-toluenesulfonic acid and benzenesulfonic acid.

Step ii) is to convert the lactone-containing compound (9) to a carboxyl-containing lactone compound (I) by reaction with a carboxylic acid (10) or hydrolysis with the aid of a protonic acid (12).

The reaction of step ii) may readily run as long as a stoichiometric excess of carboxylic acid (10) or protonic acid (12) is added to lactone-containing compound (9). The reaction temperature may be selected as appropriate in accordance with other reaction conditions and is preferably in the range from room temperature to approximately the boiling point of the solvent. Preferably the reaction time is determined so as to attain increased yields by monitoring the reaction process by thin-layer chromatography (TLC) or gas chromatography (GC). At the end of reaction, carboxyl-containing lactone compound (I) is readily recovered from the reaction solution by using an evaporator for azeotroping off carboxylic acid (10) and ester (11) or acid (12) and alcohol (13) with toluene. If necessary, the compound may be purified by a standard technique such as distillation, recrystallization or chromatography.

Scheme B includes step iii) which is a reaction of a hydroxylactone compound (7) with an esterifying agent (14) to form a (halo)acetate (15).

The reaction may be readily conducted by a well-known technique. The preferred esterifying agent (14) is an acid chloride (corresponding to formula (14) wherein $R^{12}$ is chlorine) or a carboxylic acid (corresponding to formula (14) wherein $R^{12}$ is hydroxyl). When an acid chloride is used as the esterifying agent, the reaction may be conducted in a solventless system or in a solvent such as methylene chloride, toluene, hexane, diethyl ether, tetrahydrofuran or acetonitrile, by sequentially or simultaneously adding hydroxylactone compound (7), a corresponding acid chloride such as 2-chloroacetic acid chloride or 2-bromoacetic acid chloride, and a base such as triethylamine, pyridine or 4-dimethylaminopyridine, and optionally cooling or heating. When a carboxylic acid is used as the esterifying agent, the reaction may be conducted in a solvent such as toluene or hexane, by heating hydroxylactone compound (7) and a corresponding carboxylic acid such as 2-chloroacetic acid or 2-bromoacetic acid, in the presence of an acid catalyst, and optionally removing the water formed during reaction from the system. Examples of the acid catalyst used herein include mineral acids such as hydrochloric acid, sulfuric acid, nitric acid and perchloric acid, and organic acids such as p-toluenesulfonic acid and benzenesulfonic acid.

Step iv) is a reaction of a halo-acetate (15) (formula (15) wherein $R^{11}$ is a halogen atom) with a carboxylate salt (16) to form a lactone-containing compound (17).

The reaction may be conducted by a standard technique. The carboxylic acid salt (16) used herein may be any of commercially available carboxylic acid salts such as metal salts of carboxylic acids, or may be prepared in a reaction system using a corresponding carboxylic acid such as methacrylic acid or acrylic acid and a base. The amount of carboxylic acid salt (16) used is preferably 0.5 to 10 moles, and more preferably 1.0 to 3.0 moles per mole of the reactant, halo-acetate (15). With less than 0.5 mole of the carboxylic acid salt, a large proportion of the reactant may be left unreacted, leading to a substantial drop of yield. Using more than 10 moles of the carboxylic acid salt may be uneconomical because of an increased cost of the salt and decreased pot yields. When the carboxylic acid salt is prepared in a reaction system using a corresponding carboxylic acid and a base, the base used herein may be selected from among amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogen carbonate; metals such as sodium; metal hydrides such as sodium hydride; metal alkoxides such as sodium methoxide and potassium t-butoxide; organometallic compounds such as butyllithium and ethylmagnesium bromide; and metal amides such as lithium diisopropylamide, and mixtures thereof. The amount of the base used is preferably 0.2 to 10 moles, and more preferably 0.5 to 2.0 moles per mole of the carboxylic acid. With less than 0.2 mole of the base, a large proportion of the carboxylic acid may run to waste, leading to a cost deficiency. With more than 10 moles of the base, substantial side reactions may occur, resulting in a substantial drop of yield.

A solvent may be used in the reaction of step iv). Suitable solvents include hydrocarbons such as toluene, xylene, hexane and heptane; chlorinated solvents such as methylene chloride, chloroform and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide, and dimethyl sulfoxide; and water, which may be used alone or in admixture. To the reaction system, a phase transfer catalyst such as tetrabutylammonium hydrogen sulfate may be added. An appropriate amount of the phase transfer catalyst added is 0.0001 to 1.0 mole, and more preferably 0.001 to 0.5 mole per mole of the reactant, alcohol compound. Less than 0.0001 mole of the catalyst may exert little or no addition effect whereas more than 1.0 mole may be uneconomical because of an increased expense.

For the esterification reaction described above, the reaction temperature may be selected as appropriate in accordance with other reaction conditions and is preferably in the range from −70° C. to approximately the boiling point of the solvent, and more preferably in the range from 0° C. to approximately the boiling point of the solvent. The higher the reaction temperature, the more outstanding become side reactions. It is then important in attaining high yields that the reaction be carried out at as low a temperature as possible in the range for the reaction to proceed at a practically acceptable rate. Preferably the reaction time is determined so as to attain increased yields by monitoring the reaction process by TLC or GC. Usually, the reaction time is about 30 minutes to about 40 hours. From the reaction mixture, the lactone-containing compound (17) is recovered through an ordinary aqueous workup. If necessary, the compound may be purified by a standard technique such as distillation, recrystallization or chromatography.

Step v) is to convert the lactone-containing compound (17) to a carboxyl-containing lactone compound (I) by reaction with a carboxylic acid (10) or hydrolysis with the aid of a protonic acid (12).

The reaction of step v) may readily run as long as a stoichiometric excess of carboxylic acid (10) or protonic acid (12) is added to lactone-containing compound (17). The reaction temperature may be selected as appropriate in accordance with other reaction conditions and is preferably in the range from room temperature to approximately the boiling point of the solvent. Preferably the reaction time is determined so as to attain increased yields by monitoring the reaction process by TLC or GC. At the end of reaction, carboxyl-containing lactone compound (1) is readily recovered from the reaction solution by using an evaporator for azeotroping off carboxylic acid (10) and ester (11) or acid (12) and alcohol (13) with toluene. If necessary, the compound may be purified by a standard technique such as distillation, recrystallization or chromatography.

Polymer

In the second aspect, the invention provides a polymer comprising recurring units derived from the carboxyl-containing lactone compound of formula (1).

Specifically, the recurring units derived from the carboxyl-containing lactone compound of formula (1) include units having the general formula (2).

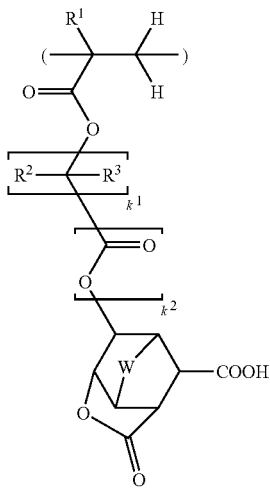

(2)

Herein $R^1$ to $R^3$, W, $k^1$ and $k^2$ are as defined above.

In addition to the recurring units derived from the lactone compounds having formula (1), specifically recurring units having formula (2), the polymers of the invention may further comprise recurring units of at least one type selected from the general formulas (3) to (6).

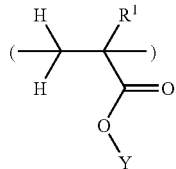

(3)

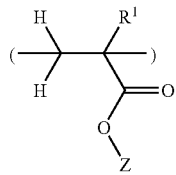

(4)

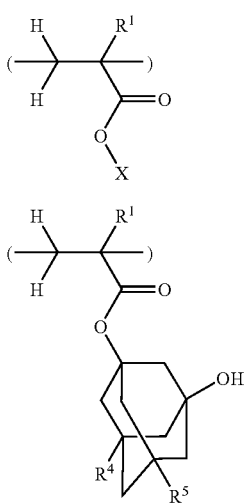

(5)

(6)

Herein $R^1$ is as defined above, $R^4$ and $R^5$ are each independently hydrogen or hydroxyl, X is an acid labile group, Y is a substituent group having a lactone structure different from formula (1), and Z is hydrogen, a $C_1$-$C_{15}$ fluoroalkyl group or a $C_1$-$C_{15}$ fluoroalcohol-containing substituent group.

Under the action of acid, a polymer comprising recurring units of formula (3) is decomposed to generate carboxylic acid, turning to be an alkali soluble polymer. The acid labile group represented by X may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

(L1)

(L2)

(L3)

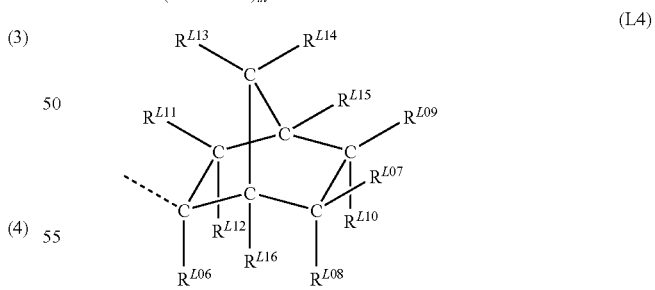

(L4)

In these formulae, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, n-propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples of the substituted alkyl groups are shown below.

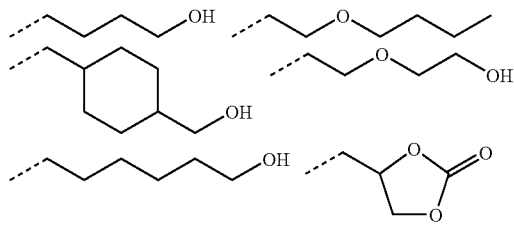

A pair of $R^{L01}$ and $R^{L02}$, $R^{L01}$ and $R^{L03}$, or $R^{L02}$ and $R^{L03}$ may form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a substituted or unsubstituted, straight, branched or cyclic alkyl group of 1 to 8 carbon atoms or a substituted or unsubstituted aryl group of 6 to 20 carbon atoms. Examples of the optionally substituted alkyl group include straight, branched or cyclic alkyl groups such as methyl, ethyl, propyl, isopropyl, n-butyl, sec-butyl, tert-butyl, tert-amyl, n-pentyl, n-hexyl, cyclopentyl, and cyclohexyl, and substituted forms of such groups in which some hydrogen atoms are substituted by hydroxyl, alkoxy, carboxy, alkoxycarbonyl, oxo, amino, alkylamino, cyano, mercapto, alkylthio, sulfo or other groups. Examples of the optionally substituted aryl groups include phenyl, methylphenyl, naphthyl, anthryl, phenanthryl, and pyrenyl. Letter m is equal to 0 or 1, n is equal to 0, 1, 2 or 3, and 2m+n is equal to 2 or 3.

In formula (L4), $R^{L06}$ is a substituted or unsubstituted, straight, branched or cyclic alkyl group of 1 to 8 carbon atoms or a substituted or unsubstituted aryl group of 6 to 20 carbon atoms. Examples of these groups are the same as exemplified for $R^{L05}$. $R^{L07}$ to $R^{L16}$ independently represent hydrogen or monovalent hydrocarbon groups of 1 to 15 carbon atoms. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{16}$, taken together, form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

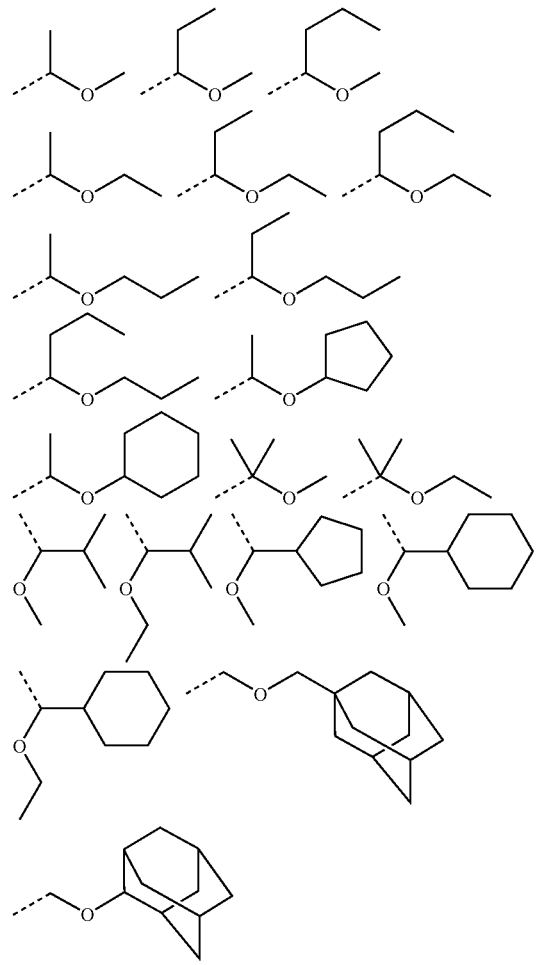

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

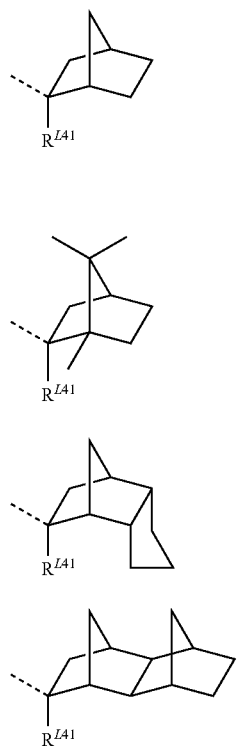

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

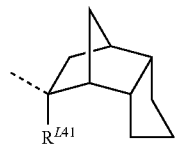

(L4-3-1)

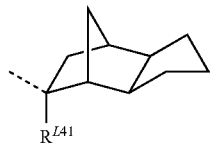

(L4-3-2)

Similarly, the general formula (L4-4) represents one or a mixture of two or more selected from groups having the following general formulas (L4-4-1) to (L4-4-4).

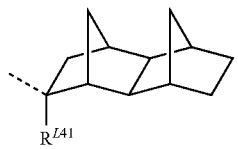

(L4-4-1)

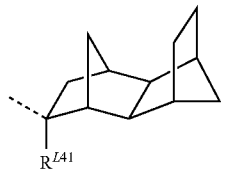

(L4-4-2)

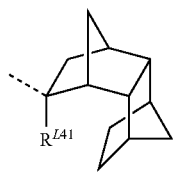

(L4-4-3)

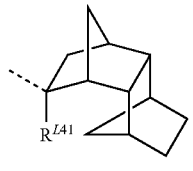

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50% is preferred, with an exo proportion of at least 80% being more preferred.

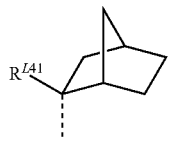

(L4-1-endo)

-continued

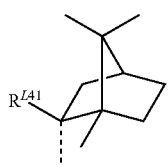
(L4-2-endo)

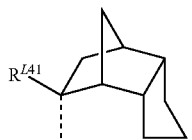
(L4-3-endo)

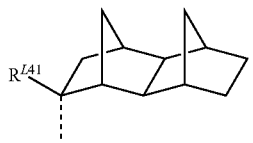
(L4-4-endo)

See JP-A 2000-336121.

Illustrative examples of the acid labile group of formula (L4) are given below.

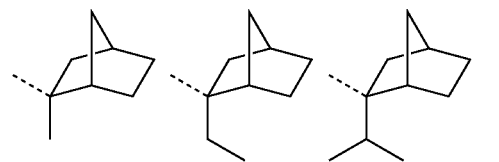

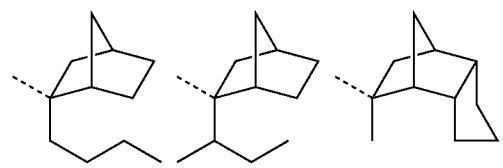

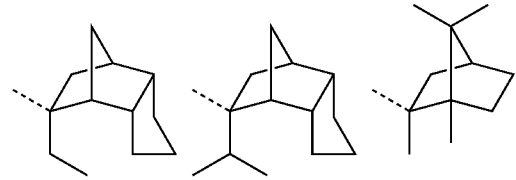

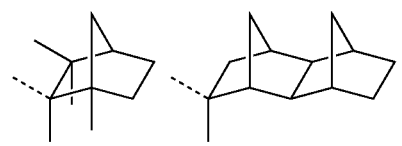

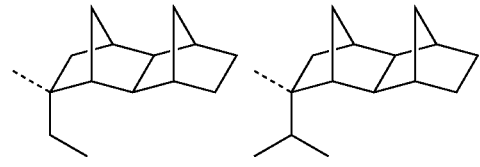

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

Illustrative examples of the recurring units of formula (3) are given below, but not limited thereto.

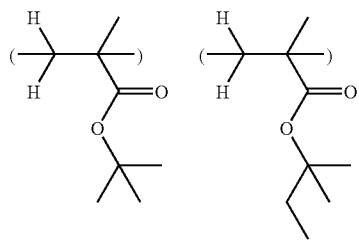

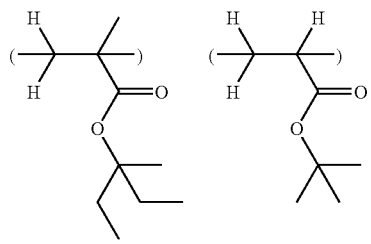

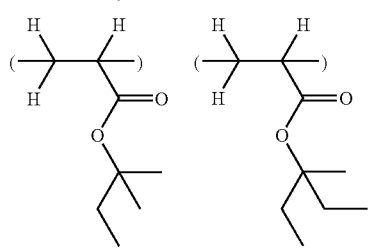

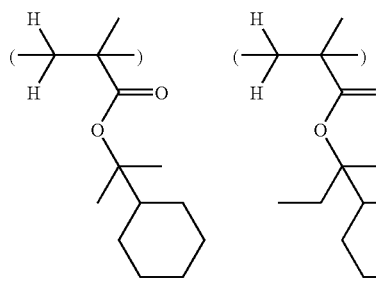

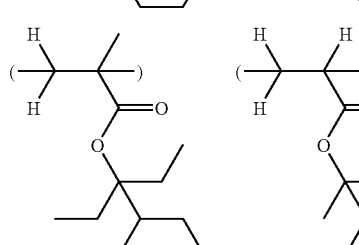

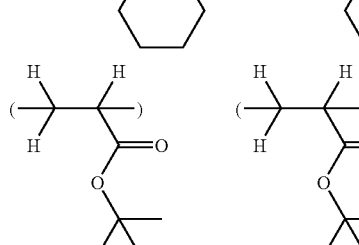

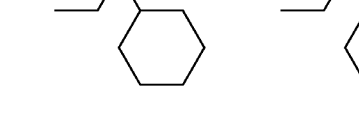

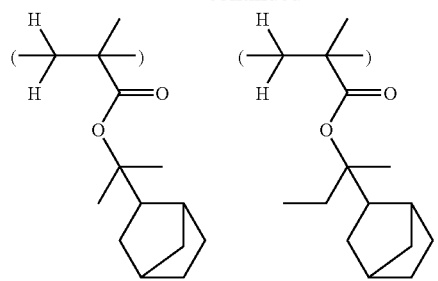
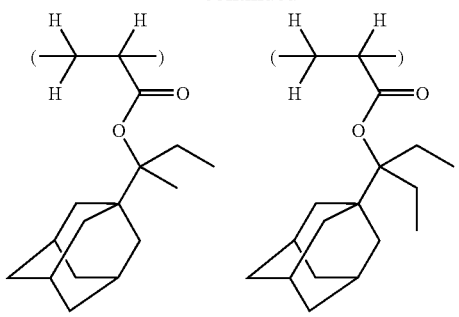
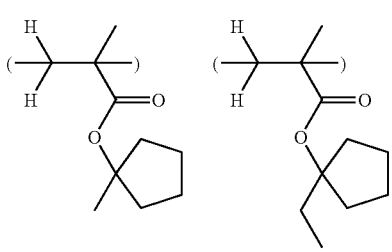
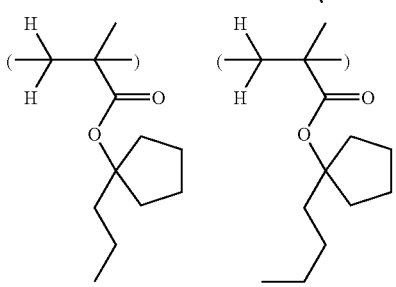
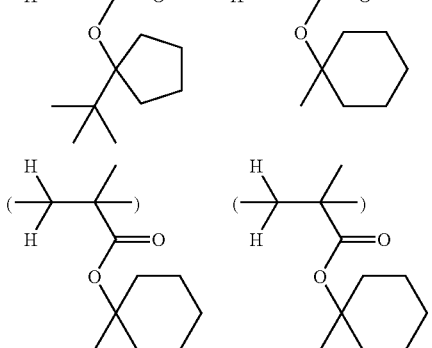
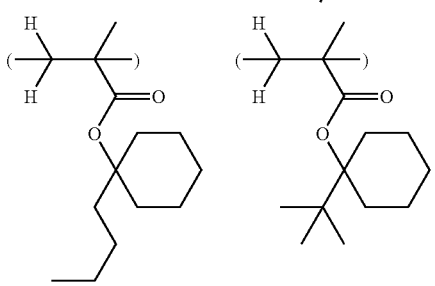

37
-continued
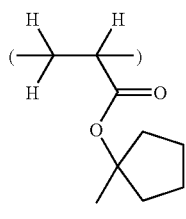 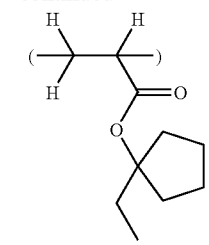
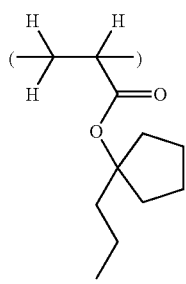 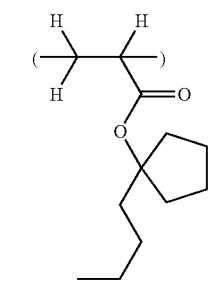
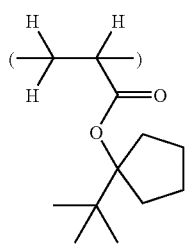 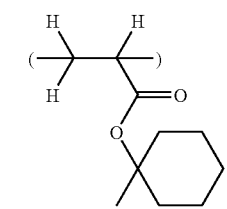
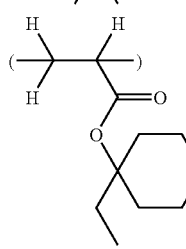 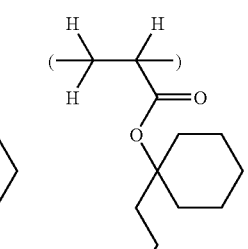
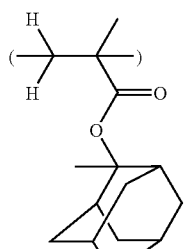 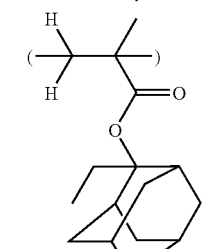
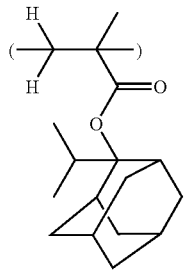 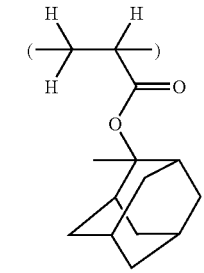
38
-continued
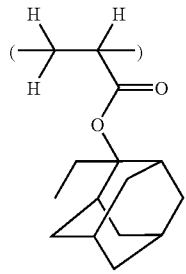 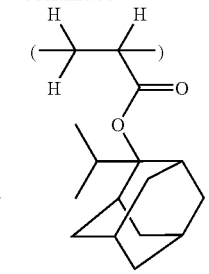
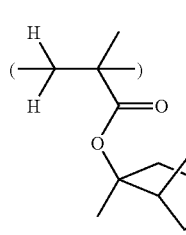 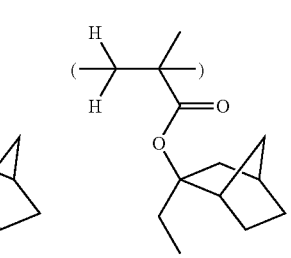
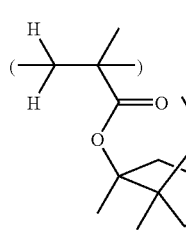 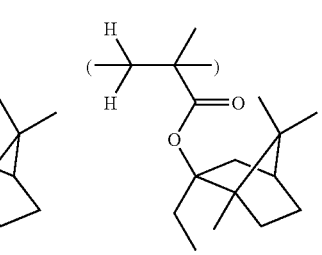
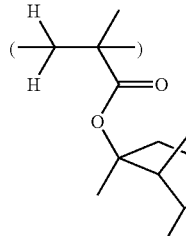 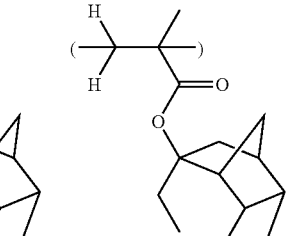
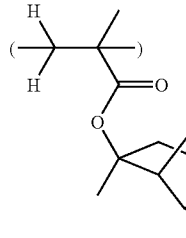 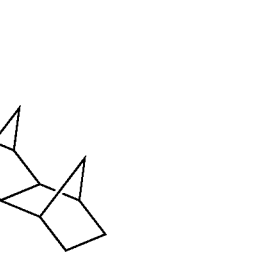
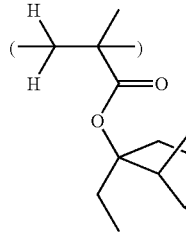 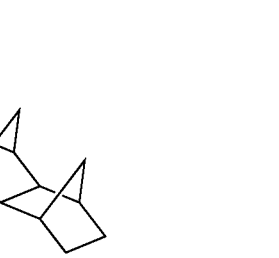

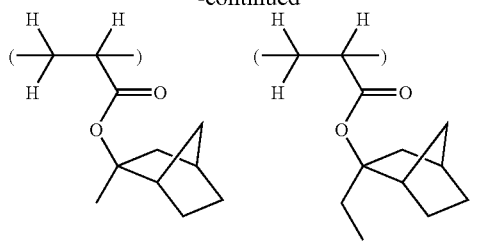
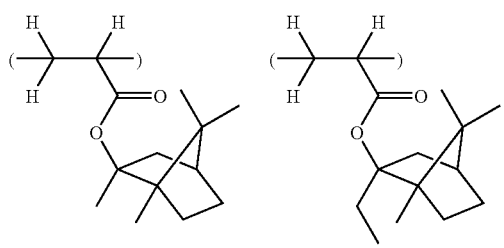
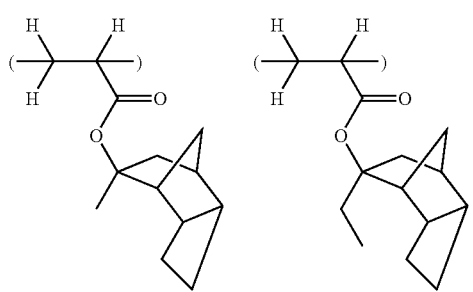
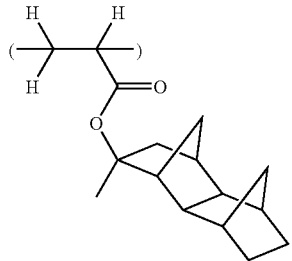
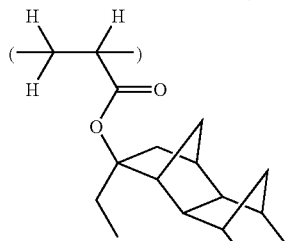
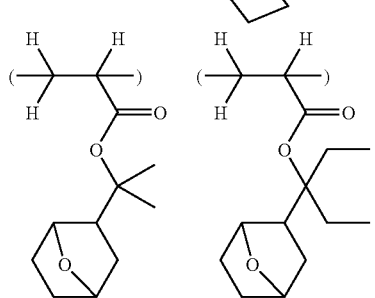
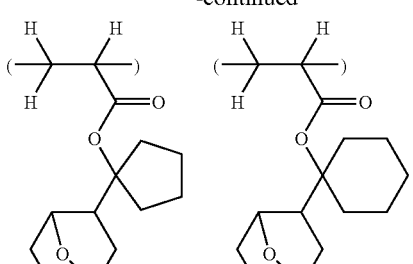
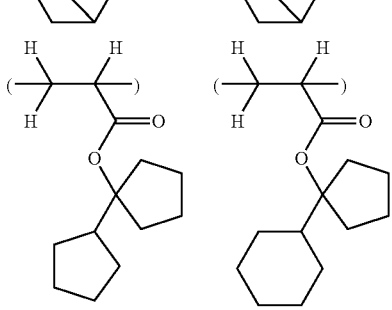
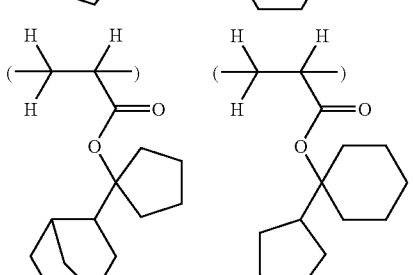
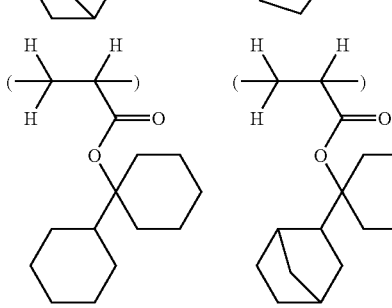
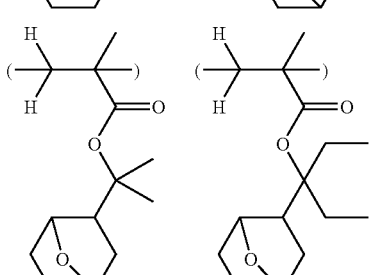
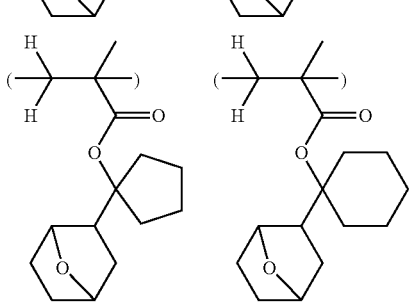

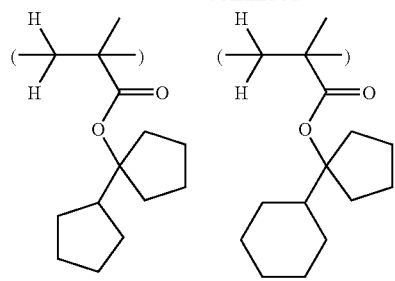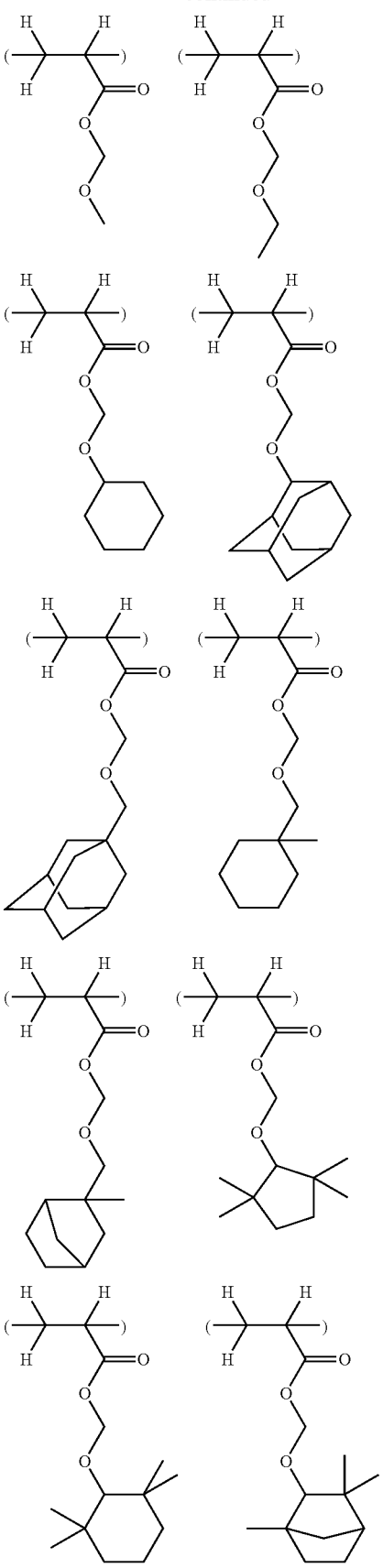

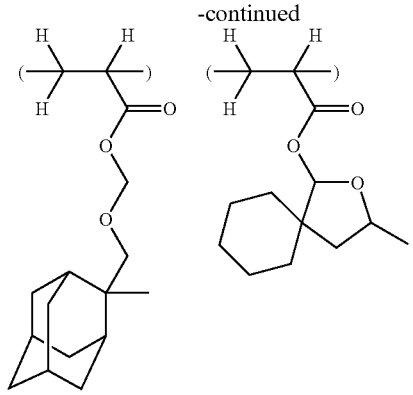
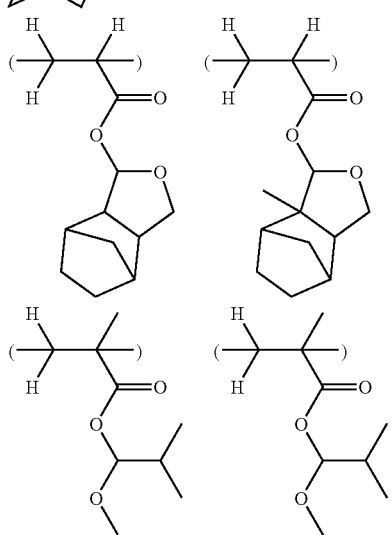
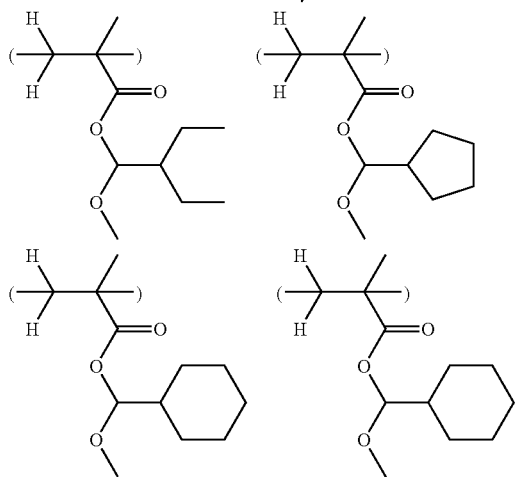
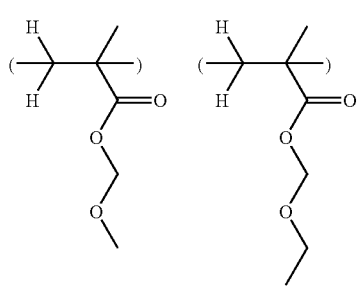
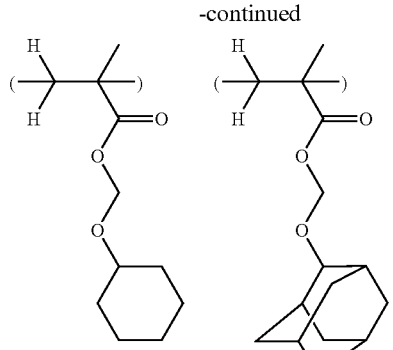
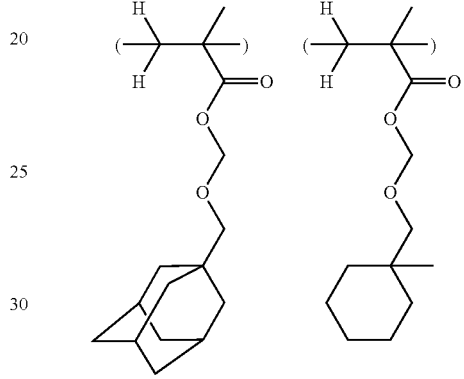
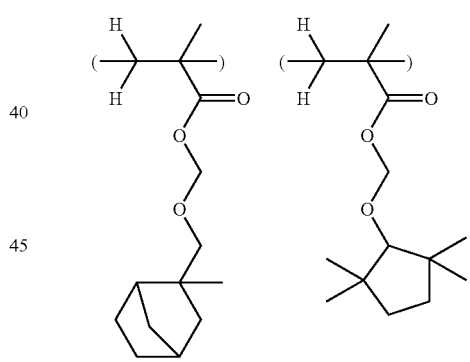
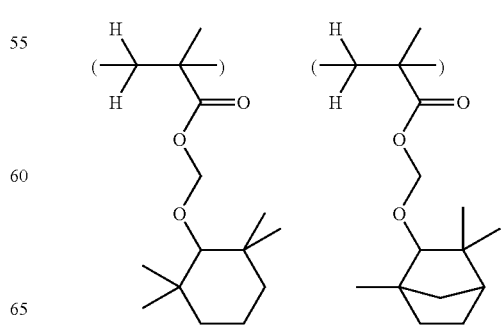

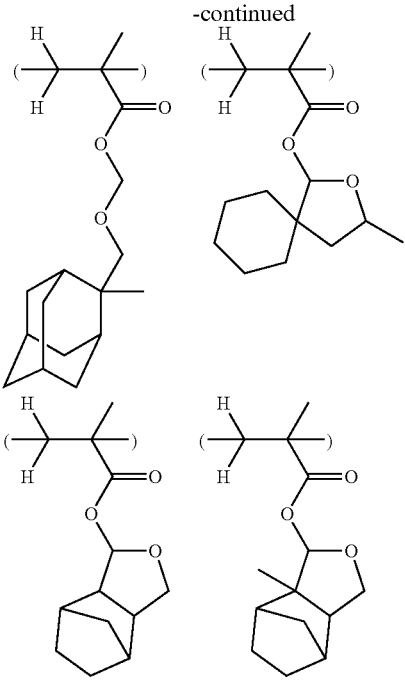
Illustrative examples of the recurring units of formula (4) are given below, but not limited thereto.
Illustrative examples of the recurring units of formula (5) are given below, but not limited thereto.
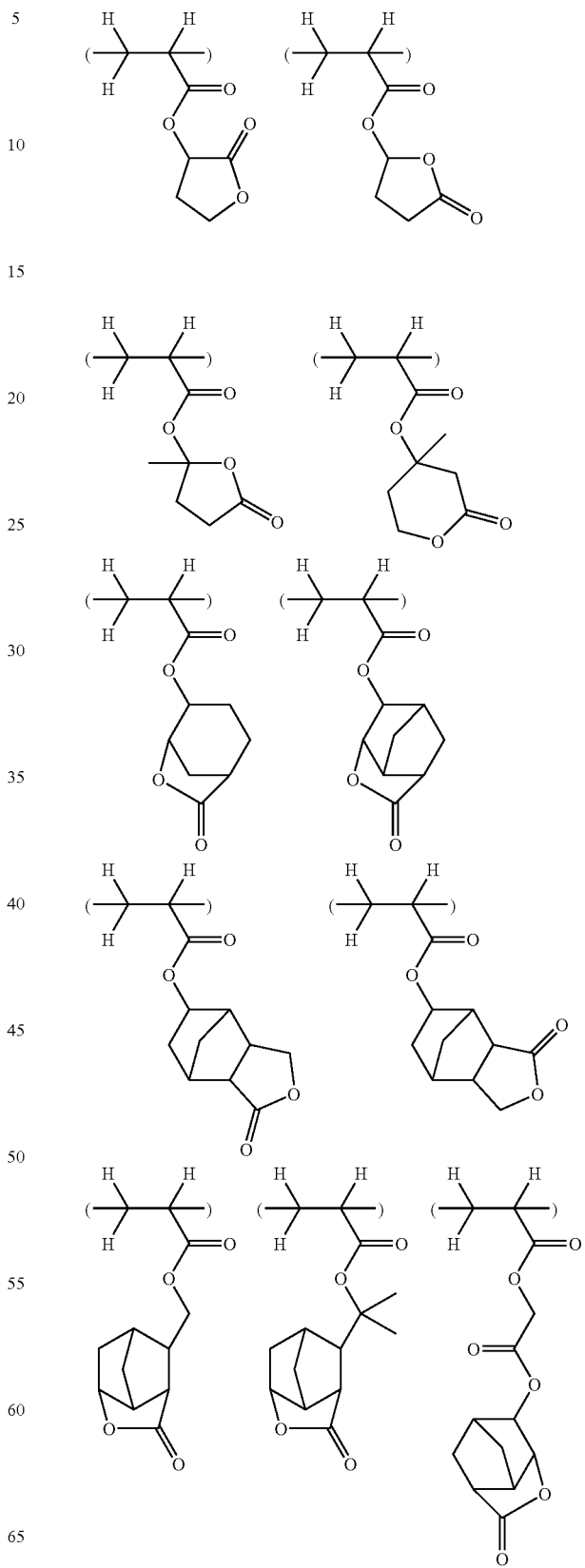

-continued
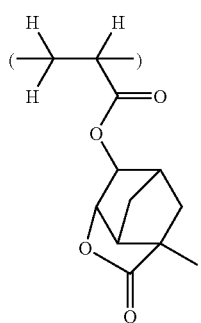 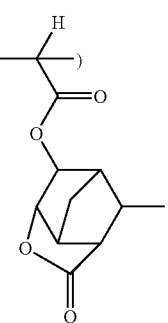
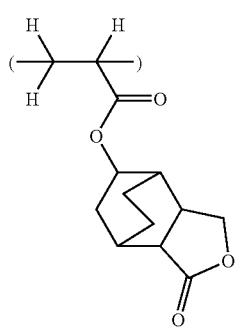 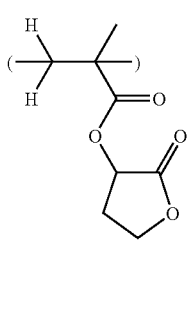
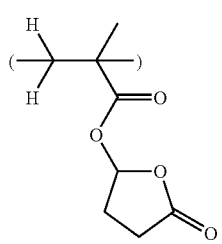 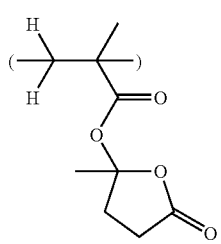
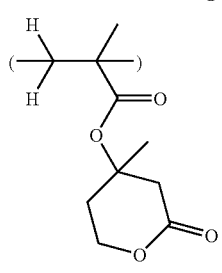 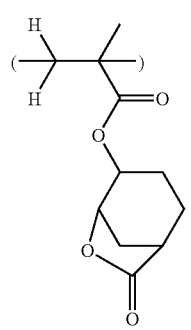
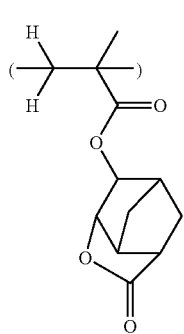 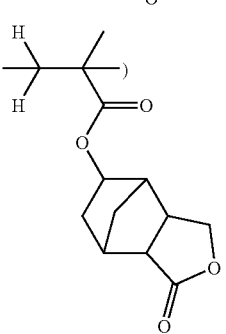
-continued
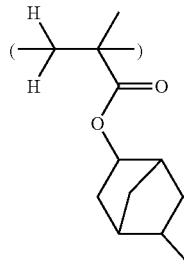 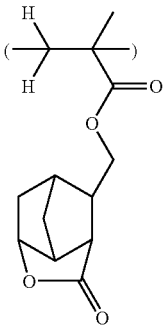
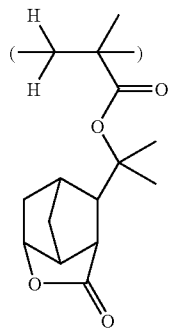 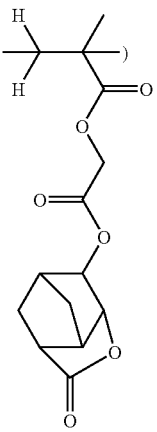
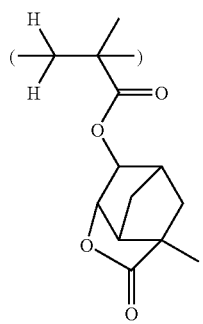 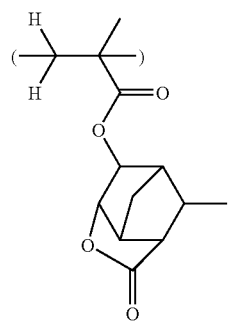
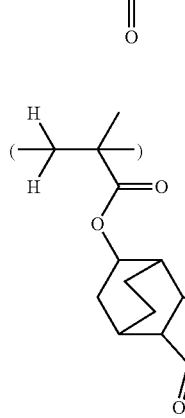 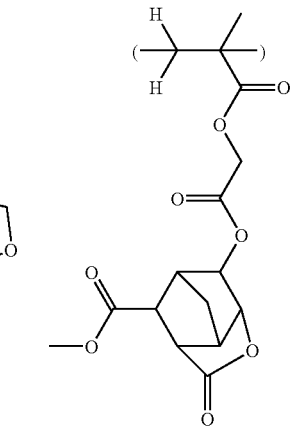

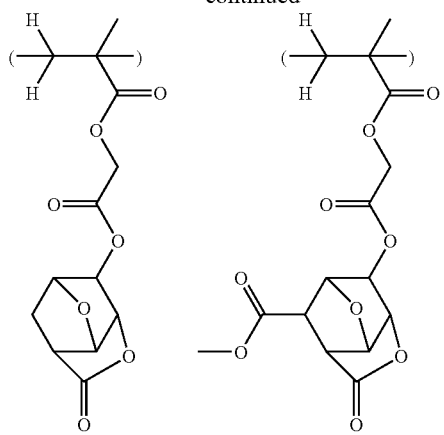
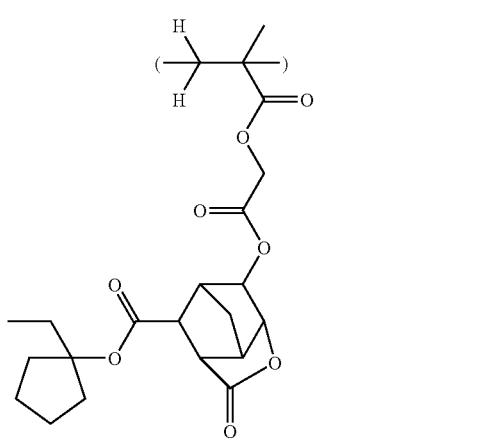
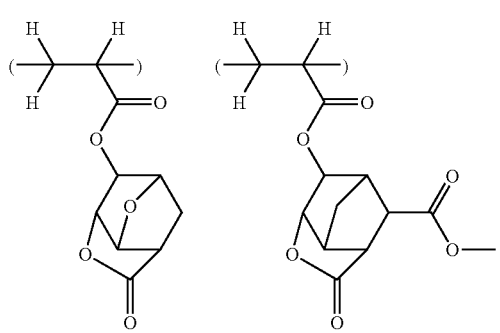
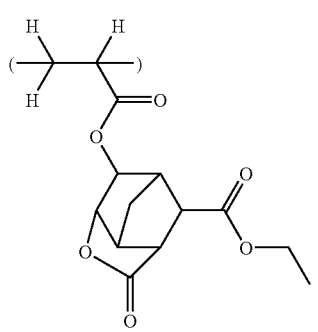
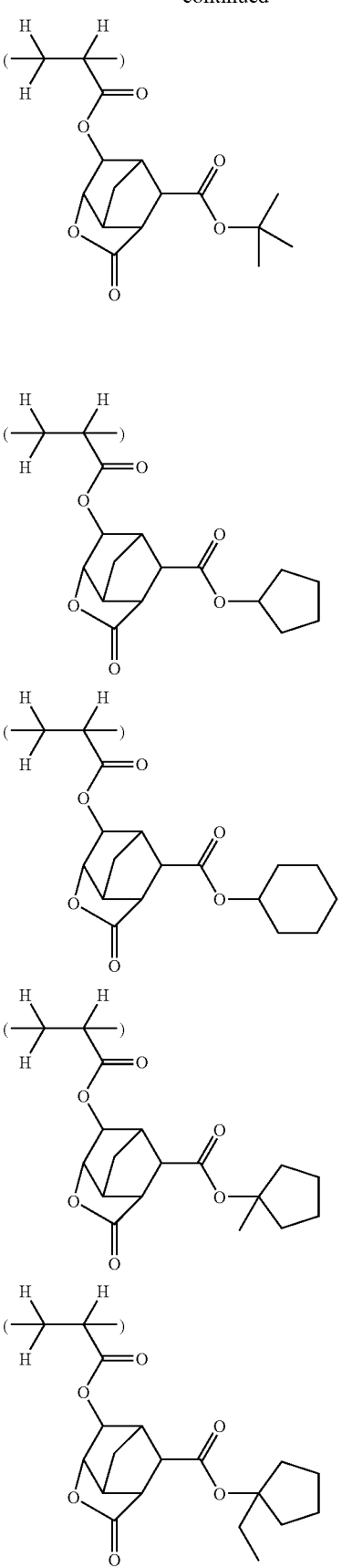

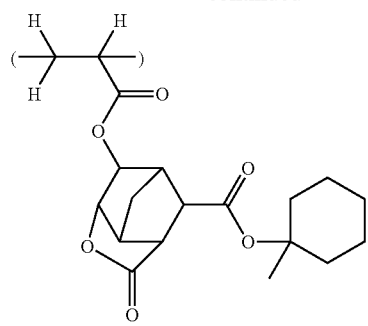
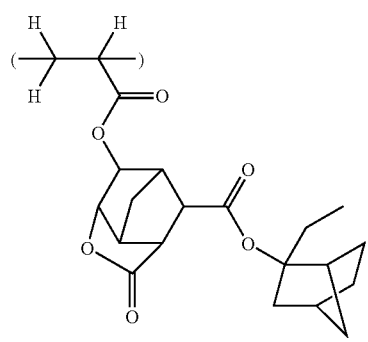
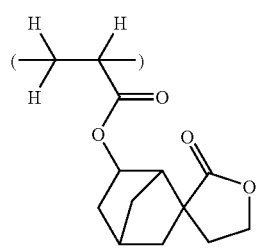
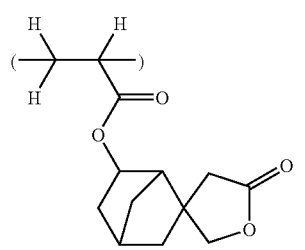
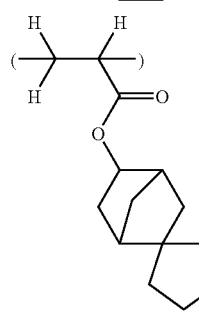
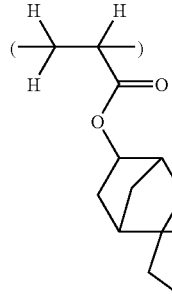
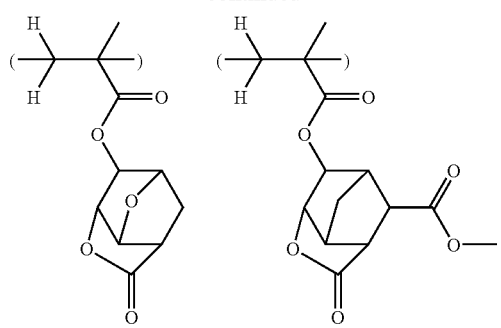
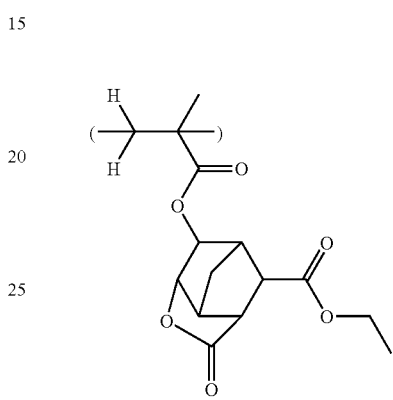
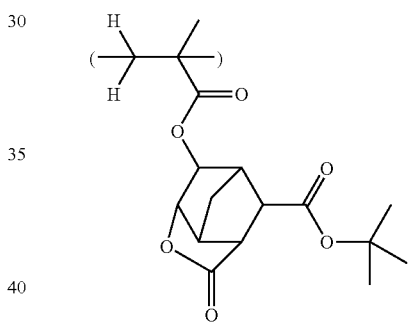
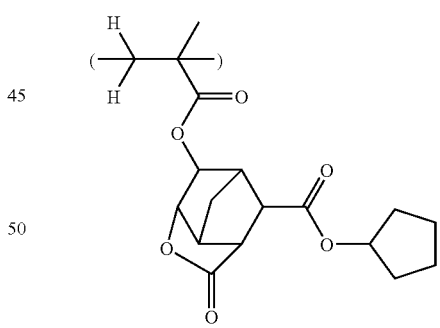
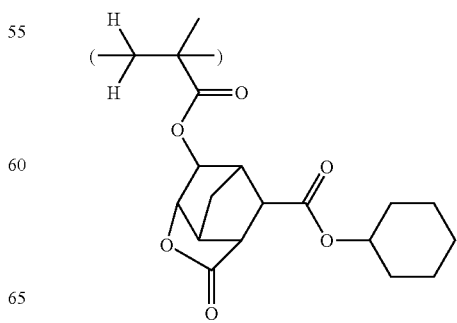

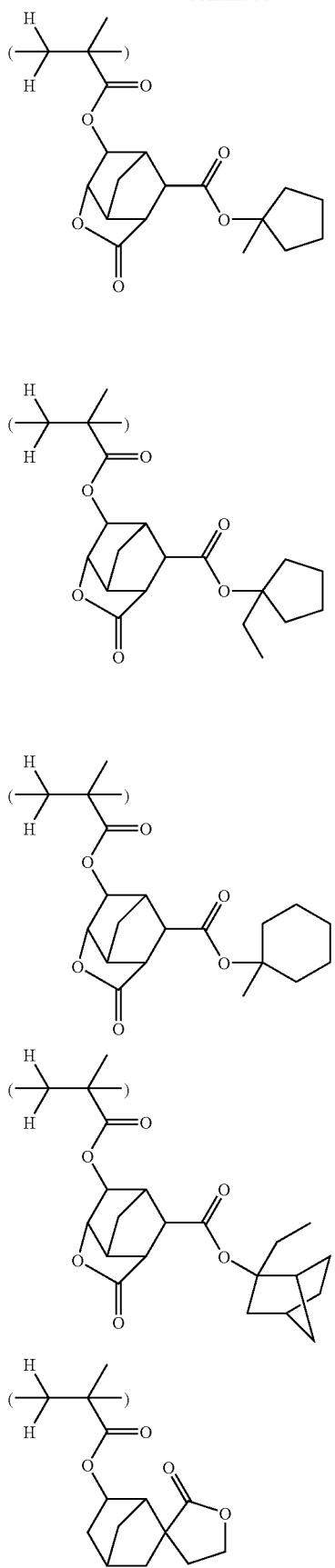
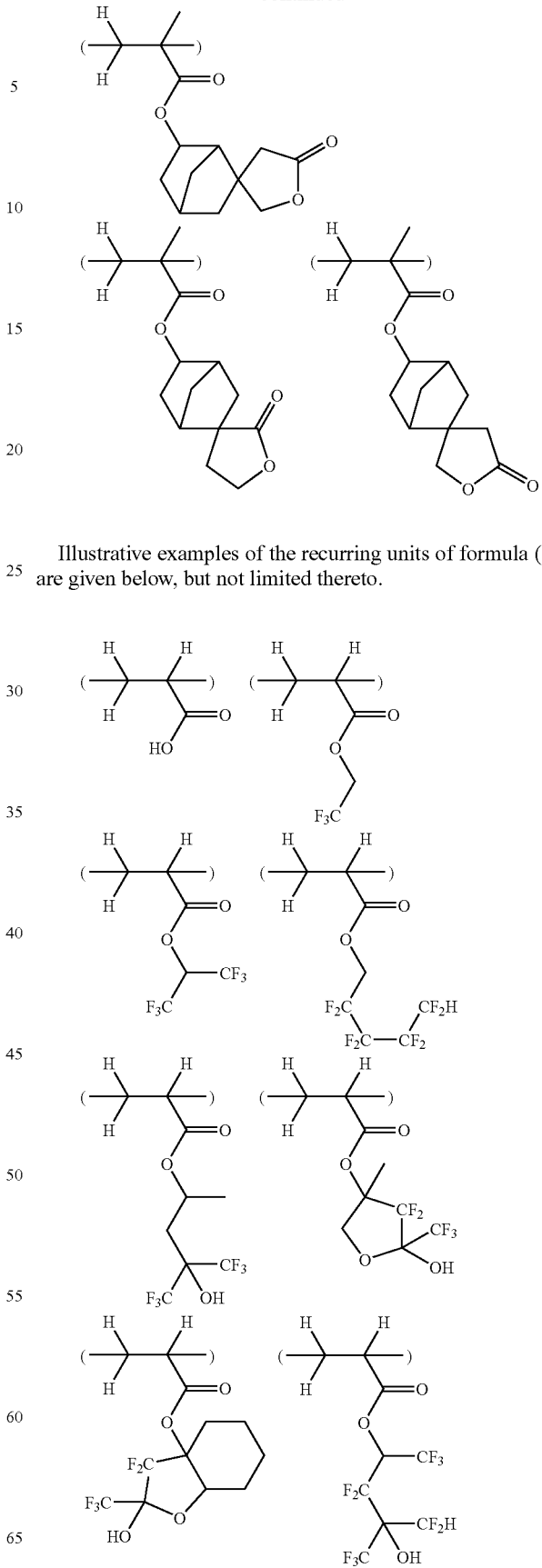
Illustrative examples of the recurring units of formula (6) are given below, but not limited thereto.

-continued
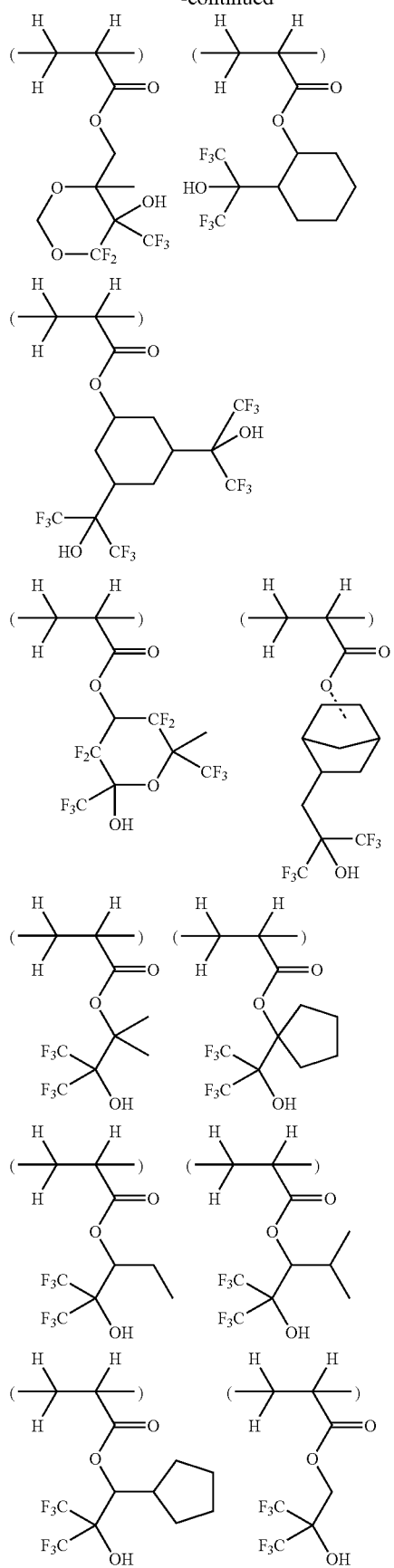
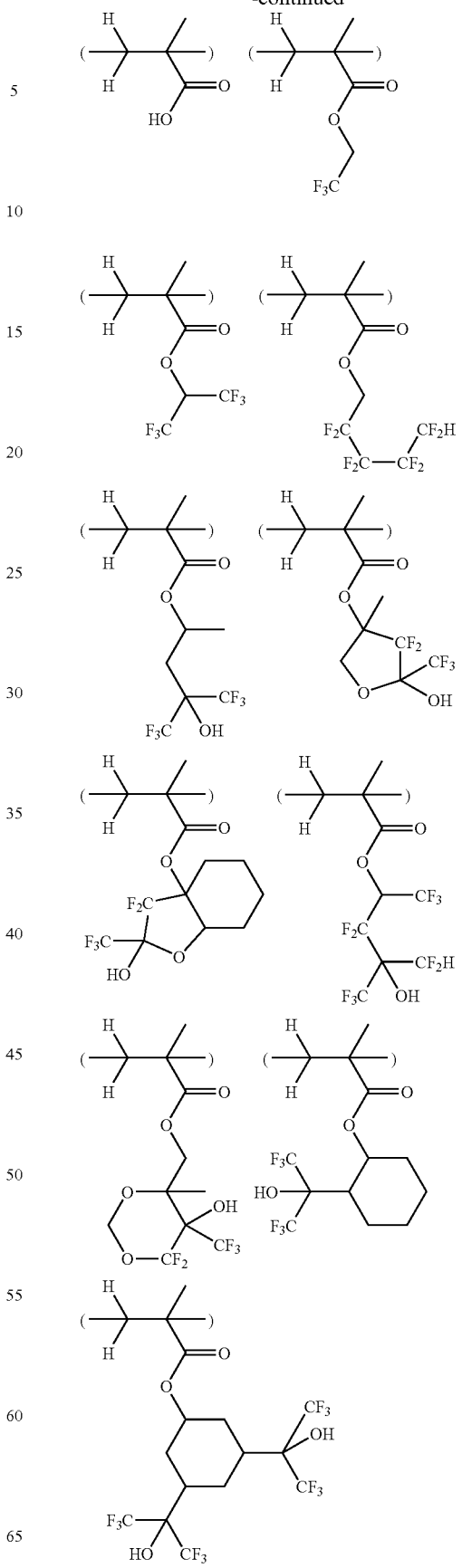

-continued

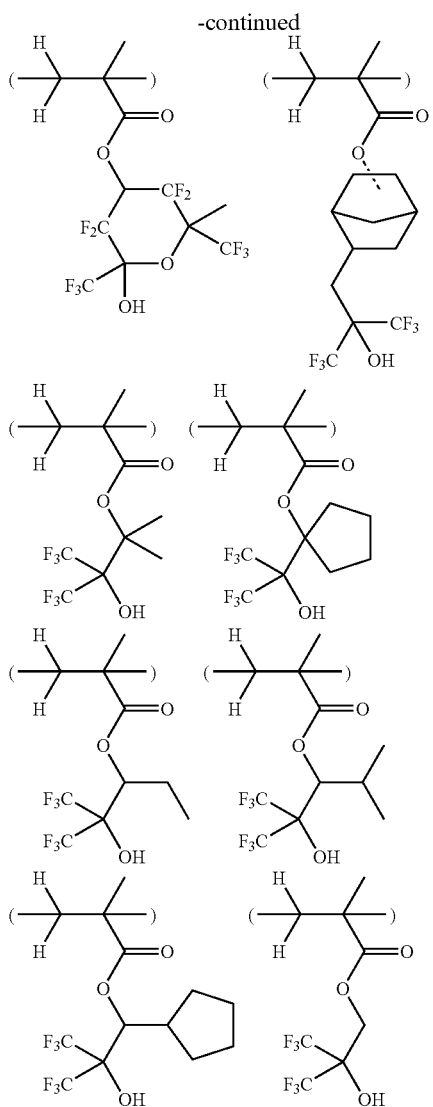

In addition to the foregoing units, the polymers of the invention may further comprise recurring units derived from carbon-to-carbon double bond-bearing monomers other than the above-described ones, for example, substituted acrylic acid esters such as methyl methacrylate, methyl chrotonate, dimethyl maleate and dimethyl itaconate, unsaturated carboxylic acids such as maleic acid, fumaric acid, and itaconic acid, cyclic olefins such as norbornene, norbornene derivatives, and tetracyclo[4.4.0.1$^{2,5}$.1$^{7,10}$]dodecene derivatives, unsaturated acid anhydrides such as itaconic anhydride, and other monomers.

The polymers of the invention generally have a weight average molecular weight (Mw) of 1,000 to 500,000, and preferably 3,000 to 100,000, as measured by gel permeation chromatography (GPC) using polystyrene standards. Outside the range, there may result an extreme drop of etch resistance, and a drop of resolution due to difficulty to gain a dissolution rate difference before and after exposure.

In the inventive polymers, appropriate proportions of the respective recurring units derived from the monomers are given below although the invention is not limited thereto. The inventive polymers may contain:

(I) constituent units of one or more types having formula (2) derived from monomers of formula (1) in a proportion of more than 0 mol % to 100 mol %, preferably 5 to 70 mol %, and more preferably 5 to 50 mol %, (II) constituent units of one or more types having formulas (3) to (6) in a proportion of 0 mol % to less than 100 mol %, preferably 1 to 95 mol %, and more preferably 20 to 90 mol %, and (III) constituent units of one or more types derived from other monomers in a proportion of 0 to 80 mol %, preferably 0 to 70 mol %, and more preferably 0 to 50 mol %, based on the total moles of constituent units.

Of the recurring units of formulas (3) to (6), inclusion of units of formula (3) is preferred, and inclusion of units of formulas (3), (4) and (5) is more preferred. In these embodiments, recurring units of formula (3) are preferably incorporated in a proportion of more than 0 mol % to 90 mol %, more preferably more than 0 mol % to 80 mol %, and even more preferably more than 0 mol % to 75 mol %; recurring units of formula (4) in a proportion of preferably 0 to 90 mol %, more preferably 0 to 80 mol %, and even more preferably 0 to 50 mol %; and recurring units of formula (5) in a proportion of preferably 0 to 90 mol %, more preferably 0 to 80 mol %, and even more preferably 0 to 75 mol %. Recurring units of formula (6) may be incorporated in a proportion of 0 to 75 mol %.

The polymers of the invention are prepared by copolymerization reaction using the compound of formula (1) as a first monomer and polymerizable double bond-bearing compounds (e.g., a compound from which recurring units of formula (3) are derived) as second and subsequent monomers. The copolymerization reaction to produce the inventive polymers may be performed in various modes, preferably radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

Resist Composition

Since the polymer of the invention is useful as the base resin of a resist composition, the other aspect of the invention provides a resist composition comprising the polymer and specifically a chemically amplified positive resist composition comprising the polymer. Typically, the positive resist composition contains (A) the inventive polymer as a base resin, (B) an acid generator, (C) an organic solvent, and optionally (D) a quencher and (E) a surfactant.

In addition to the inventive polymer, the base resin (A) may include another polymer having a dissolution rate in alkaline developer that increases under the action of acid, if necessary. Examples of the other polymer include, but are not limited to, (i) poly(meth)acrylic acid derivatives, (ii) norbornene derivative-maleic anhydride copolymers, (iii) hydrogenated products of ring-opening metathesis polymerization (ROMP) polymers, and (iv) vinyl ether-maleic anhydride-(meth)acrylic acid derivative copolymers.

Of these, the hydrogenated ROMP polymers are synthesized by the method illustrated in JP-A 2003-66612. Illustrative examples of such hydrogenated polymers include those polymers having the recurring units shown below, but are not limited thereto.

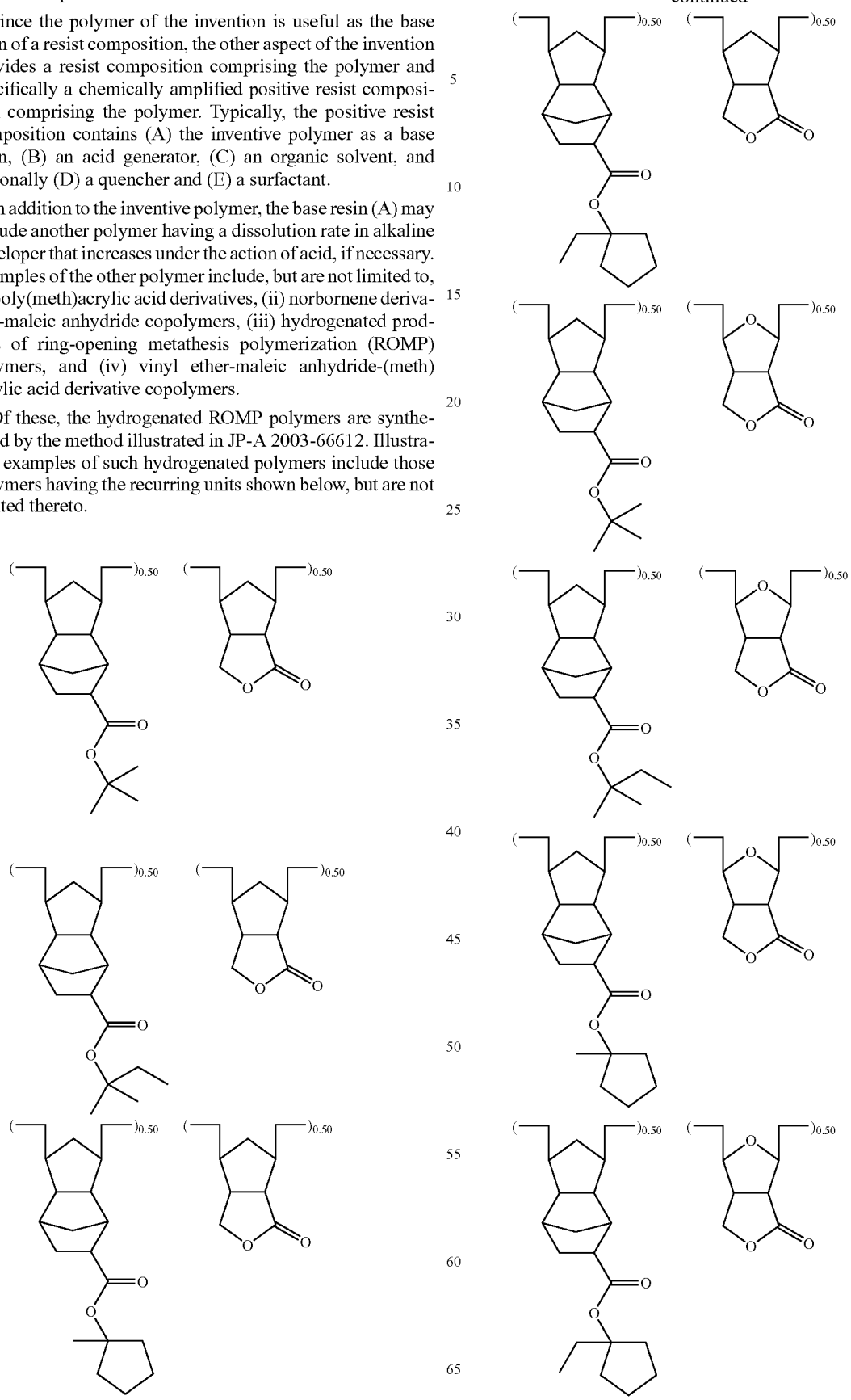

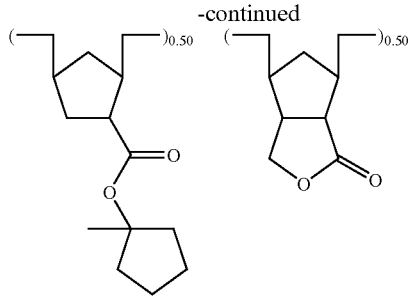
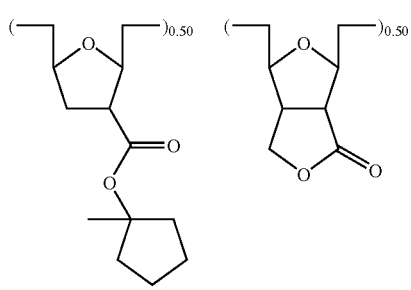
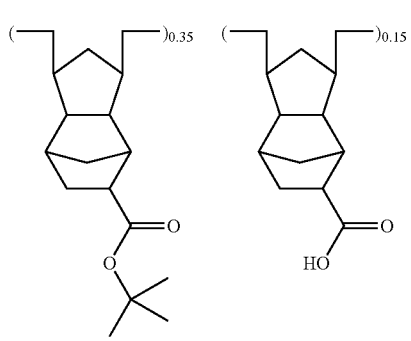
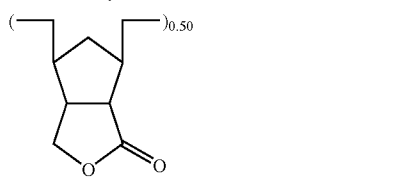
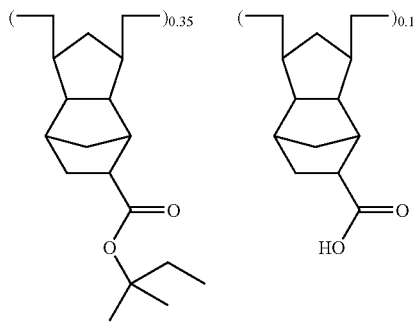
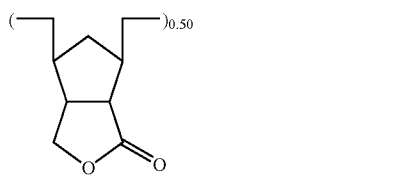
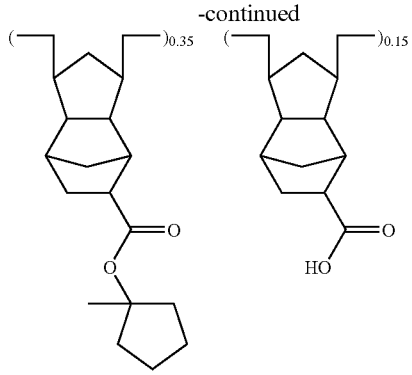
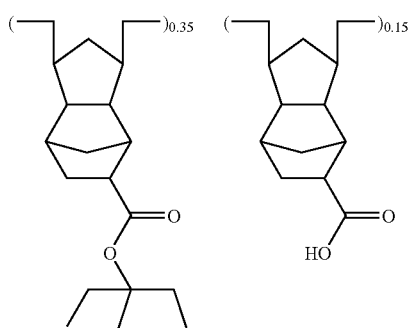
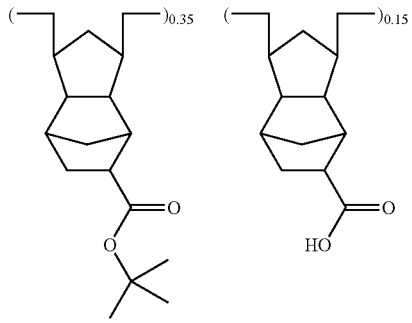

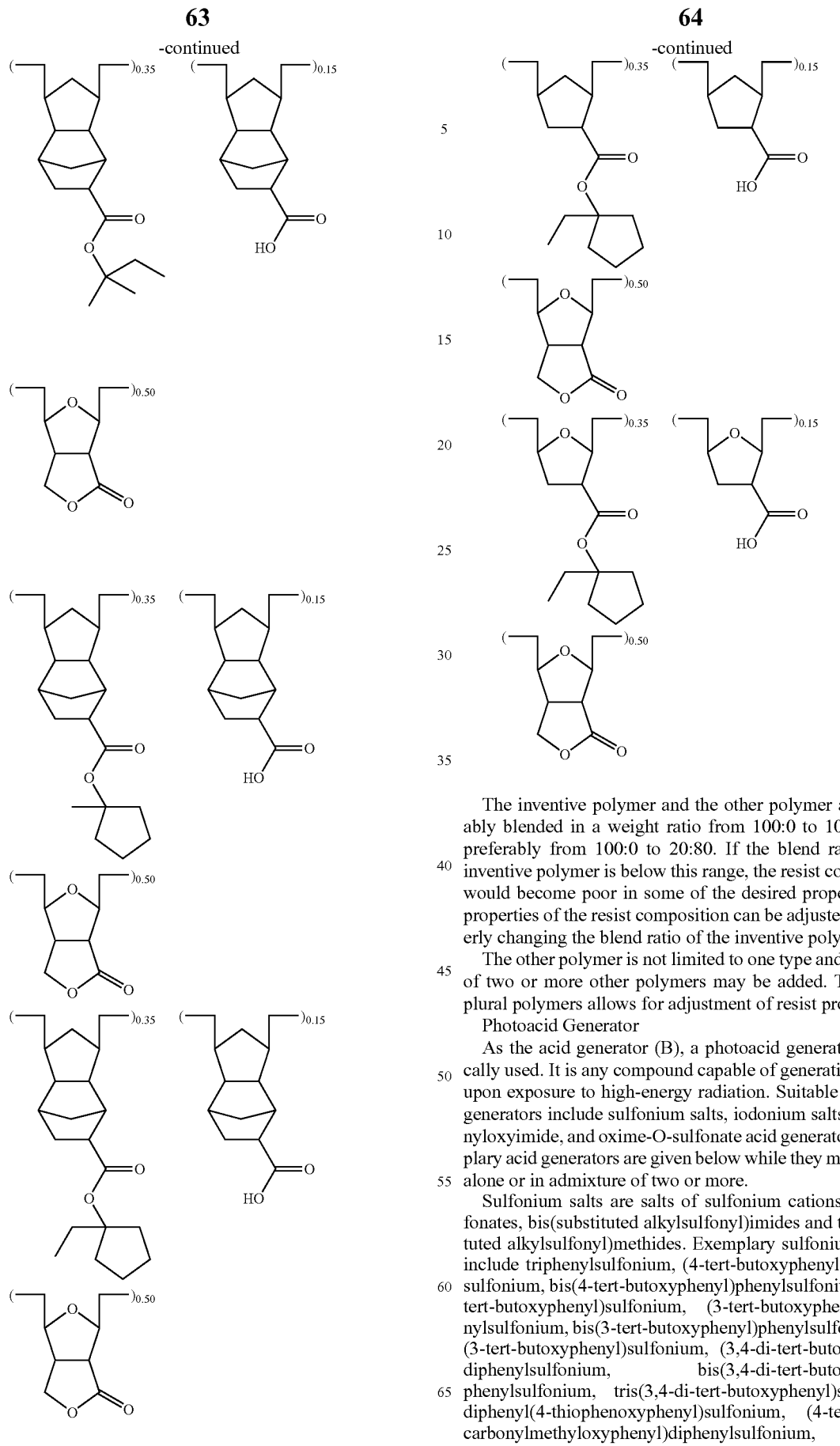

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The other polymer is not limited to one type and a mixture of two or more other polymers may be added. The use of plural polymers allows for adjustment of resist properties.

Photoacid Generator

As the acid generator (B), a photoacid generator is typically used. It is any compound capable of generating an acid upon exposure to high-energy radiation. Suitable photoacid generators include sulfonium salts, iodonium salts, N-sulfonyloxyimide, and oxime-O-sulfonate acid generators. Exemplary acid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tertbutoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenyldiphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium.

Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide.

A typical tris(substituted alkylsulfonyl)methide is tris(trifluoromethylsulfonyl)methide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations include diphenyliodonium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide.

A typical tris(substituted alkylsulfonyl)methide is tris(trifluoromethylsulfonyl)methide. Iodonium salts based on combination of the foregoing examples are included.

N-sulfonyloxydicarboxylmide photoacid generators include combinations of imide skeletons with sulfonates. Exemplary imide skeletons are succinimide, naphthalenedicarboxylmide, phthalimide, cyclohexyldicarboxylmide, 5-norbornene-2,3-dicarboxylmide, and 7-oxabicyclo[2.2.1]-5-heptene-2,3-dicarboxylmide. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxy-carbonyl) difluoromethanesulfonate, and 4-oxo-1-adamantyloxycarbonyldifluoromethanesulfonate.

Suitable oxime sulfonate photoacid generators in the form of O-arylsulfonyloxime and O-alkylsulfonyloxime compounds include oxime sulfonates having an electron withdrawing group such as trifluoromethyl incorporated for increased stability, as represented by the formula (Ox-1).

(Ox-1)

Herein $R^{401}$ is a substituted or unsubstituted $C_1$-$C_{10}$ haloalkylsulfonyl or halobenzenesulfonyl group, $R^{402}$ is a $C_1$-$C_{11}$ haloalkyl group, and $Ar^{401}$ is substituted or unsubstituted aromatic or hetero-aromatic group.

Examples include 2-[2,2,3,3,4,4,5,5-octafluoro-1-(nonafluorobutylsulfonyloxyimino)-pentyl]fluorene, 2-[2,2,3,3,4,4-pentafluoro-1-(nonafluorobutylsulfonyloxyimino)-butyl]fluorene, 2-[2,2,3,3,4,4,5,5,6,6-decafluoro-1-(nonafluorobutylsulfonyloxyimino)-hexyl]fluorene, 2-[2,2,3,3,4,4,5,5-octafluoro-1-(nonafluorobutylsulfonyloxyimino)-pentyl]-4-biphenyl, 2-[2,2,3,3,4,4-pentafluoro-1-(nonafluorobutylsulfonyloxyimino)-butyl]-4-biphenyl, and 2-[2,2,3,3,4,4,5,5,6,6-decafluoro-1-(nonafluorobutylsulfonyloxyimino)-hexyl]-4-biphenyl. Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxy-carbonyl) difluoromethanesulfonate, and 4-oxo-1-adamantyloxycarbonyldifluoromethanesulfonate.

Among others, acid generators having the general formula (A-1) are preferred.

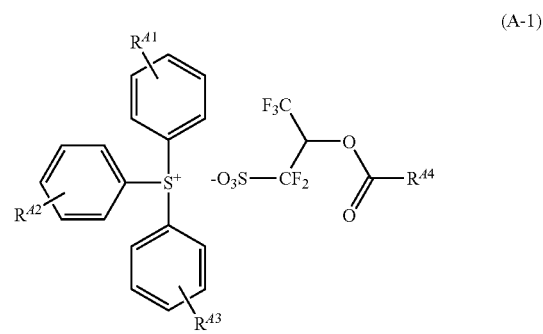

(A-1)

Herein $R^{41}$, $R^{42}$, and $R^{43}$ are each independently hydrogen or a straight, branched or cyclic, monovalent $C_1$-$C_{20}$ hydrocarbon group, typically an alkyl or alkoxy group, which may contain a heteroatom. Examples of hydrocarbon groups optionally containing a heteroatom include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. $R^{44}$ is a straight, branched or cyclic, monovalent $C_7$-$C_{30}$ hydrocarbon group which may contain a heteroatom, examples of which are exemplified below, but are not limited thereto.

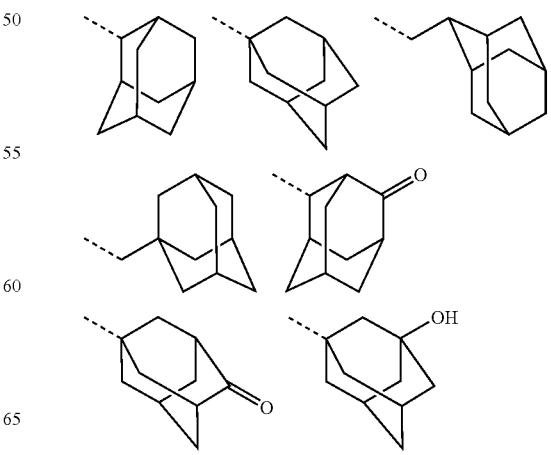

-continued
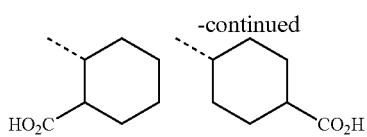
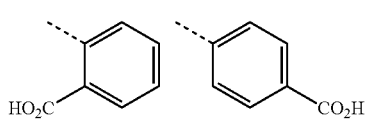
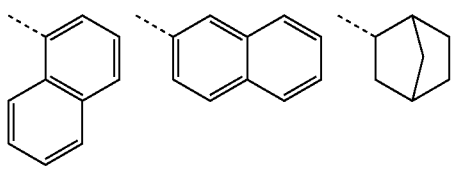
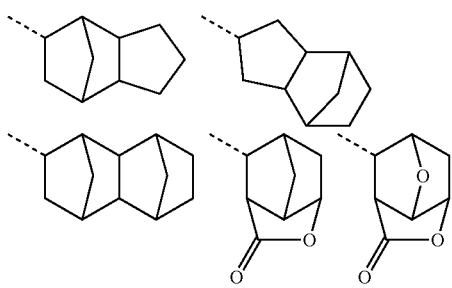
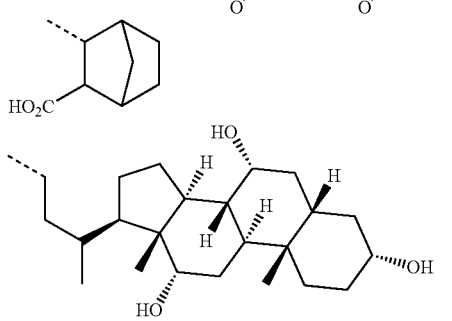
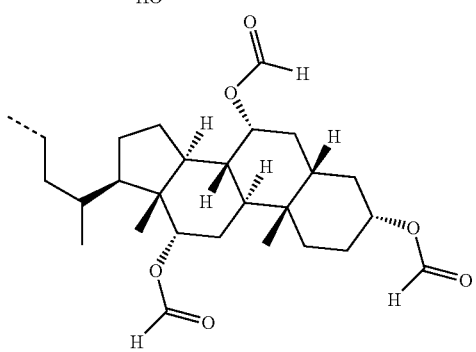
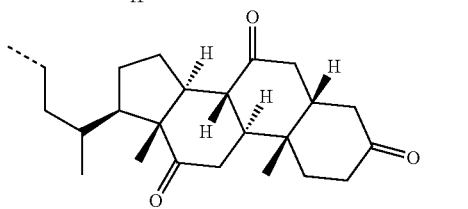
Illustrative examples of acid generators (A-1) are shown below.
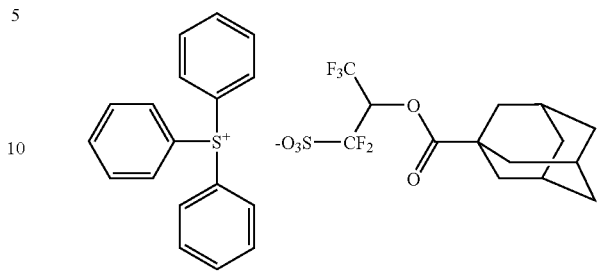
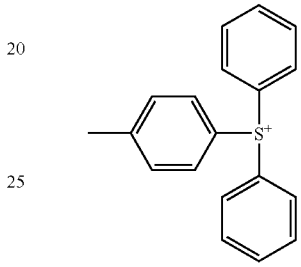
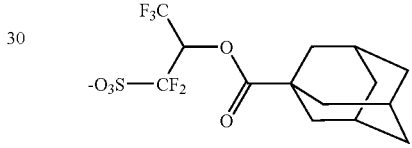
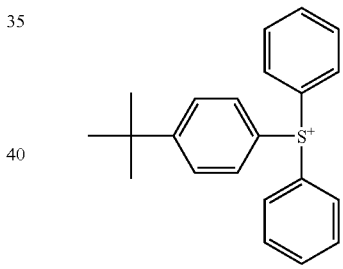
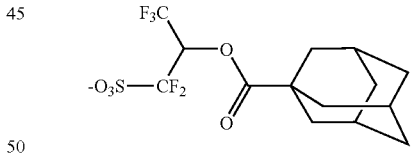
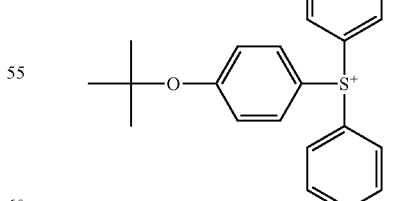
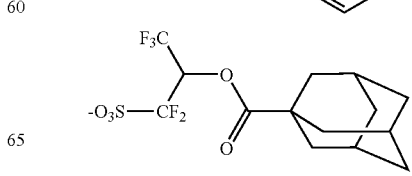

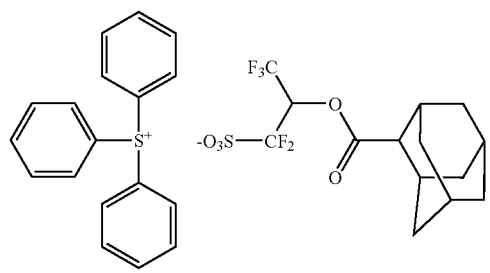
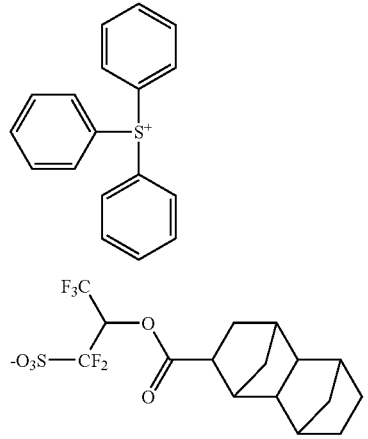
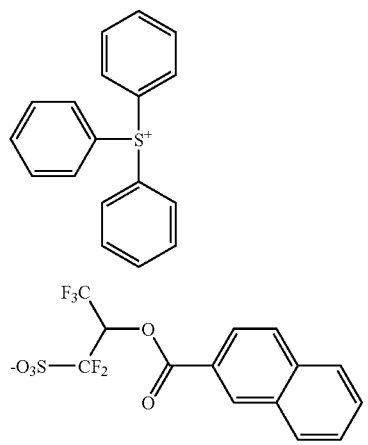
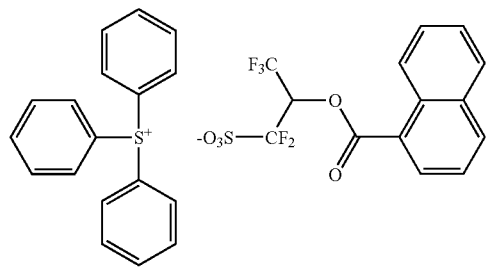
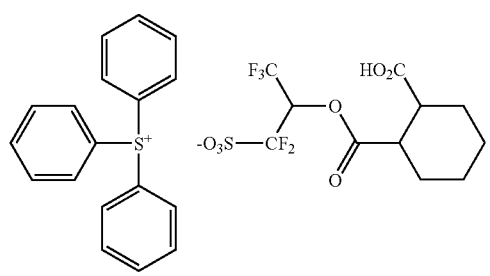
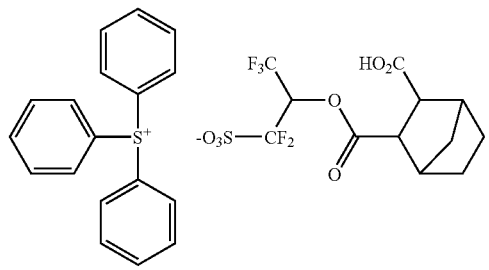
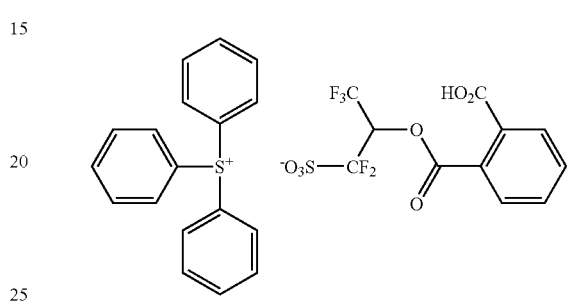
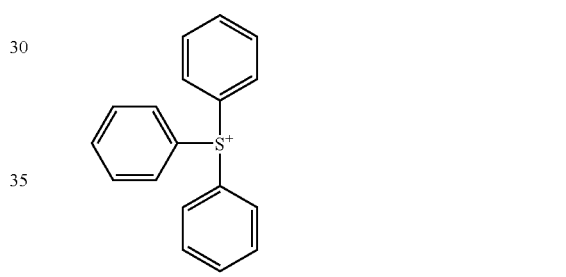
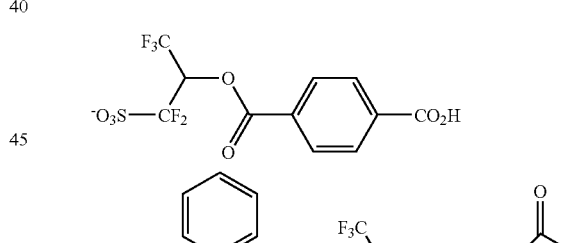
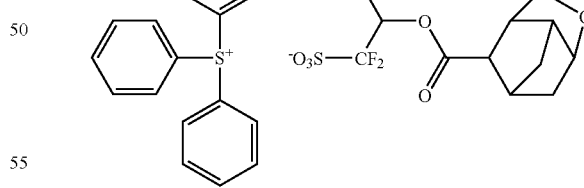
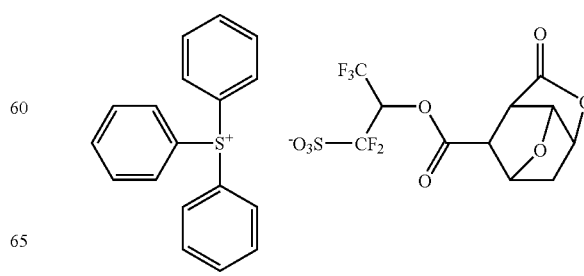

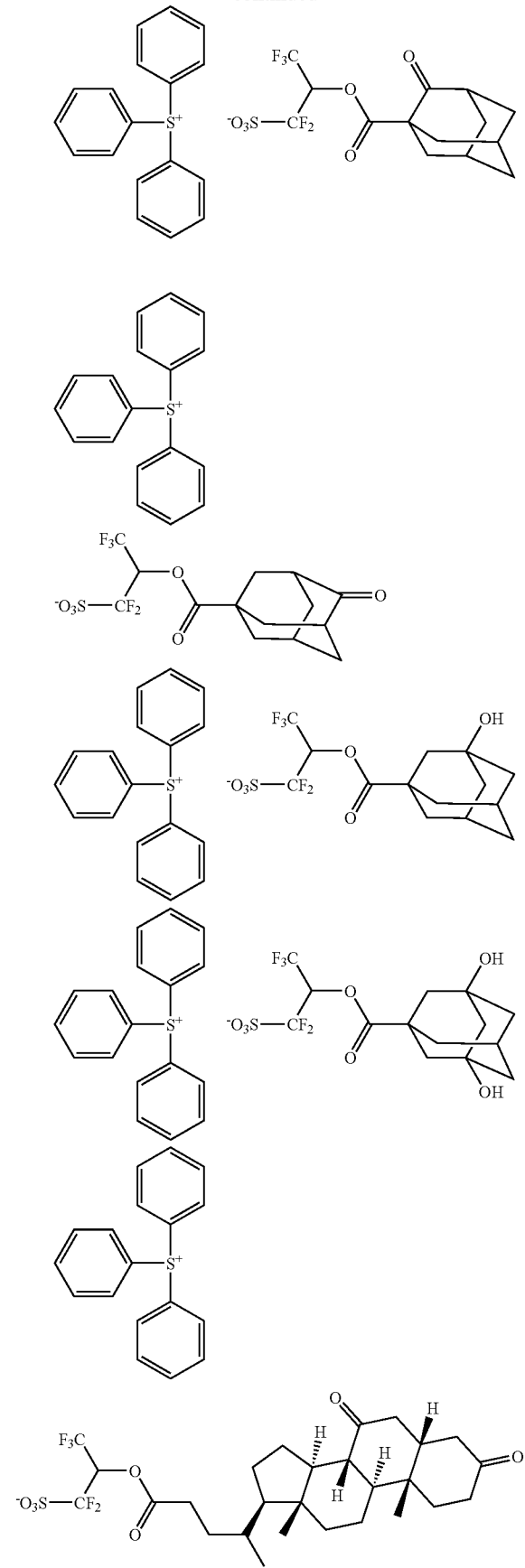

In the chemically amplified resist composition, the photoacid generator (B) may be added in any desired amount as long as the objects of the invention are not compromised. An appropriate amount of the photoacid generator (B) is 0.1 to 10 parts, and more preferably 0.1 to 5 parts by weight per 100 parts by weight of the base resin in the composition. Too high a proportion of the photoacid generator (B) may give rise to problems of degraded resolution and foreign matter upon development and resist film peeling. The photoacid generators may be used alone or in admixture of two or more. The transmittance of the resist film can be controlled by using an photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid is used, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Organic Solvent

The organic solvent (C) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, PGMEA, and mixtures thereof because the acid generator is most soluble therein.

An appropriate amount of the organic solvent used is 200 to 1,000 parts, especially 400 to 800 parts by weight per 100 parts by weight of the base resin.

Quencher

A quencher (D) may be optionally used in the resist composition of the invention. The term "quencher" as used herein has a meaning generally known in the art and refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

In addition, amine compounds of the following general formula (B)-1 are also useful.

$$N(X)_n(Y)_{3-n} \quad \text{(B)-1}$$

In the formula, n is equal to 1, 2 or 3. The side chain X is independently selected from groups of the following general formulas (X)-1 to (X)-3. The side chain Y is independently hydrogen or a straight, branched or cyclic $C_1$-$C_{20}$ alkyl group in which some or all hydrogen atoms may be substituted by fluorine atoms and which may contain an ether or hydroxyl group. Two or three X may bond together to form a ring.

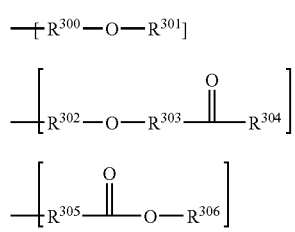

In the formulas, $R^{300}$, $R^{302}$ and $R^{305}$ are independently straight or branched $C_1$-$C_4$ alkylene groups. $R^{301}$ and $R^{304}$ are independently hydrogen or straight, branched or cyclic $C_1$-$C_{50}$ alkyl groups in which some or all hydrogen atoms may be substituted by fluorine atoms and which may contain one or more hydroxyl, ether, ester groups or lactone rings. $R^{303}$ is a single bond or a straight or branched $C_1$-$C_4$ alkylene group. $R^{306}$ is a straight or cyclic $C_1$-$C_{50}$ alkyl group in which some or all hydrogen atoms may be substituted by fluorine atoms and which may contain one or more hydroxyl, ether, ester groups or lactone rings.

Also useful are cyclic structure-bearing amine compounds having the following general formula (B)-2.

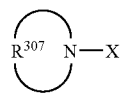

Herein X is as defined above, and $R^{307}$ is a straight or branched $C_2$-$C_{20}$ alkylene group in which some or all hydrogen atoms may be substituted by fluorine atoms and which may contain one or more carbonyl, ether, ester or sulfide groups.

Further, cyano-bearing amine compounds having the following general formulae (B)-3 to (B)-6 may be added.

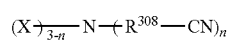

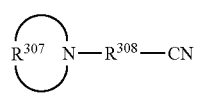

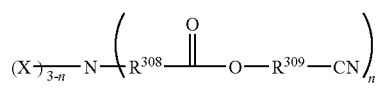

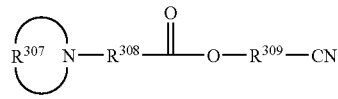

Herein, X, $R^{307}$ and n are as defined in formula (B)-1, and $R^{308}$ and $R^{309}$ are each independently a straight or branched $C_1$-$C_4$ alkylene group.

Also included are amine compounds of imidazole structure having a polar functional group, represented by the general formula (B)-7.

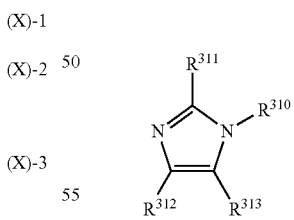

Herein, $R^{310}$ is a straight, branched or cyclic $C_2$-$C_{50}$ alkyl group in which some or all hydrogen atoms may be substituted by fluorine atoms and which has one or more polar functional groups selected from among ester, acetal, cyano, hydroxyl, carbonyl, ether, sulfide, and carbonate groups and mixtures thereof. $R^{311}$, $R^{312}$ and $R^{313}$ are each independently hydrogen, a straight, branched or cyclic $C_1$-$C_{10}$ alkyl group, aryl group or aralkyl group.

Also included are amine compounds of benzimidazole structure having a polar functional group, represented by the general formula (B)-8.

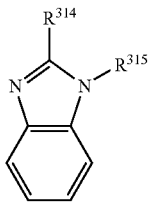
(B)-8

Herein, $R^{314}$ is hydrogen, a straight, branched or cyclic $C_1$-$C_{50}$ alkyl group, aryl group or aralkyl group. $R^{315}$ is a straight, branched or cyclic $C_1$-$C_{50}$ alkyl group in which some or all hydrogen atoms may be substituted by fluorine atoms and which has one or more polar functional groups selected from among ester, acetal, cyano, hydroxyl, carbonyl, ether, sulfide and carbonate groups.

Further included are heterocyclic nitrogen-containing compounds having a polar functional group, represented by the general formulae (B)-9 and (B)-10.

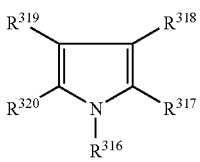
(B)-9

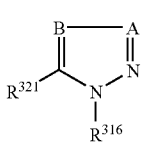
(B)-10

Herein, A is a nitrogen atom or =C—$R^{322}$. B is a nitrogen atom or =C—$R^{323}$. $R^{316}$ is a straight, branched or cyclic $C_2$-$C_{50}$ alkyl group in which some or all hydrogen atoms may be substituted by fluorine atoms and which has one or more polar functional groups, the polar functional group being selected from among ester, acetal, cyano, hydroxyl, carbonyl, ether, sulfide, and carbonate groups and mixtures thereof. $R^{317}$, $R^{318}$, $R^{319}$ and $R^{320}$ are each independently hydrogen, a straight, branched or cyclic $C_1$-$C_{10}$ alkyl group or aryl group, or a pair of $R^{317}$ and $R^{318}$ and a pair of $R^{319}$ and $R^{320}$, taken together, may form a benzene, naphthalene or pyridine ring with the carbon atoms to which they are attached. $R^{321}$ is hydrogen, a straight, branched or cyclic $C_1$-$C_{10}$ alkyl group or aryl group. $R^{322}$ and $R^{323}$ each are hydrogen, a straight, branched or cyclic $C_1$-$C_{10}$ alkyl group or aryl group, or a pair of $R^{321}$ and $R^{323}$, taken together, may form a benzene or naphthalene ring with the carbon atoms to which they are attached.

Also included are amine compounds having an aromatic carboxylate structure, represented by the general formulae (B)-11 to (B)-14.

(B)-11

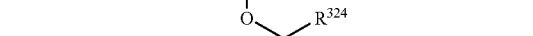
(B)-12

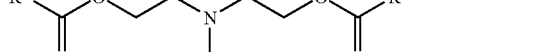
(B)-13

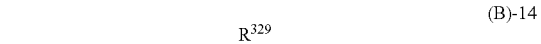
(B)-14

Herein $R^{324}$ is a $C_6$-$C_{20}$ aryl group or $C_4$-$C_{20}$ hetero-aromatic group, in which some or all hydrogen atoms may be replaced by halogen atoms, straight, branched or cyclic $C_1$-$C_{20}$ alkyl, $C_6$-$C_{20}$ aryl, $C_7$-$C_{20}$ aralkyl, $C_1$-$C_{10}$ alkoxy, $C_1$-$C_{10}$ acyloxy or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —$O(CH_2CH_2O)_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring with the carbon atoms to which they are attached.

Further included are amine compounds of 7-oxanorbornane-2-carboxylic ester structure, represented by the general formula (B)-15.

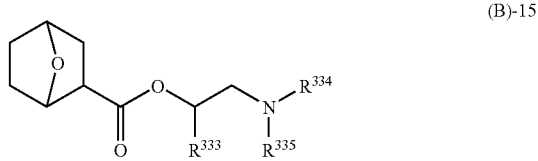
(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms with the nitrogen atom to which they are attached.

Specific examples of the quencher used herein are given below, but not limited thereto.

Examples of suitable primary aliphatic amines include methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, N,N-bis(hydroxyethyl)aniline, 2-methylaniline, 3-methylaniline, 4-methylaniline, ethylaniline, propylaniline, dimethylaniline, 2,6-diisopropylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazane derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds with carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). A typical nitrogen-containing compound with sulfonyl group is 3-pyridinesulfonic acid. Examples of suitable nitrogen-containing compounds with hydroxyl group, nitrogen-containing compounds with hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-tert-butoxycarbonyl-N,N-dicyclohexylamine, N-tert-butoxycarbonylbenzimidazole, and oxazolidinone.

Suitable ammonium salts include pyridinium p-toluenesulfonate, triethylammonium p-toluenesulfonate, trioctylammonium p-toluenesulfonate, triethylammonium 2,4,6-triisopropylbenzenesulfonate, trioctylammonium 2,4,6-triisopropylbenzenesulfonate, triethylammonium camphorsulfonate, trioctylammonium camphorsulfonate, tetramethylammonium hydroxide, tetraethylammonium hydroxide, tetrabutylammonium hydroxide, benzyltrimethylammonium hydroxide, tetramethylammonium p-toluenesulfonate, tetrabutylammonium p-toluenesulfonate, benzyltrimethylammonium p-toluenesulfonate, tetramethylammonium camphorsulfonate, tetrabutylammonium camphorsulfonate, benzyltrimethylammonium camphorsulfonate, tetramethylammonium 2,4,6-triisopropylbenzenesulfonate, tetrabutylammonium 2,4,6-triisopropylbenzenesulfonate, benzyltrimethylammonium 2,4,6-triisopropylbenzenesulfonate, tetramethylammonium acetate, tetrabutylammonium acetate, benzyltrimethylammonium acetate, tetramethylammonium benzoate, tetrabutylammonium benzoate, and benzyltrimethylammonium benzoate.

Further examples of the tertiary amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris (2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, tris(2-benzoyloxyethyl)amine, tris[2-(4-methoxybenzoyloxy)ethyl]amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Further examples include 1-[2-(methoxymethoxy)ethyl]pyrrolidine, 1-[2-(methoxymethoxy)ethyl]piperidine, 4-[2-(methoxymethoxy)ethyl]morpholine, 1-[2-(methoxymethoxy)ethyl]imidazole, 1-[2-(methoxymethoxy)ethyl]benzimidazole, 1-[2-(methoxymethoxy)ethyl]-2-phenylbenzimidazole, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 1-[2-[(2-methoxyethoxy)methoxy]ethyl]imidazole, 1-[2-[(2-methoxyethoxy)methoxy]ethyl]benzimidazole, 1-[2-[(2-methoxyethoxy)methoxy]ethyl]-2-phenylbenzimidazole, 1-[2-[2-[(2-methoxyethoxy)ethoxy]ethyl]pyrrolidine, 1-[2-[2-[(2-methoxyethoxy)ethoxy]ethyl]piperidine, 4-[2-[2-[(2-methoxyethoxy)ethoxy]ethyl]morpholine, 1-[2-[2-[(2-methoxyethoxy)ethoxy]ethyl]imidazole, 1-[2-[2-[(2-methoxyethoxy)ethoxy]ethyl]benzimidazole, 1-[2-[2-[(2-methoxyethoxy)ethoxy]ethyl]-2-phenylbenzimidazole, 1-[2-[2-[(2-butoxyethoxy)ethoxy]ethyl]pyrrolidine, 1-[2-[2-[(2-butoxyethoxy)ethoxy]ethyl]piperidine, 4-[2-[2-[(2-butoxyethoxy)ethoxy]ethyl]morpholine, 1-[2-[2-[(2-butoxyethoxy)ethoxy]ethyl]imidazole, 1-[2-[2-[(2-butoxyethoxy)ethoxy]ethyl]benzimidazole, 1-[2-[2-[(2-butoxyethoxy)ethoxy]ethyl]-2-phenylbenzimidazole, 1-[2-[2-[2-[(2-methoxyethoxy)ethoxy]ethoxy]ethyl]pyrrolidine, 1-[2-[2-[2-[(2-methoxyethoxy)ethoxy]ethoxy]ethyl]piperidine, 4-[2-[2-[2-[(2-methoxyethoxy)ethoxy]ethoxy]ethyl]morpholine, 1-[2-[2-[2-[(2-methoxyethoxy)ethoxy]ethoxy]ethyl]imidazole, 1-[2-[2-[2-[(2-methoxyethoxy)ethoxy]ethoxy]ethyl]-benzimidazole, 1-[2-[2-[2-[(2-methoxyethoxy)ethoxy]ethoxy]ethyl]-2-phenyl-benzimidazole, 4-[2-[2-[2-[(2-butoxyethoxy)ethoxy]ethoxy]ethyl]morpholine, 2-(1-pyrrolidinyl)ethyl acetate, 2-piperidinoethyl acetate, 2-morpholinoethyl acetate, 2-(1-imidazolyl)ethyl acetate, 2-(1-benzimidazoyl)ethyl acetate, 2-(2-phenyl-1-benzimidazolyl)ethyl acetate, 2-methoxyethyl morpholinoacetate, 2-(1-pyrrolidinyl)ethyl 2-methoxyacetate, 2-piperidinoethyl 2-methoxyacetate, 2-morpholinoethyl 2-methoxyacetate, 2-(1-imidazolyl)ethyl 2-methoxyacetate, 2-(1-benzimidazolyl)ethyl 2-methoxyacetate, 2-(2-phenyl-1-benzimidazolyl)ethyl 2-methoxyacetate, 2-(1-pyrrolidinyl)ethyl 2-(2-methoxyethoxy)acetate, 2-piperidinoethyl 2-(2-methoxyethoxy)acetate, 2-morpholinoethyl 2-(2-methoxyethoxy)acetate, 2-(1-imidazolyl)ethyl 2-(2-methoxyethoxy)acetate, 2-(1-benzimidazolyl)ethyl 2-(2-methoxyethoxy)acetate, 2-(2-phenyl-1-benzimidazolyl)ethyl 2-(2-methoxyethoxy)acetate, 2-(1-pyrrolidinyl)ethyl 2-[2-(2-methoxyethoxy)ethoxy]acetate, 2-piperidinoethyl 2-[2-(2-methoxyethoxy)ethoxy]acetate, 2-morpholinoethyl 2-[2-(2-methoxyethoxy)ethoxy]acetate, 2-(1-imidazolyl)ethyl 2-[2-(2-methoxyethoxy)ethoxy]acetate, 2-(1-benzimidazolyl)ethyl 2-[2-(2-methoxyethoxy)ethoxy]-acetate, 2-(2-phenyl-1-benzimidazolyl)ethyl 2-[2-(2-methoxyethoxy)-ethoxy]acetate, 2-morpholinoethyl butyrate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl behenate, 2-morpholinoethyl cholate, 2-morpholinoethyl tris(O-acetyl)cholate, 2-morpholinoethyl tris(O-formyl)cholate, 2-morpholinoethyl dehydrocholate, 2-morpholinoethyl cyclopentanecarboxylate, 2-morpholinoethyl cyclohexanecarboxylate, 2-(1-pyrrolidinyl)ethyl 7-oxanorbornane-2-carboxylate, 2-piperidinoethyl 7-oxanorbornane-2-carboxylate, 2-morpholinoethyl 7-oxanorbornane-2-carboxylate, 2-(1-imidazolyl)ethyl 7-oxanorbornane-2-carboxylate, 2-(1-benzimidazolyl)ethyl 7-oxanorbornane-2-carboxylate, 2-(2-phenyl-1-benzimidazolyl)ethyl 7-oxanorbornane-2-carboxylate, 2-morpholinoethyl adamantanecarboxylate, 2-(1-pyrrolidinyl)ethyl formate, 2-piperidinoethyl propionate, 2-morpholinoethyl acetoxyacetate, 2-(1-pyrrolidinyl)ethyl methoxyacetate, 2-(1-pyrrolidinyl)ethyl benzoate, 2-piperidinoethyl benzoate, 2-morpholinoethyl benzoate, 2-(1-imidazolyl)ethyl benzoate, 2-(1-benzimidazolyl)ethyl benzoate, 2-(2-phenyl-1-benzimidazolyl)ethyl benzoate, 2-(1-pyrrolidinyl)ethyl 4-methoxybenzoate, 2-piperidinoethyl 4-methoxybenzoate, 2-morpholinoethyl 4-methoxybenzoate, 2-(1-imidazolyl)ethyl 4-methoxybenzoate, 2-(1-benzimidazolyl)ethyl 4-methoxybenzoate, 2-(2-phenyl-1-benzimidazolyl)ethyl 4-methoxybenzoate, 2-(1-pyrrolidinyl)ethyl 4-phenylbenzoate, 2-piperidinoethyl 4-phenylbenzoate, 2-morpholinoethyl 4-phenylbenzoate, 2-(1-imidazolyl)ethyl 4-phenylbenzoate, 2-(1-benzimidazolyl)ethyl 4-phenylbenzoate, 2-(2-phenyl-1-benzimidazolyl)ethyl 4-phenylbenzoate, 2-(1-pyrrolidinyl)ethyl 1-naphthalenecarboxylate, 2-piperidinoethyl 1-naphthalenecarboxylate, 2-morpholinoethyl 1-naphthalenecarboxylate, 2-(1-imidazolyl)ethyl 1-naphthalenecarboxylate, 2-(1-benzimidazolyl)ethyl 1-naphthalenecarboxylate, 2-(2-phenyl-1-benzimidazolyl)ethyl 1-naphthalenecarboxylate, 2-(1-pyrrolidinyl)ethyl 2-naphthalenecarboxylate, 2-piperidinoethyl 2-naphthalenecarboxylate, 2-morpholinoethyl 2-naphthalenecarboxylate, 2-(1-imidazolyl)ethyl 2-naphthalenecarboxylate, 2-(1-benzimidazolyl)ethyl 2-naphthalenecarboxylate, 2-(2-phenyl-1-benzimidazolyl)ethyl 2-naphthalenecarboxylate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, and ethyl 1-pyrrolidinylacetate.

Further examples include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate; N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl) aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

The quenchers may be used alone or in admixture of two or more. The quencher is preferably formulated in an amount of 0.001 to 5 parts, and especially 0.01 to 3 parts by weight, per 100 parts by weight of the total base resin. Less than 0.001 phr of the quencher may achieve no addition effect whereas more than 5 phr may lead to too low a sensitivity.

Surfactant

Optionally, the resist composition of the invention may further comprise (E) a surfactant which is commonly used for facilitating the coating operation. The surfactant may be added in conventional amounts so long as this does not compromise the objects of the invention.

Illustrative, non-limiting examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (JEMCO Inc.), Megaface F171, F172, F173, R08, R30, R90 and R94 (DIC Corp.), Fluorad FC-430, FC-431, FC-4430 and FC-4432 (Sumitomo 3M Co., Ltd.), Asahiguard AG710, Surflon S-381, S-382, S-386; SC101, SC102, SC103, SC104, SC105, SC106, Surfynol E1004, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Additional useful surfactants include partially fluorinated oxetane ring-opened polymers having the structural formula (surf-1).

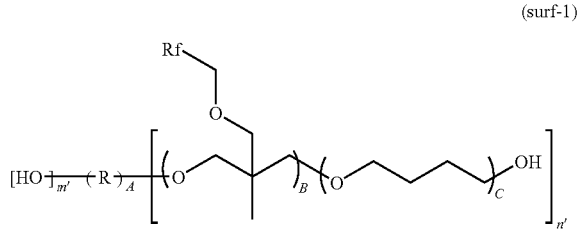

(surf-1)

It is provided herein that R, Rf, A, B, C, m', and n' are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

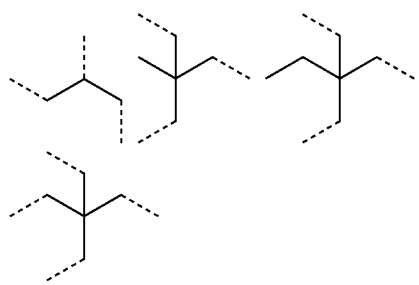

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m' is an integer of 0 to 3, n' is an integer of 1 to 4, and the sum of m' and n', which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430, Surflon S-381, Surfynol E1004, KH-20, KH-30, and oxetane ring-opened polymers of formula (surf-1) are preferred. These surfactants may be used alone or in admixture.

In the resist composition, the surfactant is preferably compounded in an amount of up to 2 parts, and especially up to 1 part by weight, per 100 parts by weight of the base resin. The amount of the surfactant, if added, is preferably at least 0.01 phr.

While the resist composition of the invention typically comprises a polymer or base resin, acid generator, organic solvent and quencher as described above, there may be added optional other ingredients such as dissolution inhibitors, acidic compounds, stabilizers, and dyes. Optional ingredients may be added in conventional amounts so long as this does not compromise the objects of the invention.

Process

Pattern formation using the resist composition of the invention may be carried out by a known lithographic technique. For example, the resist composition is applied onto a substrate such as a silicon wafer by spin coating or the like so as to form a resist film having a thickness of 0.05 to 2.0 μm, which is then pre-baked on a hot plate at 60 to 150° C. for 1 to 10 minutes, and preferably at 80 to 140° C. for 1 to 5 minutes. A patterning mask having the desired pattern is then placed over the resist film, and the film exposed through the mask to an electron beam or to high-energy radiation such as deep-UV, excimer laser, or x-ray in a dose of 1 to 200 mJ/cm$^2$, and preferably 10 to 100 mJ/cm$^2$. Light exposure may be done by a conventional exposure process or in some cases, by an immersion process of providing liquid impregnation between the mask and the resist. The resist film is then post-exposure baked (PEB) on a hot plate at 60 to 150° C. for 1 to 5 minutes, and preferably at 80 to 140° C. for 1 to 3 minutes. Finally, development is carried out using as the developer an aqueous alkali solution, such as a 0.1 to 5 wt % (preferably 2 to 3 wt %) aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV having a wavelength of 250 to 190 nm, excimer laser, x-ray, or an electron beam. The desired pattern may not be obtainable outside the upper and lower limits of the above range.

EXAMPLE

Examples and Comparative Examples are given below by way of illustration and not by way of limitation. The abbreviation "Mw" is a weight average molecular weight as measured by GPC using polystyrene standards, and "pbw" is parts by weight.

Example 1

Lactone compounds within the scope of the invention were synthesized according to the following formulation.

Example 1-1

Synthesis of Monomer 1

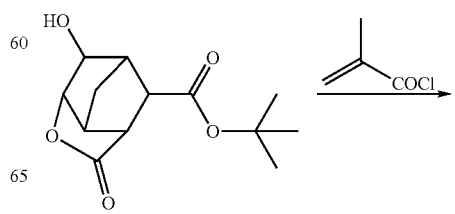

-continued

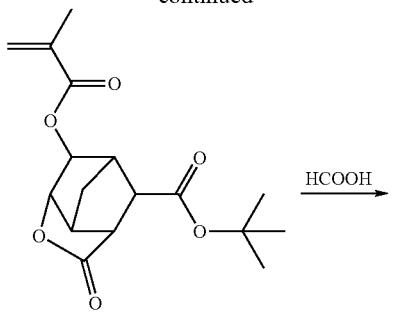

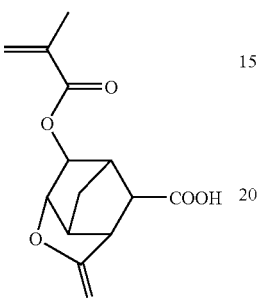

Example 1-1-1

Synthesis of tert-butyl 6-methacryloyl-2-oxohexahydro-3,5-methano-2H-cyclopenta[b]furan-7-carboxylate In 2,500 ml of acetonitrile were dissolved 500 g of tert-butyl 6-hydroxy-2-oxohexahydro-3,5-methano-2H-cyclopenta[b]furan-7-carboxylate and 318 g of triethylamine. To the solution below 15° C., 288 g of methacrylic chloride was added dropwise. The solution was stirred at room temperature for 2 hours, another 32 g of methacrylic chloride added, and the solution stirred overnight. A saturated aqueous solution of sodium hydrogen carbonate, 500 ml, was added to the reaction solution, followed by ordinary work-up. Recrystallization from hexane yielded 437 g of the title compound (yield 69%).

$^1$H-NMR (600 MHz in CDCl$_3$): δ=1.44 (9H, s), 1.78 (1H, d), 1.92 (1H, d), 1.94 (3H, t), 2.68 (1H, s), 2.84 (1H, s), 3.07 (1H, d), 3.21 (1H, m), 4.56 (1H, d), 4.67 (1H, s), 5.61 (1H, t), 6.10 (1H, s) ppm

Example 1-1-2

Synthesis of 6-methacryloyl-2-oxohexahydro-3,5-methano-2H-cyclopenta[b]furan-7-carboxylic acid In 80 g of formic acid was dissolved 20.0 g of the methacrylate obtained in Example 1-1-1. The solution was stirred at room temperature overnight. Toluene was added to the reaction solution, from which formic acid and tert-butyl formate were azeotroped off. Recrystallization from hexane yielded 14.7 g of the target compound (yield 89%).

IR (thin film): ν=3428, 2989, 1789, 1716, 1635, 1307, 1180, 1110, 1022, 931, 817, 717 cm$^{-1}$ $^1$H-NMR (600 MHz in DMSO-d$_6$): δ=1.58 (1H, d), 1.86 (1H, d), 1.88 (3H, t), 2.75 (1H, s), 2.88 (1H, d), 2.91 (1H, s), 3.24 (1H, t), 4.60 (1H, d), 4.63 (1H, s), 5.71 (1H, m), 6.06 (1H, d), 12.9 (1H, s) ppm

Example 1-2

Synthesis of Monomer 2

Example 1-2-1

Synthesis of tert-butyl 6-acryloyl-2-oxohexahydro-3,5-methano-2H-cyclopenta[b]furan-7-carboxylate The title compound was obtained by the same procedure as in Example 1-1-1 aside from using acrylic chloride instead of methacrylic chloride. Yield 84%.

$^1$H-NMR (600 MHz in DMSO-d$_6$): δ=1.41 (9H, s), 1.52 (1H, d), 1.86 (1H, d), 2.74 (1H, s), 2.87 (1H, d), 2.94 (1H, s), 3.24 (1H, t), 4.60 (1H, d), 4.67 (1H, s), 5.99 (1H, d), 6.17 (1H, dd), 6.37 (1H, d) ppm

Example 1-2-2

Synthesis of 6-acryloyl-2-oxohexahydro-3,5-methano-2H-cyclopenta[b]furan-7-carboxylic acid The target compound was obtained by the same procedure as in Example 1-1-2 aside from using tert-butyl 6-acryloyl-2-oxohexahydro-3,5-methano-2H-cyclopenta[b]furan-7-carboxylate instead of tert-butyl 6-methacryloyl-2-oxohexahydro-3,5-methano-2H-cyclopenta[b]furan-7-carboxylate. Yield 91%.

IR (thin film): ν=3428, 2985, 1791, 1724, 1633, 1407, 1299, 1270, 1180, 1112, 1012, 802 cm$^{-1}$ $^1$H-NMR (600 MHz in DMSO-d$_6$): δ=1.58 (1H, d), 1.85 (1H, d), 2.75 (1H, s), 2.88 (1H, d), 2.91 (1H, s), 3.23 (1H, m), 4.60 (1H, d), 4.65 (1H, s), 5.98 (1H, m), 6.17 (1H, dd), 6.37 (1H, d), 13.0 (1H, s) ppm

Example 1-3

Synthesis of Monomer 3

6-Methacryloyl-2-oxo-4-oxahexahydro-3,5-methano-2H-cyclopenta[b]furan-7-carboxylic acid was obtained by following the same procedure as in Examples 1-1-1 and 1-1-2 aside from using tert-butyl 6-hydroxy-2-oxo-4-oxahexahydro-3,5-methano-2H-cyclopenta[b]furan-7-carboxylate instead of tert-butyl 6-hydroxy-2-oxohexahydro-3,5-methano-2H-cyclopenta[b]furan-7-carboxylate. Two-step yield 61%.

Example 1-4

Synthesis of Monomer 4

6-Acryloyl-2-oxo-4-oxahexahydro-3,5-methano-2H-cyclopenta[b]furan-7-carboxylic acid was obtained by following the same procedure as in Examples 1-1-1 and 1-1-2 aside from using tert-butyl 6-hydroxy-2-oxo-4-oxahexahydro-3,5-methano-2H-cyclopenta[b]furan-7-carboxylate instead of tert-butyl 6-hydroxy-2-oxohexahydro-3,5-methano-2H-cyclopenta[b]furan-7-carboxylate and acrylic chloride instead of methacrylic chloride. Two-step yield 75%.

Example 1-5

Synthesis of Monomer 5

6-[2-(Trifluoromethyl)]acryloyl-2-oxohexahydro-3,5-methano-2H-cyclopenta[b]furan-7-carboxylic acid was obtained by following the same procedure as in Examples 1-1-1 and 1-1-2 aside from using 2-(trifluoromethyl)acrylic chloride instead of methacrylic chloride. Two-step yield 63%.

Example 1-6

Synthesis of Monomer 6

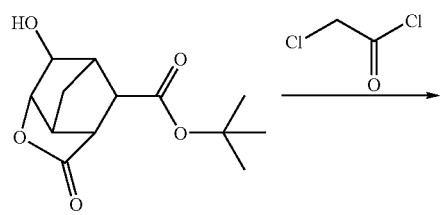

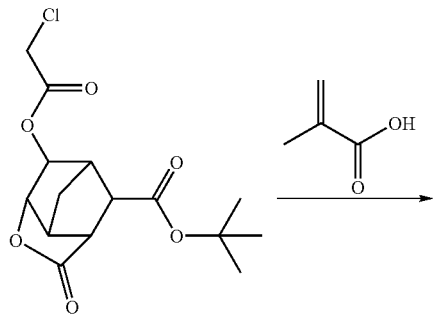

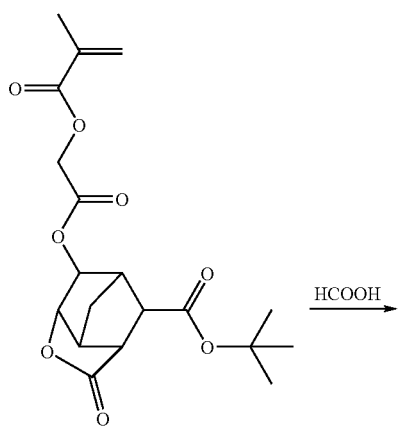

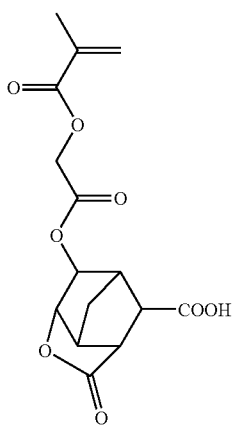

Example 1-6-1

Synthesis of 7-tert-butoxycarbonyl-2-oxohexahydro-3,5-methano-2H-cyclopenta[b]furan-6-yl 2-chloroacetate In 1,000 ml of tetrahydrofuran were dissolved 163 g of tert-butyl 6-hydroxy-2-oxohexahydro-3,5-methano-2H-cyclopenta[b]furan-7-carboxylate and 86.9 g of 2-chloroacetic chloride. To this solution below 15° C., 58.3 g of pyridine was added dropwise. The reaction solution was stirred at room temperature for 2 hours, whereupon 250 ml of deionized water was added, followed by ordinary workup. Recrystallization from hexane yielded 200 g of the title compound. Yield 94%.

$^1$H-NMR (600 MHz in DMSO-$d_6$): δ=1.45 (9H, s), 1.79 (1H, d), 1.92 (1H, d), 2.68 (1H, s), 2.86 (1H, s), 3.08 (1H, d), 3.23 (1H, m), 4.07 (2H, s), 4.57 (1H, d), 4.70 (1H, s) ppm

Example 1-6-2

Synthesis of 7-tert-butoxycarbonyl-2-oxohexahydro-3,5-methano-2H-cyclopenta[b]furan-6-yl 2-(methacryloyloxy)-acetate In 800 ml of dimethylformamide were dissolved 199 g of the 2-chloroacetate obtained in Example 1-6-1, 64.8 g of methacrylic acid, and 4.50 g of sodium iodide. To the solution below 30° C., 73.1 g of triethylamine was added dropwise. The reaction solution was stirred at the temperature overnight, whereupon 500 ml of deionized water below 30° C. was added, followed by ordinary workup. Recrystallization from hexane yielded 209 g of the title compound. Yield 91%.

$^1$H-NMR (600 MHz in DMSO-$d_6$): δ=1.41 (9H, s), 1.52 (1H, d), 1.78 (1H, d), 1.91 (1H, t), 2.71 (1H, d), 2.86 (1H, d), 2.95 (1H, s), 3.25 (1H, m), 4.55 (1H, d), 4.69 (1H, s), 4.77 (2H, d), 5.79 (1H, m), 6.12 (1H, s) ppm

Example 1-6-3

Synthesis of 6-[2-(methacryloyloxy)acetic acid]-2-oxohexahydro-3,5-methano-2H-cyclopenta[b]furan-7-carboxylic acid In 830 g of formic acid was dissolved 206 g of the methacrylate obtained in Example 1-6-2. The solution was stirred at room temperature overnight. Toluene was added to the reaction solution, from which formic acid and tert-butyl formate were azeotroped off. Recrystallization from hexane yielded 170 g of the target compound (yield 96%).

IR (thin film): ν=3421, 3187, 1764, 1718, 1637, 1396, 1363, 1309, 1249, 1191, 1118, 1066, 1000, 941, 813 cm$^{-1}$ $^1$H-NMR (600 MHz in DMSO-d$_6$): δ=1.55 (1H, d), 1.78 (1H, d), 1.96 (3H, t), 2.72 (1H, s), 2.87 (1H, dd), 2.94 (1H, d), 3.24 (1H, m), 4.55 (1H, d), 4.67 (1H, s), 4.77 (2H, d), 5.79 (1H, m), 6.12 (1H, t), 13.96 (1H, s) ppm Example 1-7

Synthesis of Monomer 7

The procedure of Examples 1-6-1, 1-6-2 and 1-6-3 was repeated aside from using acrylic acid instead of methacrylic acid. There was obtained 6-[2-(acryloyloxy)acetic acid]-2-oxohexahydro-3,5-methano-2H-cyclopenta[b]furan-7-carboxylic acid. Three-step yield 84%.

Example 1-8

Synthesis of Monomer 8

The procedure of Examples 1-6-1, 1-6-2 and 1-6-3 was repeated aside from using tert-butyl 6-hydroxy-2-oxo-4-oxahexahydro-3,5-methano-2H-cyclopenta[b]furan-7-carboxylate instead of tert-butyl 6-hydroxy-2-oxohexahydro-3,5-methano-2H-cyclopenta[b]furan-7-carboxylate. There was obtained 6-[2-(methacryloyloxy)acetic acid]-2-oxo-4-oxahexahydro-3,5-methano-2H-cyclopenta[b]furan-7-carboxylic acid. Three-step yield 82%.

Example 1-9

Synthesis of Monomer 9

The procedure of Examples 1-6-1, 1-6-2 and 1-6-3 was repeated aside from using tert-butyl 6-hydroxy-2-oxo-4-oxahexahydro-3,5-methano-2H-cyclopenta[b]furan-7-carboxylate instead of tert-butyl 6-hydroxy-2-oxohexahydro-3,5-methano-2H-cyclopenta[b]furan-7-carboxylate, and acrylic acid instead of methacrylic acid. There was obtained 6-[2-(acryloyloxy)-acetic acid]-2-oxo-4-oxahexahydro-3,5-methano-2H-cyclopenta-[b]furan-7-carboxylic acid. Three-step yield 83%.

Example 1-10

Synthesis of Monomer 10

The procedure of Examples 1-6-1, 1-6-2 and 1-6-3 was repeated aside from using 2-(trifluoromethyl)acrylic acid instead of methacrylic acid. There was obtained 6-[2-(2-(trifluoromethyl)acryloyloxy)acetic acid]-2-oxohexahydro-3,5-methano-2H-cyclopenta[b]furan-7-carboxylic acid. Three-step yield 85%.

Example 1-11

Synthesis of Monomer 11

The procedure of Examples 1-6-1, 1-6-2 and 1-6-3 was repeated aside from using 3-chloropropionic chloride instead of 2-chloroacetic chloride. There was obtained 6-[3-(methacryloyloxy)propionic acid]-2-oxohexahydro-3,5-methano-2H-cyclopenta[b]furan-7-carboxylic acid. Three-step yield 79%.

Example 1-12

Synthesis of Monomer 12

The procedure of Examples 1-6-1, 1-6-2 and 1-6-3 was repeated aside from using 3-chloropropionic chloride instead of 2-chloroacetic chloride and acrylic acid instead of methacrylic acid. There was obtained 6-[3-(acryloyloxy)-propionic acid]-2-oxohexahydro-3,5-methano-2H-cyclopenta-[b]furan-7-carboxylic acid. Three-step yield 81%.

Example 1-13

Synthesis of Monomer 13

The procedure of Examples 1-6-1, 1-6-2 and 1-6-3 was repeated aside from using tert-butyl 6-hydroxy-2-oxo-4-oxahexahydro-3,5-methano-2H-cyclopenta[b]furan-7-carboxylate instead of tert-butyl 6-hydroxy-2-oxohexahydro-3,5-methano-2H-cyclopenta[b]furan-7-carboxylate, and 3-chloropropionic chloride instead of 2-chloroacetic chloride. There was obtained 6-[3-(methacryloyloxy)propionic acid]-2-oxo-4-oxahexahydro-3,5-methano-2H-cyclopenta[b]furan-7-carboxylic acid. Three-step yield 83%.

Example 1-14

Synthesis of Monomer 14

The procedure of Examples 1-6-1, 1-6-2 and 1-6-3 was repeated aside from using tert-butyl 6-hydroxy-2-oxo-4-oxahexahydro-3,5-methano-2H-cyclopenta[b]furan-7-carboxylate instead of tert-butyl 6-hydroxy-2-oxohexahydro-3,5-methano-2H-cyclopenta[b]furan-7-carboxylate, 3-chloropropionic chloride instead of 2-chloroacetic chloride, and acrylic acid instead of methacrylic acid. There was obtained 6-[3-(acryloyloxy)propionic acid]-2-oxo-4-oxahexahydro-3,5-methano-2H-cyclopenta[b]furan-7-carboxylic acid. Three-step yield 78%.

Example 1-15

Synthesis of Monomer 15

The procedure of Examples 1-6-1, 1-6-2 and 1-6-3 was repeated aside from using tert-butyl 6-hydroxy-2-oxo-4-oxahexahydro-3,5-methano-2H-cyclopenta[b]furan-7-carboxylate instead of tert-butyl 6-hydroxy-2-oxohexahydro-3,5-methano-2H-cyclopenta[b]furan-7-carboxylate, 3-chloropropionic chloride instead of 2-chloroacetic chloride, and 2-(trifluoromethyl)acrylic acid instead of methacrylic acid. There was obtained 6-[3-(2-(trifluoromethyl)acryloyloxy)-propionic acid]-2-oxo-4-oxahexahydro-3,5-methano-2H-cyclopenta[b]furan-7-carboxylic acid. Three-step yield 75%.

Example 1-16

Synthesis of Monomer 16

Example 1-16-1

Synthesis of 7-tert-butoxycarbonyl-2-oxohexahydro-3,5-methano-2H-cyclopenta[b]furan-6-yl 4-chlorobutyrate The title compound was obtained by the same procedure as in Example 1-6-1 aside from using 4-chlorobutyric chloride instead of 2-chloroacetic chloride. Yield 90%.

$^1$H-NMR (600 MHz in DMSO-d$_6$): δ=1.41 (9H, s), 1.51 (1H, d), 1.82 (1H, d), 1.98 (2H, m), 2.47 (2H, t), 2.70 (1H, s), 2.85 (1H, d), 2.90 (1H, s), 3.22 (1H, m), 3.66 (1H, t), 4.58 (1H, d), 4.59 (1H, s) ppm Example 1-16-2

Synthesis of 7-tert-butoxycarbonyl-2-oxohexahydro-3,5-methano-2H-cyclopenta[b]furan-6-yl 4-(methacryloyloxy)-butyrate The title compound was obtained by the same procedure as in Example 1-6-2 aside from using 7-tert-butoxycarbonyl-2-oxohexahydro-3,5-methano-2H-cyclopenta[b]furan-6-yl 4-chloro-butyrate instead of 7-tert-butoxycarbonyl-2-oxohexahydro-3,5-methano-2H-cyclopenta[b]furan-6-yl 2-chloroacetate. Yield 95%.

$^1$H-NMR (600 MHz in DMSO-d$_6$): δ=1.41 (9H, s), 1.50 (1H, d), 1.80 (1H, d), 1.87 (3H, m), 1.89 (2H, m), 2.42 (2H, t), 2.68 (1H, s), 2.85 (1H, d), 2.90 (1H, s), 3.22 (1H, m), 4.11 (2H, m), 4.57 (1H, d), 4.58 (1H, s), 5.67 (1H, m), 6.01 (1H, s) ppm Example 1-16-3

Synthesis of 6-[4-(methacryloyloxy)butyric acid]-2-oxohexahydro-3,5-methano-2H-cyclopenta[b]furan-7-carboxylic acid The target compound was obtained by the same procedure as in Example 1-6-3 aside from using 7-tert-butoxycarbonyl-2-oxohexahydro-3,5-methano-2H-cyclopenta[b]furan-6-yl 4-(methacryloyloxy)butyrate instead of 7-tert-butoxycarbonyl-2-oxohexahydro-3,5-methano-2H-cyclopenta[b]furan-6-yl 2-(methacryloyloxy)acetate. Yield 90%.

IR (thin film): ν=3421, 3187, 1764, 1718, 1637, 1396, 1363, 1309, 1249, 1191, 1118, 1066, 1000, 941, 813 cm$^{-1}$ $^1$H-NMR (600 MHz in DMSO-d$_6$): δ=1.54 (1H, d), 1.80 (1H, d), 1.86 (3H, s), 1.89 (2H, m), 2.42 (2H, t), 2.70 (1H, s), 2.87 (1H, d), 2.89 (1H, s), 3.21 (1H, t), 4.11 (2H, m), 4.56 (2H, d), 5.67 (1H, m), 6.01 (1H, s), 12.93 (1H, s) ppm Example 1-17

Synthesis of Monomer 17

The procedure of Examples 1-6-1, 1-6-2 and 1-6-3 was repeated aside from using 4-chlorobutyric chloride instead of 2-chloroacetic chloride. There was obtained 6-[4-(acryloyloxy)butyric acid]-2-oxohexahydro-3,5-methano-2H-cyclopenta-[b]furan-7-carboxylic acid. Three-step yield 73%.

Example 1-18

Synthesis of Monomer 18

The Procedure of Examples 1-6-1, 1-6-2 and 1-6-3 was repeated aside from using tert-butyl 6-hydroxy-2-oxo-4-oxa-hexahydro-3,5-methano-2H-cyclopenta[b]furan-7-carboxylate instead of tert-butyl 6-hydroxy-2-oxohexahydro-3,5-methano-2H-cyclopenta[b]furan-7-carboxylate, and 4-chlorobutyric chloride instead of 2-chloroacetic chloride. There was obtained 6-[4-(methacryloyloxy)butyric acid]-2-oxo-4-oxahexahydro-3,5-methano-2H-cyclopenta[b]furan-7-carboxylic acid. Three-step yield 71%.

Example 1-19

Synthesis of Monomer 19

The procedure of Examples 1-6-1, 1-6-2 and 1-6-3 was repeated aside from using tert-butyl 6-hydroxy-2-oxo-4-oxa-hexahydro-3,5-methano-2H-cyclopenta[b]furan-7-carboxylate instead of tert-butyl 6-hydroxy-2-oxohexahydro-3,5-methano-2H-cyclopenta[b]furan-7-carboxylate, 4-chlorobutyric chloride instead of 2-chloroacetic chloride, and acrylic acid instead of methacrylic acid. There was obtained 6-[4-(acryloyloxy)-butyric acid]-2-oxo-4-oxa-hexahydro-3,5-methano-2H-cyclopenta-[b]furan-7-carboxylic acid. Three-step yield 74%.

Example 1-20

Synthesis of Monomer 20

The procedure of Examples 1-6-1, 1-6-2 and 1-6-3 was repeated aside from using tert-butyl 6-hydroxy-2-oxo-4-oxa-hexahydro-3,5-methano-2H-cyclopenta[b]furan-7-carboxylate instead of tert-butyl 6-hydroxy-2-oxohexahydro-3,5-methano-2H-cyclopenta[b]furan-7-carboxylate, 4-chlorobutyric chloride instead of 2-chloroacetic chloride, and 2-(trifluoromethyl)-acrylic acid instead of methacrylic acid. There was obtained 6-[4-(2-(trifluoromethyl)acryloyloxy)butyric acid]-2-oxo-4-oxahexahydro-3,5-methano-2H-cyclopenta[b]furan-7-carboxylic acid. Three-step yield 72%.

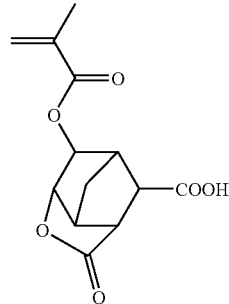

Monomer 1

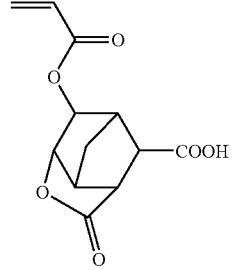

Monomer 2

Monomer 3
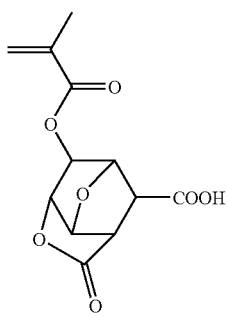
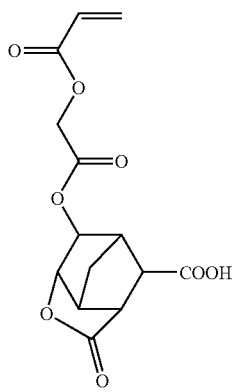
Monomer 7
Monomer 4
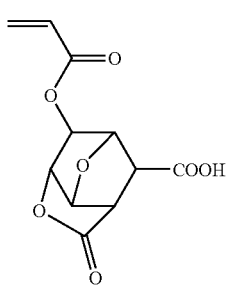
Monomer 8
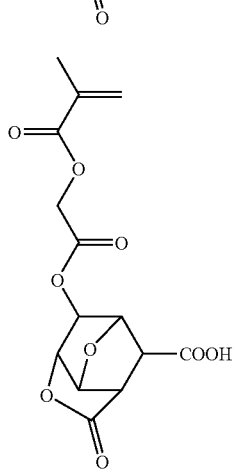
Monomer 5
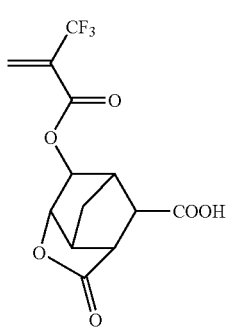
Monomer 9
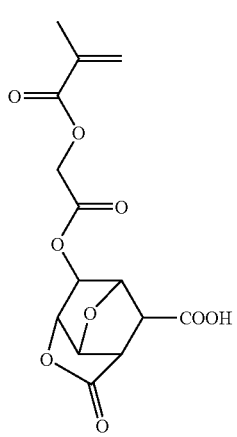
Monomer 6
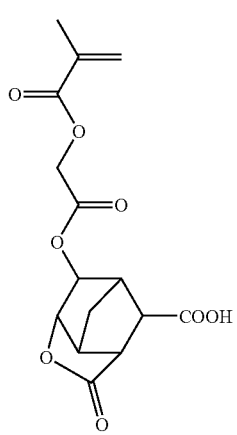
Monomer 10
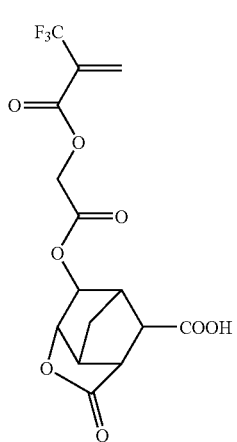

Monomer 11
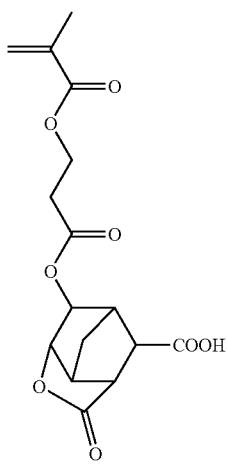
Monomer 12
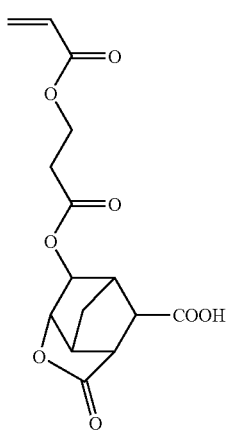
Monomer 13
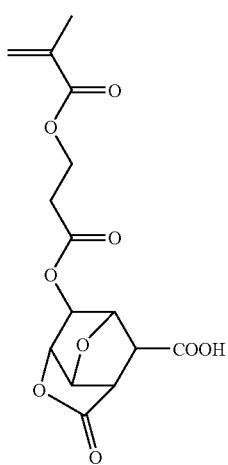
Monomer 14
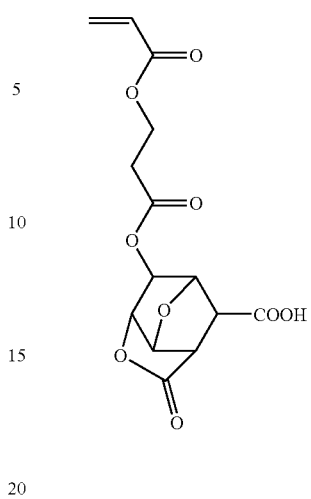
Monomer 15
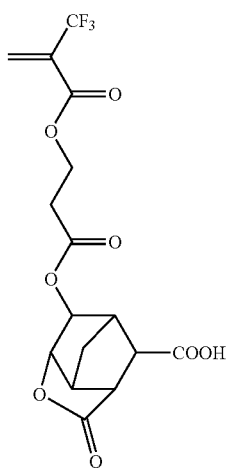
Monomer 16
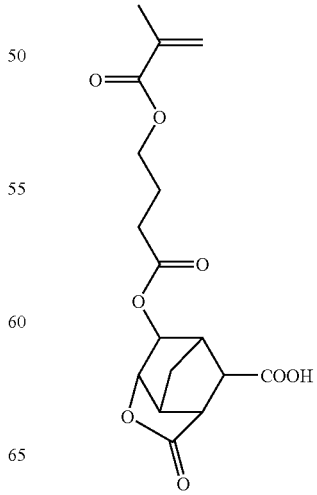

Monomer 17

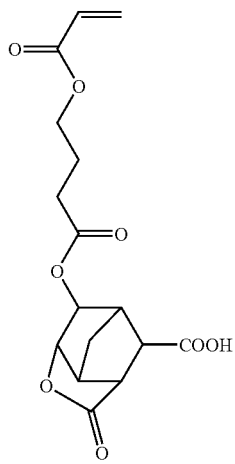

Monomer 18

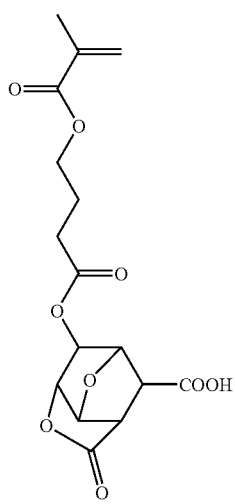

Monomer 19

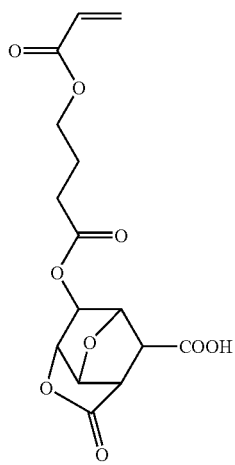

Monomer 20

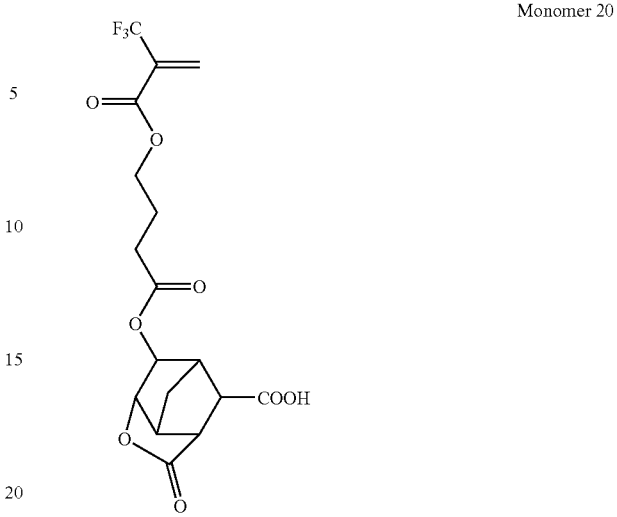

Example 2

Polymers within the scope of the invention were synthesized according to the following formulation.

Example 2-1

Synthesis of Polymer 1

In 750 g of tetrahydrofuran, 30.6 g of Monomer 1, 94.5 g of 3-ethyl-3-exo-tetracyclo[4.4.0.1$^{2,5}$.1$^{7,10}$]dodecanyl methacrylate, 54.3 g of 3-hydroxy-1-adamantyl methacrylate, 103.2 g of 4,8-dioxa-5-oxotricyclo[4.2.1.0$^{3,7}$]nonan-2-yl methacrylate, and 0.84 g of 2-mercaptoethanol were mixed. The mixture was heated to 60° C., and 5.28 g of 2,2'-azobisisobutyronitrile added. The mixture was stirred for 20 hours while maintaining at 60° C. The reaction solution was cooled to room temperature, and with vigorous stirring, added dropwise to 10 L of hexane. The resulting solids were collected by filtration and dried in vacuum at 40° C. for 15 hours, obtaining a polymer in white powder solid form, designated Polymer 1. The amount was 252 g in a yield of 89.0%. Polymer 1 had a copolymer compositional ratio of approximately 10/30/20/40 as determined from an integration ratio based on $^1$H-NMR spectrum. It had a Mw of 6,800 as determined by GPC versus polystyrene standards.

Polymer 1

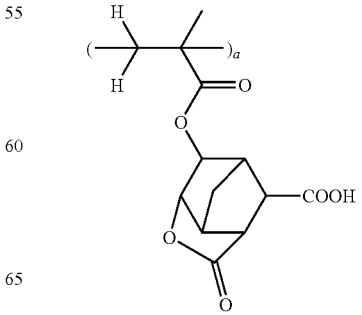

-continued

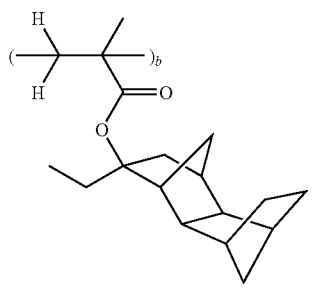

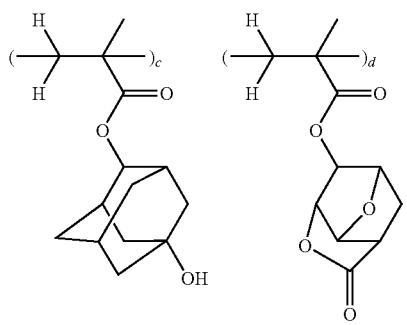

(a = 0.10, b = 0.30, c = 0.20, c = 0.40, Mw = 6,800)

Examples 2-2 to 2-30 and Comparative Examples 1-1 to 1-6

Synthesis of Polymers 2 to 36

Polymers 2 to 36 were synthesized by the same procedure as Example 2-1 except that the type and proportion of monomers were changed, with their compositional proportion (in molar ratio) and Mw being shown in Table 1. In Table 1, recurring units are abbreviated as (A1) to (E6), whose structures are shown below. (A1) to (A5) designate recurring units derived from carboxylic acid-containing lactone compounds within the scope of the invention; (B1) to (B12) designate recurring units of formula (3); (C1) and (C2) designate recurring units of formula (4); (D1) to (D10) designate recurring units of formula (5); and (E1) to (E6) designate recurring units derived from comparative carboxylic acids.

(A1)

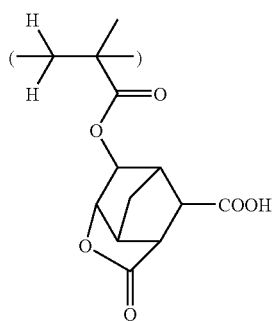

(A2)

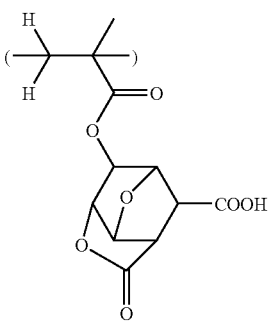

(A3)

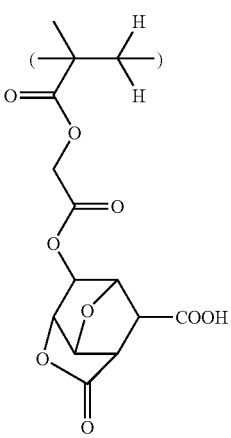

(A4)

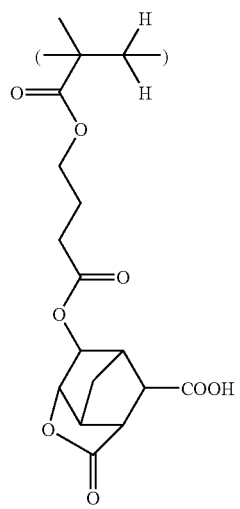
(A5)
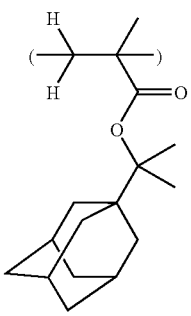
(B5)
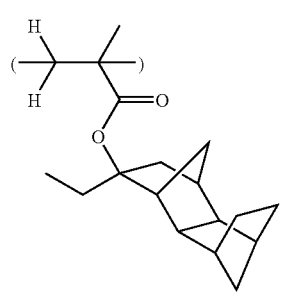
(B1)
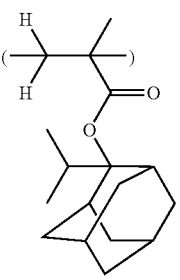
(B6)
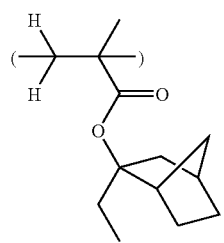
(B2)
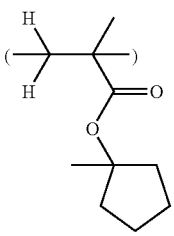
(B7)
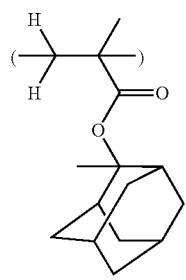
(B3)
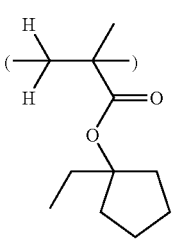
(B8)
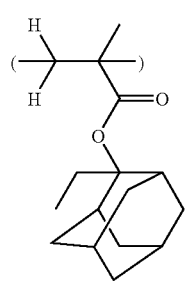
(B4)
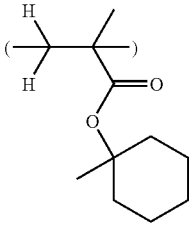
(B9)
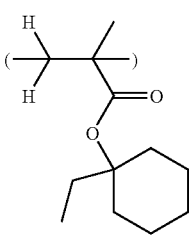
(B10)

(B11) 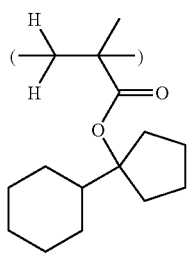
(B12) 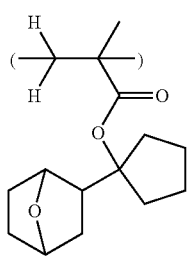
(C1) 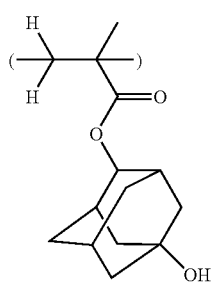
(C2) 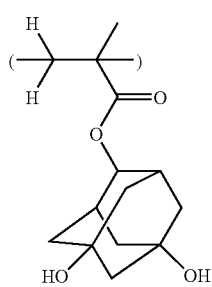
(D1) 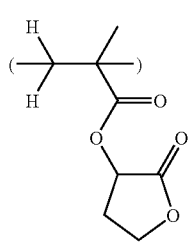
(D2) 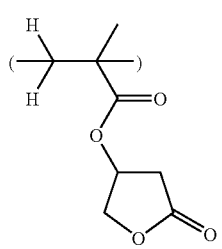
(D3) 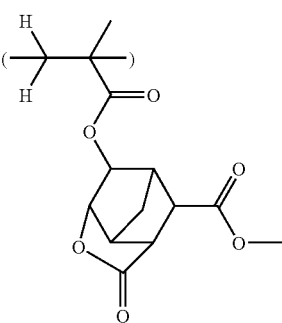
(D4) 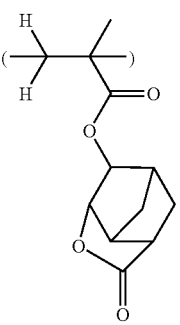
(D5) 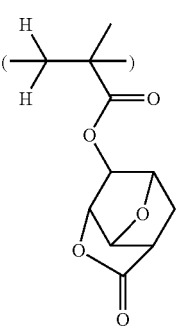
(D6) 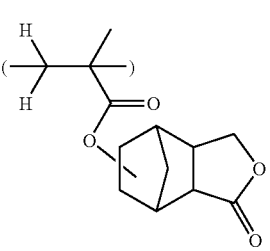
(D7) 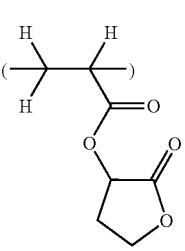

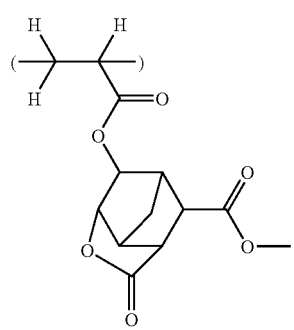 (D8)
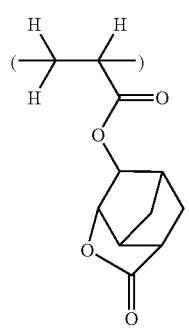 (D9)
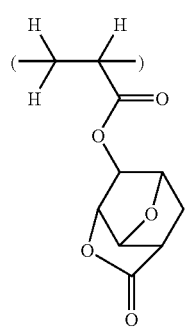 (D10)
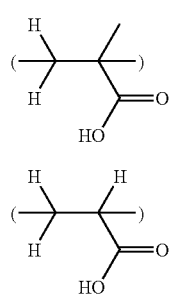 (E1)
(E2)
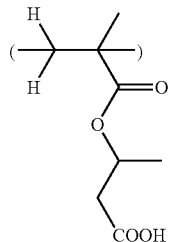 (E3)
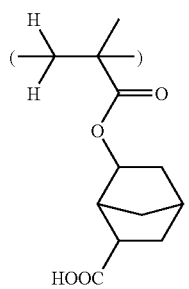 (E4)
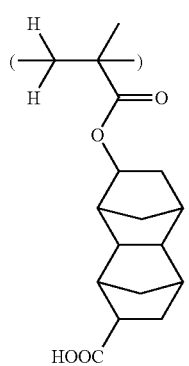 (E5)
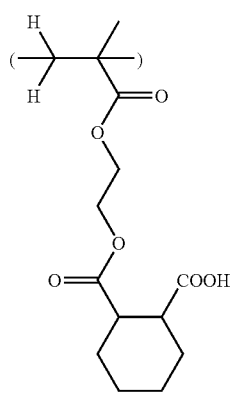 (E6)

TABLE 1

| | | Resin | Unit 1 | Unit 2 | Unit 3 | Unit 4 | Unit ratio | Mw |
|---|---|---|---|---|---|---|---|---|
| Example | 2-1 | Polymer 1 | A1 | B1 | C1 | D5 | 10/30/20/40 | 6,800 |
| | 2-2 | Polymer 2 | A1 | B1 | C1 | D5 | 15/30/20/35 | 7,200 |
| | 2-3 | Polymer 3 | A1 | B1 | C1 | D5 | 5/30/20/45 | 6,700 |
| | 2-4 | Polymer 4 | A1 | B1 | C1 | D5 | 10/20/20/50 | 6,900 |
| | 2-5 | Polymer 5 | A1 | B1 | C1 | D5 | 10/50/20/20 | 7,100 |
| | 2-6 | Polymer 6 | A2 | B1 | C1 | D5 | 10/30/20/40 | 7,200 |
| | 2-7 | Polymer 7 | A3 | B1 | C1 | D5 | 10/30/20/40 | 6,400 |
| | 2-8 | Polymer 8 | A4 | B1 | C1 | D5 | 10/30/20/40 | 6,300 |
| | 2-9 | Polymer 9 | A5 | B1 | C1 | D5 | 10/30/20/40 | 6,700 |
| | 2-10 | Polymer 10 | A1 | B2 | C1 | D5 | 10/30/20/40 | 5,900 |
| | 2-11 | Polymer 11 | A1 | B3 | C1 | D5 | 10/30/20/40 | 7,000 |
| | 2-12 | Polymer 12 | A1 | B4 | C1 | D5 | 10/30/20/40 | 6,500 |
| | 2-13 | Polymer 13 | A1 | B5 | C1 | D5 | 10/30/20/40 | 6,900 |
| | 2-14 | Polymer 14 | A1 | B6 | C1 | D5 | 10/30/20/40 | 7,200 |
| | 2-15 | Polymer 15 | A1 | B7 | C1 | D5 | 10/30/20/40 | 6,900 |
| | 2-16 | Polymer 16 | A1 | B8 | C1 | D5 | 10/30/20/40 | 6,800 |
| | 2-17 | Polymer 17 | A1 | B9 | C1 | D5 | 10/30/20/40 | 7,100 |
| | 2-18 | Polymer 18 | A1 | B10 | C1 | D5 | 10/30/20/40 | 6,300 |
| | 2-19 | Polymer 19 | A1 | B11 | C1 | D5 | 10/30/20/40 | 6,500 |
| | 2-20 | Polymer 20 | A1 | B12 | C1 | D5 | 10/30/20/40 | 7,000 |
| | 2-21 | Polymer 21 | A1 | B1 | C2 | D5 | 10/30/20/40 | 6,900 |
| | 2-22 | Polymer 22 | A1 | B1 | C1 | D1 | 10/30/20/40 | 7,100 |
| | 2-23 | Polymer 23 | A1 | B1 | C1 | D2 | 10/30/20/40 | 6,800 |
| | 2-24 | Polymer 24 | A1 | B1 | C1 | D3 | 10/30/20/40 | 6,600 |
| | 2-25 | Polymer 25 | A1 | B1 | C1 | D4 | 10/30/20/40 | 6,500 |
| | 2-26 | Polymer 26 | A1 | B1 | C1 | D6 | 10/30/20/40 | 6,300 |
| | 2-27 | Polymer 27 | A1 | B1 | C1 | D7 | 10/30/20/40 | 7,000 |
| | 2-28 | Polymer 28 | A1 | B1 | C1 | D8 | 10/30/20/40 | 7,100 |
| | 2-29 | Polymer 29 | A1 | B1 | C1 | D9 | 10/30/20/40 | 7,200 |
| | 2-30 | Polymer 30 | A1 | B1 | C1 | D10 | 10/30/20/40 | 6,600 |
| Comparative Example | 1-1 | Polymer 31 | E1 | B1 | C1 | D5 | 10/30/20/40 | 6,500 |
| | 1-2 | Polymer 32 | E2 | B1 | C1 | D5 | 10/30/20/40 | 6,400 |
| | 1-3 | Polymer 33 | E3 | B1 | C1 | D5 | 10/30/20/40 | 7,100 |
| | 1-4 | Polymer 34 | E4 | B1 | C1 | D5 | 10/30/20/40 | 7,000 |
| | 1-5 | Polymer 35 | E5 | B1 | C1 | D5 | 10/30/20/40 | 6,900 |
| | 1-6 | Polymer 36 | E6 | B1 | C1 | D5 | 10/30/20/40 | 7,200 |

Preparation of Resist Compositions

Examples 3-1 to 3-58 & Comparative Examples 2-1 to 2-6

Resist compositions were prepared by using inventive resins (Polymers 1 to 30, abbreviated P01 to P30) or comparative resins (Polymers 31 to 36, abbreviated P31 to P36) as the base resin, and dissolving the polymer, an acid generator (PAG), and a quencher (Base) in a solvent mixture (PGMEA and CyHO) containing 0.01 wt % of surfactant KH-20 (Asahi Glass Co., Ltd.) in accordance with the recipe shown in Table 2. These compositions were each filtered through a Teflon® filter having a pore diameter 0.2 µm, thereby giving inventive resist solutions (R-01 to 58) and comparative resist solutions (R-59 to 64).

TABLE 2

| | | Resist | Resin (pbw) | PAG (pbw) | Base (pbw) | Solvent 1 (pbw) | Solvent 2 (pbw) |
|---|---|---|---|---|---|---|---|
| Example | 3-1 | R-01 | P-01 (80) | PAG-1 (6.5) | Base-1 (1.06) | PGMEA (840) | CyHO (360) |
| | 3-2 | R-02 | P-02 (80) | PAG-1 (6.5) | Base-1 (1.06) | PGMEA (840) | CyHO (360) |
| | 3-3 | R-03 | P-03 (80) | PAG-1 (6.5) | Base-1 (1.06) | PGMEA (840) | CyHO (360) |
| | 3-4 | R-04 | P-04 (80) | PAG-1 (6.5) | Base-1 (1.06) | PGMEA (840) | CyHO (360) |
| | 3-5 | R-05 | P-05 (80) | PAG-1 (6.5) | Base-1 (1.06) | PGMEA (840) | CyHO (360) |
| | 3-6 | R-06 | P-06 (80) | PAG-1 (6.5) | Base-1 (1.06) | PGMEA (840) | CyHO (360) |
| | 3-7 | R-07 | P-07 (80) | PAG-1 (6.5) | Base-1 (1.06) | PGMEA (840) | CyHO (360) |
| | 3-8 | R-08 | P-08 (80) | PAG-1 (6.5) | Base-1 (1.06) | PGMEA (840) | CyHO (360) |
| | 3-9 | R-09 | P-09 (80) | PAG-1 (6.5) | Base-1 (1.06) | PGMEA (840) | CyHO (360) |
| | 3-10 | R-10 | P-10 (80) | PAG-1 (6.5) | Base-1 (1.06) | PGMEA (840) | CyHO (360) |
| | 3-11 | R-11 | P-11 (80) | PAG-1 (6.5) | Base-1 (1.06) | PGMEA (840) | CyHO (360) |
| | 3-12 | R-12 | P-12 (80) | PAG-1 (6.5) | Base-1 (1.06) | PGMEA (840) | CyHO (360) |
| | 3-13 | R-13 | P-13 (80) | PAG-1 (6.5) | Base-1 (1.06) | PGMEA (840) | CyHO (360) |
| | 3-14 | R-14 | P-14 (80) | PAG-1 (6.5) | Base-1 (1.06) | PGMEA (840) | CyHO (360) |
| | 3-15 | R-15 | P-15 (80) | PAG-1 (6.5) | Base-1 (1.06) | PGMEA (840) | CyHO (360) |
| | 3-16 | R-16 | P-16 (80) | PAG-1 (6.5) | Base-1 (1.06) | PGMEA (840) | CyHO (360) |
| | 3-17 | R-17 | P-17 (80) | PAG-1 (6.5) | Base-1 (1.06) | PGMEA (840) | CyHO (360) |
| | 3-18 | R-18 | P-18 (80) | PAG-1 (6.5) | Base-1 (1.06) | PGMEA (840) | CyHO (360) |
| | 3-19 | R-19 | P-19 (80) | PAG-1 (6.5) | Base-1 (1.06) | PGMEA (840) | CyHO (360) |
| | 3-20 | R-20 | P-20 (80) | PAG-1 (6.5) | Base-1 (1.06) | PGMEA (840) | CyHO (360) |
| | 3-21 | R-21 | P-21 (80) | PAG-1 (6.5) | Base-1 (1.06) | PGMEA (840) | CyHO (360) |
| | 3-22 | R-22 | P-22 (80) | PAG-1 (6.5) | Base-1 (1.06) | PGMEA (840) | CyHO (360) |
| | 3-23 | R-23 | P-23 (80) | PAG-1 (6.5) | Base-1 (1.06) | PGMEA (840) | CyHO (360) |
| | 3-24 | R-24 | P-24 (80) | PAG-1 (6.5) | Base-1 (1.06) | PGMEA (840) | CyHO (360) |

TABLE 2-continued

|  | Resist | Resin (pbw) | PAG (pbw) | Base (pbw) | Solvent 1 (pbw) | Solvent 2 (pbw) |
|---|---|---|---|---|---|---|
|  | 3-25 | R-25 | P-25 (80) | PAG-1 (6.5) | Base-1 (1.06) | PGMEA (840) | CyHO (360) |
|  | 3-26 | R-26 | P-26 (80) | PAG-1 (6.5) | Base-1 (1.06) | PGMEA (840) | CyHO (360) |
|  | 3-27 | R-27 | P-27 (80) | PAG-1 (6.5) | Base-1 (1.06) | PGMEA (840) | CyHO (360) |
|  | 3-28 | R-28 | P-28 (80) | PAG-1 (6.5) | Base-1 (1.06) | PGMEA (840) | CyHO (360) |
|  | 3-29 | R-29 | P-29 (80) | PAG-1 (6.5) | Base-1 (1.06) | PGMEA (840) | CyHO (360) |
|  | 3-30 | R-30 | P-30 (80) | PAG-1 (6.5) | Base-1 (1.06) | PGMEA (840) | CyHO (360) |
|  | 3-31 | R-31 | P-01 (80) | PAG-2 (7.4) | Base-1 (1.06) | PGMEA (840) | CyHO (360) |
|  | 3-32 | R-32 | P-06 (80) | PAG-2 (7.4) | Base-1 (1.06) | PGMEA (840) | CyHO (360) |
|  | 3-33 | R-33 | P-07 (80) | PAG-2 (7.4) | Base-1 (1.06) | PGMEA (840) | CyHO (360) |
|  | 3-34 | R-34 | P-14 (80) | PAG-2 (7.4) | Base-1 (1.06) | PGMEA (840) | CyHO (360) |
|  | 3-35 | R-35 | P-18 (80) | PAG-2 (7.4) | Base-1 (1.06) | PGMEA (840) | CyHO (360) |
|  | 3-36 | R-36 | P-22 (80) | PAG-2 (7.4) | Base-1 (1.06) | PGMEA (840) | CyHO (360) |
|  | 3-37 | R-37 | P-24 (80) | PAG-2 (7.4) | Base-1 (1.06) | PGMEA (840) | CyHO (360) |
|  | 3-38 | R-38 | P-01 (80) | PAG-3 (7.0) | Base-1 (1.06) | PGMEA (840) | CyHO (360) |
|  | 3-39 | R-39 | P-06 (80) | PAG-3 (7.0) | Base-1 (1.06) | PGMEA (640) | CyHO (360) |
|  | 3-40 | R-40 | P-07 (80) | PAG-3 (7.0) | Base-1 (1.06) | PGMEA (840) | CyHO (360) |
|  | 3-41 | R-41 | P-14 (80) | PAG-3 (7.0) | Base-1 (1.06) | PGMEA (840) | CyHO (360) |
|  | 3-42 | R-42 | P-18 (80) | PAG-3 (7.0) | Base-1 (1.06) | PGMEA (840) | CyHO (360) |
|  | 3-43 | R-43 | P-22 (80) | PAG-3 (7.0) | Base-1 (1.06) | PGMEA (840) | CyHO (360) |
|  | 3-44 | R-44 | P-24 (80) | PAG-3 (7.0) | Base-1 (1.06) | PGMEA (840) | CyHO (360) |
|  | 3-45 | R-45 | P-01 (80) | PAG-1 (3.3) PAG-3 (3.5) | Base-1 (1.06) | PGMEA (840) | CyHO (360) |
|  | 3-46 | R-46 | P-06 (80) | PAG-1 (3.3) PAG-3 (3.5) | Base-1 (1.06) | PGMEA (840) | CyHO (360) |
|  | 3-47 | R-47 | P-07 (80) | PAG-1 (3.3) PAG-3 (3.5) | Base-1 (1.06) | PGMEA (840) | CyHO (360) |
|  | 3-48 | R-48 | P-14 (80) | PAG-1 (3.3) PAG-3 (3.5) | Base-1 (1.06) | PGMEA (840) | CyHO (360) |
|  | 3-49 | R-49 | P-18 (80) | PAG-1 (3.3) PAG-3 (3.5) | Base-1 (1.06) | PGMEA (840) | CyHO (360) |
|  | 3-50 | R-50 | P-22 (80) | PAG-1 (3.3) PAG-3 (3.5) | Base-1 (1.06) | PGMEA (840) | CyHO (360) |
|  | 3-51 | R-51 | P-24 (80) | PAG-1 (3.3) PAG-3 (3.5) | Base-1 (1.06) | PGMEA (840) | CyHO (360) |
|  | 3-52 | R-52 | P-01 (80) | PAG-1 (6.5) | Base-2 (0.83) | PGMEA (840) | CyHO (360) |
|  | 3-53 | R-53 | P-06 (80) | PAG-1 (6.5) | Base-2 (0.83) | PGMEA (840) | CyHO (360) |
|  | 3-54 | R-54 | P-07 (80) | PAG-1 (6.5) | Base-2 (0.83) | PGMEA (840) | CyHO (360) |
|  | 3-55 | R-55 | P-14 (80) | PAG-1 (6.5) | Base-2 (0.83) | PGMEA (840) | CyHO (360) |
|  | 3-56 | R-56 | P-18 (80) | PAG-1 (6.5) | Base-2 (0.83) | PGMEA (840) | CyHO (360) |
|  | 3-57 | R-57 | P-22 (80) | PAG-1 (6.5) | Base-2 (0.83) | PGMEA (840) | CyHO (360) |
|  | 3-58 | R-58 | P-24 (80) | PAG-1 (6.5) | Base-2 (0.83) | PGMEA (840) | CyHO (360) |
| Comparative Example | 2-1 | R-59 | P-31 (80) | PAG-1 (6.5) | Base-1 (1.06) | PGMEA (840) | CyHO (360) |
|  | 2-2 | R-60 | P-32 (80) | PAG-1 (6.5) | Base-1 (1.06) | PGMEA (840) | CyHO (360) |
|  | 2-3 | R-61 | P-33 (80) | PAG-1 (6.5) | Base-1 (1.06) | PGMEA (840) | CyHO (360) |
|  | 2-4 | R-62 | P-34 (80) | PAG-1 (6.5) | Base-1 (1.06) | PGMEA (840) | CyHO (360) |
|  | 2-5 | R-63 | P-35 (80) | PAG-1 (6.5) | Base-1 (1.06) | PGMEA (840) | CyHO (360) |
|  | 2-6 | R-64 | P-36 (80) | PAG-1 (6.5) | Base-1 (1.06) | PGMEA (840) | CyHO (360) |

The acid generator, quencher (base) and solvent shown in Table 2 have the following meanings.
PAG-1: triphenylsulfonium nonafluorobutanesulfonate
PAG-2: 4-t-butoxyphenyldiphenylsulfonium nonafluorobutanesulfonate
PAG-3: triphenylsulfonium 1,1,3,3,3-pentafluoro-2-cyclo-hexylcarboxypropanesulfonate
Base-1: tri(2-methoxymethoxyethyl)amine
Base-2: 2-(2-methoxyethoxymethoxy)ethylmorpholine
PGMEA: 1-methoxyisopropyl acetate
CyHO: cyclohexanone Evaluation of Resolution and Line Edge Roughness Examples 4-1 to 4-58 & Comparative Examples 3-1 to 3-6

Each of inventive resist compositions (R-01 to 58) and comparative resist compositions (R-59 to 64) was spin coated on a silicon wafer having an antireflective coating (ARC-29A, Nissan Chemical Co., Ltd.) of 78 nm thick and baked at 110° C. for 60 seconds, forming a resist film of 150 nm thick. The wafer was exposed by means of an ArF excimer laser stepper (Nikon Corp., NA 0.85), post-exposure baked (PEB) for 60 seconds, and puddle developed with a 2.38 wt % tetramethylammonium hydroxide aqueous solution for 30 seconds, forming a 1:1 line-and-space pattern and a 1:10 isolated line pattern. During the PEB, an optimum temperature for each resist composition was employed.

The patterned wafer was observed under a top-down scanning electron microscope (TDSEM). The optimum exposure (Eop) was defined as the exposure dose (mJ/cm$^2$) which provided a 1:1 resolution at the top and bottom of a 90-nm 1:1 line-and-space pattern. The maximum resolution of the resist was defined as the minimum line width (on-mask size, in increments of 5 nm) of a 1:1 line-and-space pattern that was resolved and separated at the optimum exposure, with smaller values indicating better resolution. The 1:10 isolated line pattern at the optimum exposure was also observed for determining an actual on-wafer size of the isolated line pattern with an on-mask size of 140 nm, which was reported as mask fidelity (on-wafer size, a larger size being better). Further, a line portion of the 90-nm 1:1 line-and-space pattern was examined for line edge roughness (LER). For each of left and right edges of a line, measurement was made at 16 points along a measurement region of 300 nm long. Provided that L and R represent averages of deviations of measurement points from the center line along the left and right edges, respectively, a square root of $(L^2+R^2)$ is reported as LER (in nm, smaller deviation being better).

Table 3 tabulates the test results (maximum resolution, mask fidelity and LER) of the inventive and comparative resist compositions.

TABLE 3

|  |  | Resist | PEB temp. | Eop | Maximum resolution | Mask fidelity | LER |
|---|---|---|---|---|---|---|---|
| Example | 4-1 | R-01 | 100° C. | 29 mJ/cm² | 70 nm | 99 nm | 5.7 nm |
|  | 4-2 | R-02 | 100° C. | 27 mJ/cm² | 70 nm | 95 nm | 5.5 nm |
|  | 4-3 | R-03 | 100° C. | 30 mJ/cm² | 75 nm | 95 nm | 6.0 nm |
|  | 4-4 | R-04 | 100° C. | 35 mJ/cm² | 75 nm | 94 nm | 6.1 nm |
|  | 4-5 | R-05 | 90° C. | 30 mJ/cm² | 75 nm | 92 nm | 6.2 nm |
|  | 4-6 | R-06 | 100° C. | 30 mJ/cm² | 75 nm | 101 nm | 5.8 nm |
|  | 4-7 | R-07 | 100° C. | 27 mJ/cm² | 70 nm | 97 nm | 5.6 nm |
|  | 4-8 | R-08 | 100° C. | 28 mJ/cm² | 70 nm | 99 nm | 5.7 nm |
|  | 4-9 | R-09 | 100° C. | 26 mJ/cm² | 70 nm | 94 nm | 5.5 nm |
|  | 4-10 | R-10 | 100° C. | 27 mJ/cm² | 70 nm | 95 nm | 5.2 nm |
|  | 4-11 | R-11 | 115° C. | 30 mJ/cm² | 70 nm | 102 nm | 5.5 nm |
|  | 4-12 | R-12 | 100° C. | 31 mJ/cm² | 70 nm | 100 nm | 5.8 nm |
|  | 4-13 | R-13 | 110° C. | 33 mJ/cm² | 70 nm | 99 nm | 6.0 nm |
|  | 4-14 | R-14 | 95° C. | 28 mJ/cm² | 70 nm | 97 nm | 5.6 nm |
|  | 4-15 | R-15 | 110° C. | 28 mJ/cm² | 70 nm | 95 nm | 5.3 nm |
|  | 4-16 | R-16 | 110° C. | 26 mJ/cm² | 70 nm | 95 nm | 5.1 nm |
|  | 4-17 | R-17 | 110° C. | 29 mJ/cm² | 75 nm | 96 nm | 5.4 nm |
|  | 4-18 | R-18 | 110° C. | 28 mJ/cm² | 70 nm | 94 nm | 5.3 nm |
|  | 4-19 | R-19 | 95° C. | 29 mJ/cm² | 70 nm | 95 nm | 5.5 nm |
|  | 4-20 | R-20 | 100° C. | 32 mJ/cm² | 70 nm | 103 nm | 5.2 nm |
|  | 4-21 | R-21 | 100° C. | 28 mJ/cm² | 70 nm | 100 nm | 5.8 nm |
|  | 4-22 | R-22 | 90° C. | 31 mJ/cm² | 70 nm | 98 nm | 5.2 nm |
|  | 4-23 | R-23 | 90° C. | 28 mJ/cm² | 70 nm | 96 nm | 5.0 nm |
|  | 4-24 | R-24 | 100° C. | 30 mJ/cm² | 70 nm | 97 nm | 5.9 nm |
|  | 4-25 | R-25 | 100° C. | 30 mJ/cm² | 70 nm | 98 nm | 6.0 nm |
|  | 4-26 | R-26 | 100° C. | 31 mJ/cm² | 70 nm | 95 nm | 6.1 nm |
|  | 4-27 | R-27 | 90° C. | 28 mJ/cm² | 75 nm | 90 nm | 5.0 nm |
|  | 4-28 | R-28 | 90° C. | 26 mJ/cm² | 75 nm | 93 nm | 5.4 nm |
|  | 4-29 | R-29 | 90° C. | 29 mJ/cm² | 75 nm | 92 nm | 5.4 nm |
|  | 4-30 | R-30 | 90° C. | 28 mJ/cm² | 75 nm | 94 nm | 5.3 nm |
|  | 4-31 | R-31 | 100° C. | 36 mJ/cm² | 70 nm | 101 nm | 5.9 nm |
|  | 4-32 | R-32 | 100° C. | 37 mJ/cm² | 70 nm | 103 nm | 6.0 nm |
|  | 4-33 | R-33 | 100° C. | 34 mJ/cm² | 70 nm | 100 nm | 5.8 nm |
|  | 4-34 | R-34 | 95° C. | 35 mJ/cm² | 70 nm | 99 nm | 5.7 nm |
|  | 4-35 | R-35 | 110° C. | 35 mJ/cm² | 70 nm | 97 nm | 5.4 nm |
|  | 4-36 | R-36 | 90° C. | 38 mJ/cm² | 70 nm | 100 nm | 5.3 nm |
|  | 4-37 | R-37 | 100° C. | 37 mJ/cm² | 70 nm | 100 nm | 6.1 nm |
|  | 4-38 | R-38 | 100° C. | 33 mJ/cm² | 70 nm | 100 nm | 5.8 nm |
|  | 4-39 | R-39 | 100° C. | 34 mJ/cm² | 70 nm | 103 nm | 5.8 nm |
|  | 4-40 | R-40 | 100° C. | 31 mJ/cm² | 70 nm | 100 nm | 5.7 nm |
|  | 4-41 | R-41 | 95° C. | 32 mJ/cm² | 70 nm | 99 nm | 5.6 nm |
|  | 4-42 | R-42 | 110° C. | 32 mJ/cm² | 70 nm | 96 nm | 5.4 nm |
|  | 4-43 | R-43 | 90° C. | 35 mJ/cm² | 70 nm | 100 nm | 5.3 nm |
|  | 4-44 | R-44 | 100° C. | 34 mJ/cm² | 70 nm | 99 nm | 5.9 nm |
|  | 4-45 | R-45 | 100° C. | 30 mJ/cm² | 70 nm | 100 nm | 5.7 nm |
|  | 4-46 | R-46 | 100° C. | 32 mJ/cm² | 70 nm | 102 nm | 5.8 nm |
|  | 4-47 | R-47 | 100° C. | 29 mJ/cm² | 70 nm | 99 nm | 5.7 nm |
|  | 4-48 | R-48 | 95° C. | 30 mJ/cm² | 70 nm | 98 nm | 5.6 nm |
|  | 4-49 | R-49 | 110° C. | 30 mJ/cm² | 70 nm | 98 nm | 5.4 nm |
|  | 4-50 | R-50 | 90° C. | 33 mJ/cm² | 70 nm | 100 nm | 5.3 nm |
|  | 4-51 | R-51 | 100° C. | 32 mJ/cm² | 70 nm | 98 nm | 5.9 nm |
|  | 4-52 | R-52 | 100° C. | 28 mJ/cm² | 70 nm | 100 nm | 5.5 nm |
|  | 4-53 | R-53 | 100° C. | 29 mJ/cm² | 70 nm | 104 nm | 5.6 nm |
|  | 4-54 | R-54 | 100° C. | 27 mJ/cm² | 70 nm | 100 nm | 5.5 nm |
|  | 4-55 | R-55 | 95° C. | 27 mJ/cm² | 70 nm | 99 nm | 5.4 nm |
|  | 4-56 | R-56 | 110° C. | 27 mJ/cm² | 70 nm | 98 nm | 5.2 nm |
|  | 4-57 | R-57 | 90° C. | 30 mJ/cm² | 70 nm | 101 nm | 5.0 nm |
|  | 4-58 | R-58 | 100° C. | 29 mJ/cm² | 70 nm | 100 nm | 5.6 nm |
| Comparative Example | 3-1 | R-59 | 100° C. | 31 mJ/cm² | 70 nm | 101 nm | 6.6 nm |
|  | 3-2 | R-60 | 100° C. | 28 mJ/cm² | 75 nm | 95 nm | 6.3 nm |
|  | 3-3 | R-61 | 100° C. | 30 mJ/cm² | 75 nm | 95 nm | 6.5 nm |
|  | 3-4 | R-62 | 100° C. | 32 mJ/cm² | 75 nm | 94 nm | 6.4 nm |
|  | 3-5 | R-63 | 100° C. | 33 mJ/cm² | 75 nm | 93 nm | 6.3 nm |
|  | 3-6 | R-64 | 100° C. | 28 mJ/cm² | 75 nm | 90 nm | 6.0 nm |

It is seen from the results of Table 3 that the resist compositions within the scope of the invention have improved resolution and minimized LER when processed by ArF excimer laser lithography. The data of Comparative Examples in Table 3 reveal that prior art resist compositions satisfy either one or none of resolution and LER. It has been demonstrated that resist compositions comprising polymers comprising recurring units derived from the carboxyl-containing lactone compounds of the invention are improved in resist properties over the prior art resist compositions.

Japanese Patent Application No. 2008-120465 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising recurring units having the general formulae (2), (3), (4) and (5):

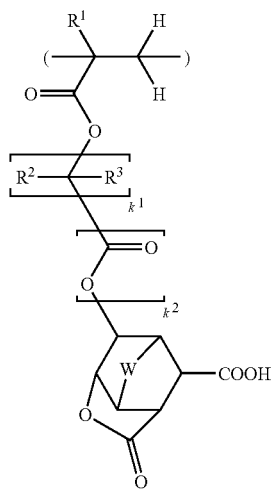
(2)

wherein $R^1$ is hydrogen or methyl, $R^2$ and $R^3$ are each independently hydrogen or a straight, branched or cyclic monovalent $C_1$-$C_{10}$ hydrocarbon group, or $R^2$ and $R^3$ may bond together to form an aliphatic hydrocarbon ring with the carbon atom to which they are attached, W is —$CH_2$—, —S— or —O—, $k^1$ is an integer of 0 to 4, and $k^2$ is 0 or 1

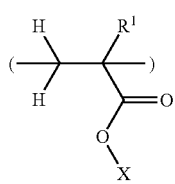
(3)

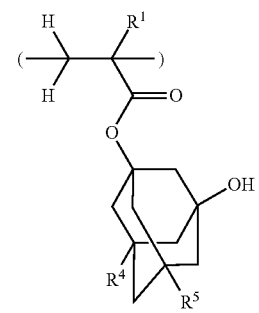
(4)

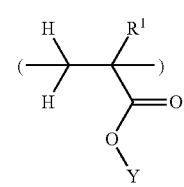
(5)

wherein $R^1$ is hydrogen, fluorine, methyl or trifluoromethyl, $R^4$ and $R^5$ are each independently hydrogen or hydroxyl, X is an acid labile group, and Y is a substituent group having a lactone structure;

wherein the recurring unit having the general formula (5) is selected from the group consisting of the following formulae:

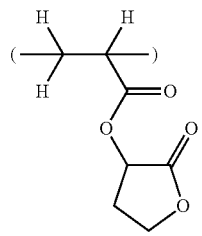 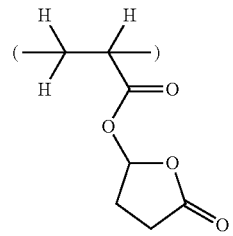

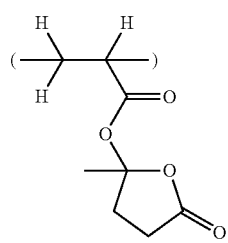 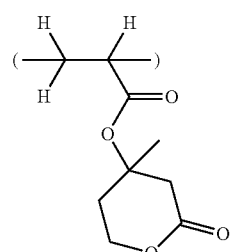

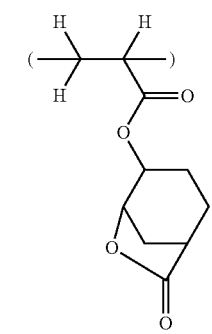

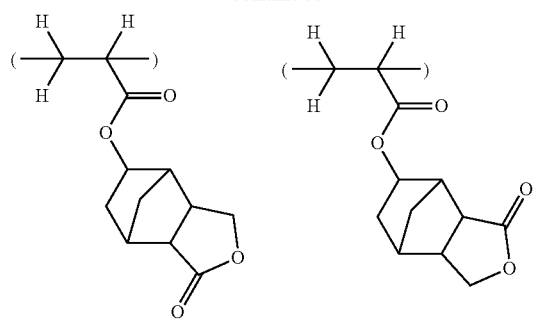
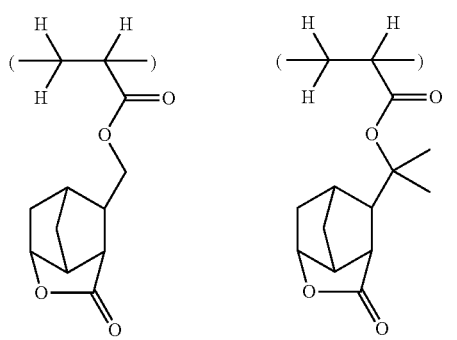
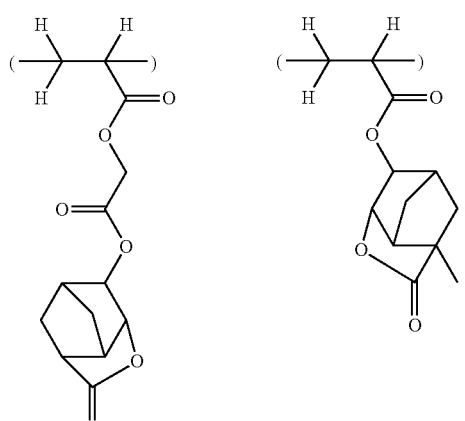
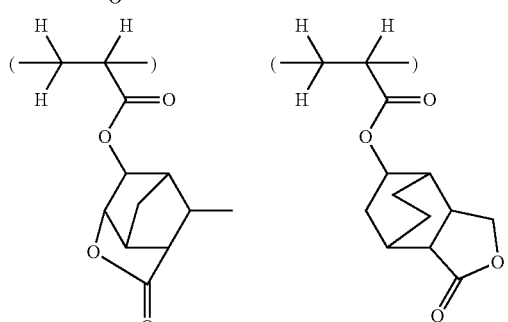
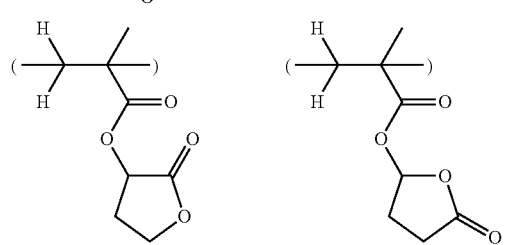
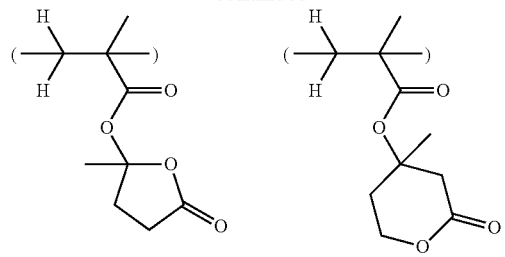
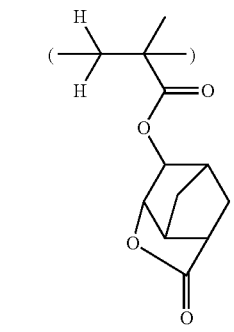
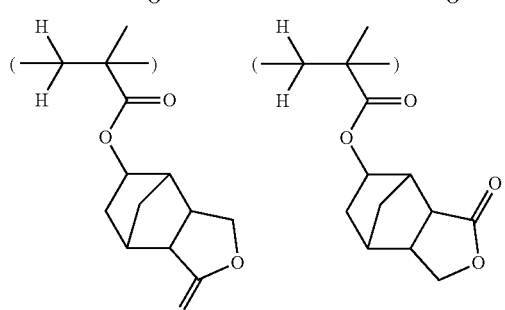
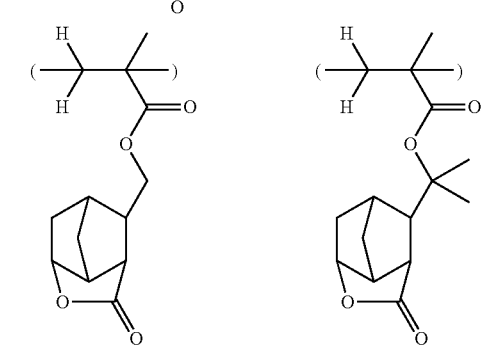
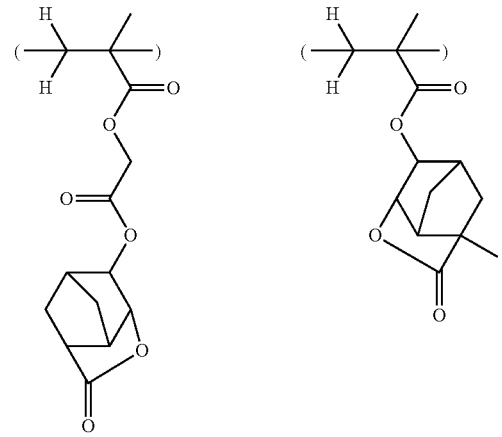

119
-continued
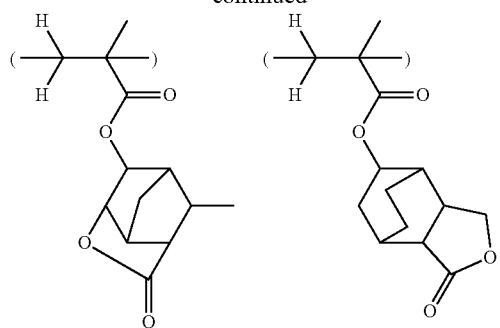
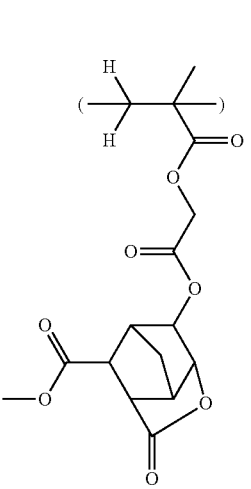
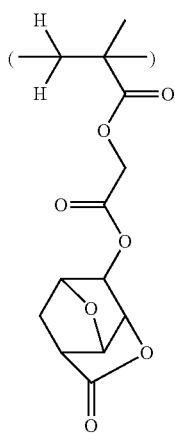 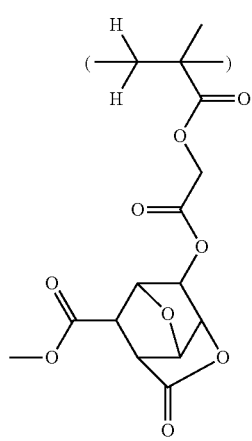
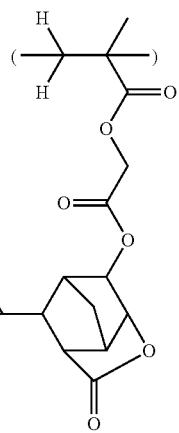
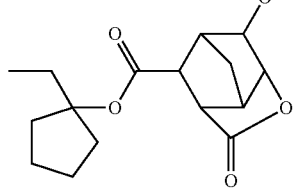
120
-continued
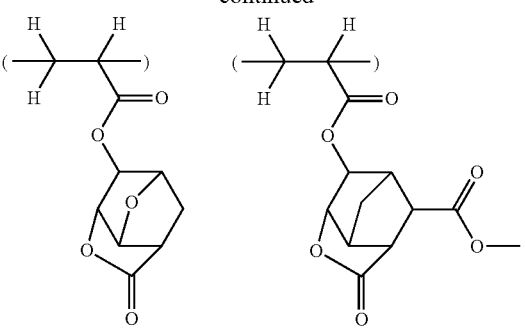
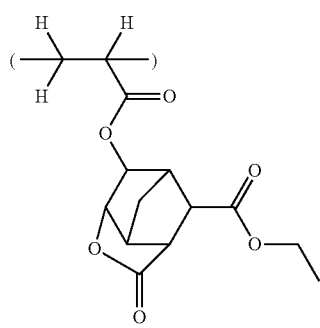
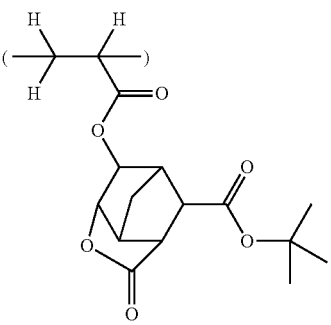
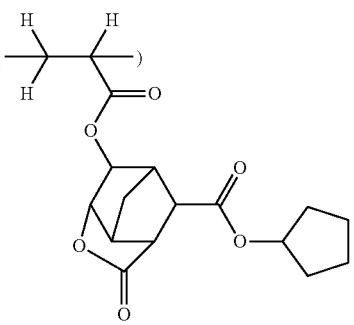
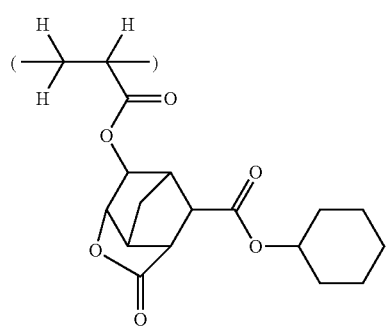

121
-continued
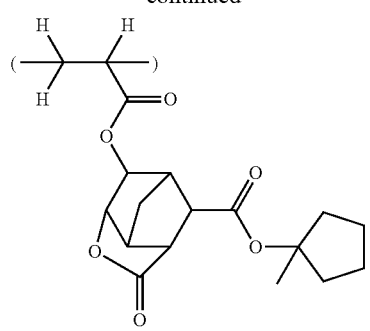
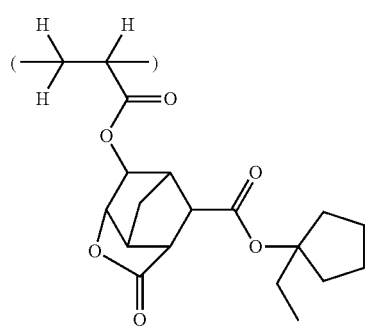
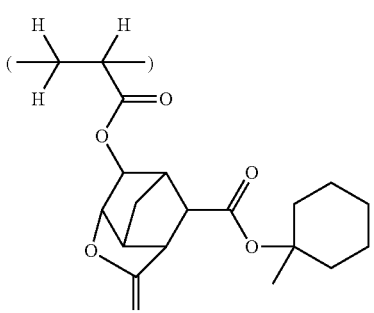
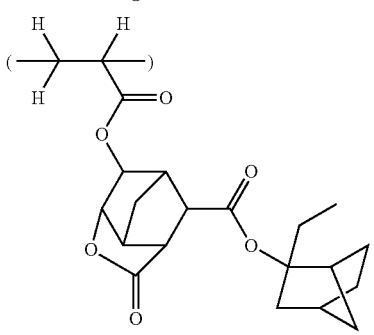
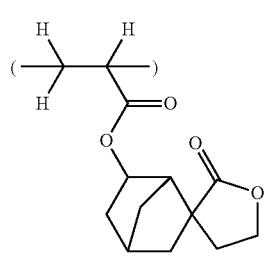
122
-continued
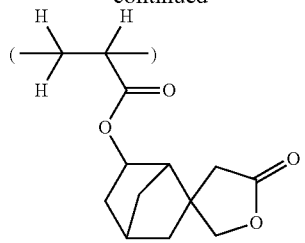
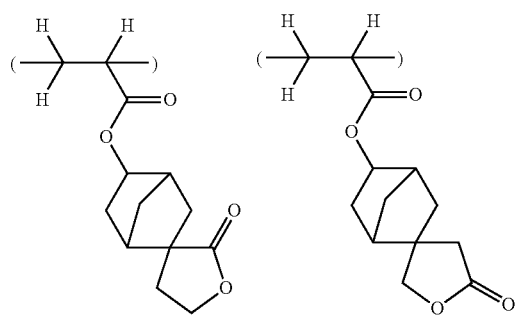
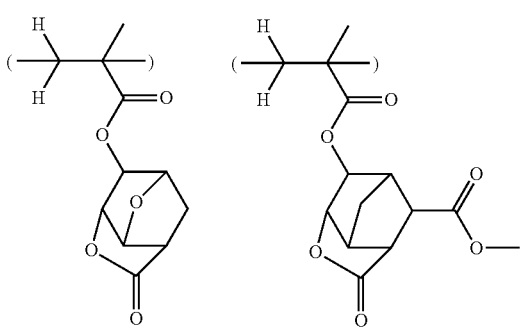
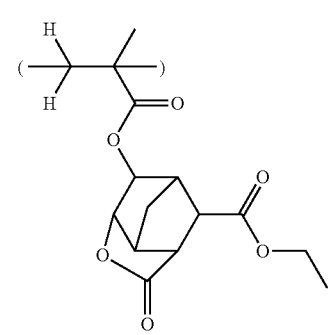
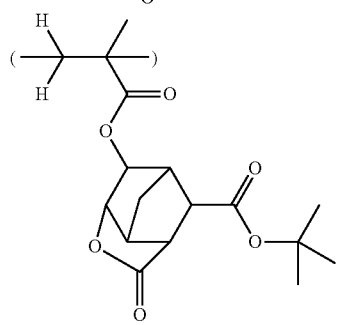

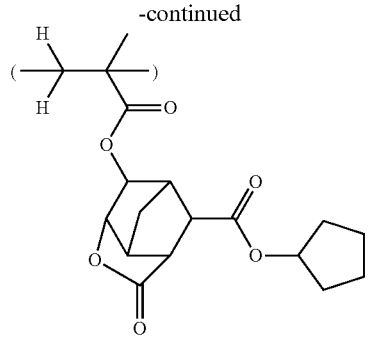

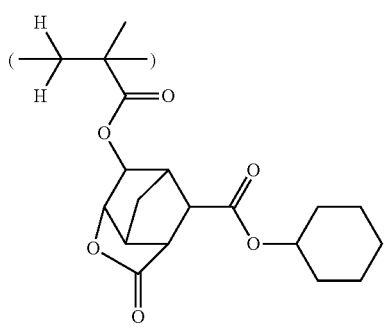

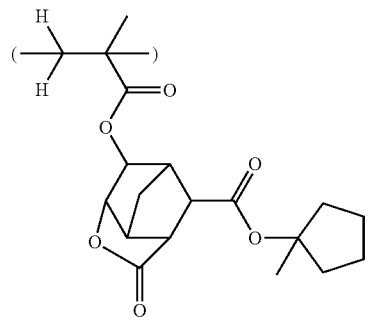

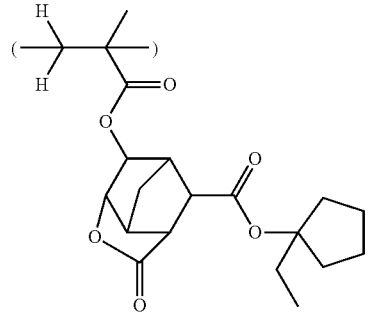

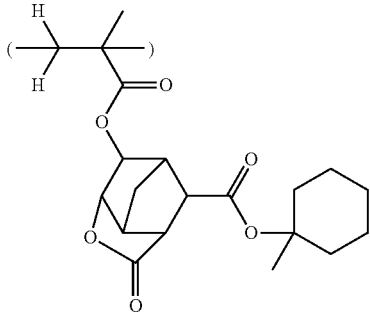

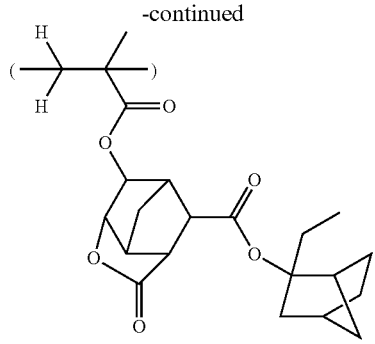

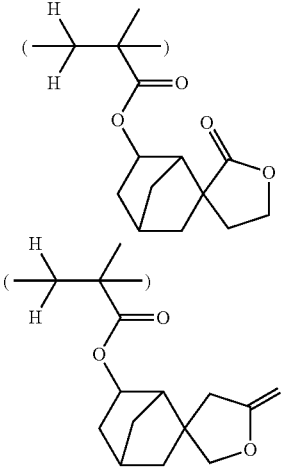

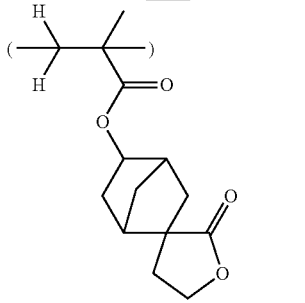

and

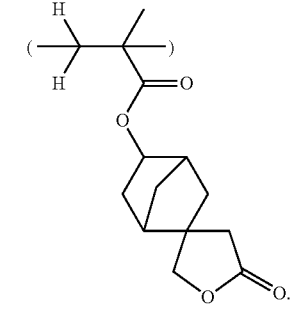

2. A resist composition comprising the polymer of claim 1 as a base resin.

3. A process for forming a pattern comprising the steps of applying the resist composition of claim 2 onto a substrate to form a resist coating, heat treating the resist coating, exposing the resist coating to high-energy radiation or electron beam through a photomask, optionally heat treating the exposed coating, and developing it with a developer.

4. A process for forming a pattern comprising the steps of applying the resist composition of claim 2 onto a substrate to form a resist coating, heat treating the resist coating, exposing the resist coating to high-energy radiation or electron beam through a photomask, heat treating the exposed coating, and developing it with a developer, said exposing step being performed by immersion lithography including holding a liquid having a refractive index of at least 1.0 between the resist coating and a projection lens.

5. A process for forming a pattern comprising the steps of applying the resist composition of claim 2 onto a substrate to form a resist coating, heat treating the resist coating, forming a protective film on the resist coating, exposing the resist coating to high-energy radiation or electron beam through a photomask, heat treating the exposed coating, and developing it with a developer, said exposing step being performed by immersion lithography including holding a liquid having a refractive index of at least 1.0 between the protective film and a projection lens.

6. A polymer consisting of recurring units having the general formulae (2), (3), (4) and (5):

(2)

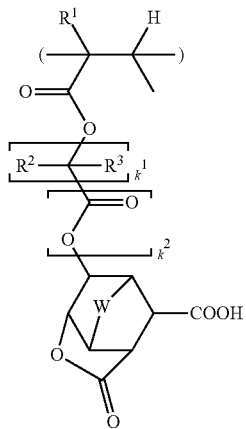

wherein $R^1$ is hydrogen or methyl, $R^2$ and $R^3$ are each independently hydrogen or a straight, branched or cyclic monovalent $C_1$-$C_{10}$ hydrocarbon group, or $R^2$ and $R^3$ may bond together to form an aliphatic hydrocarbon ring with the carbon atom to which they are attached, W is —$CH_2$—, —S— or —O—, $k^1$ is an integer of 0 to 4, and $k^2$ is 0 or 1, (3)

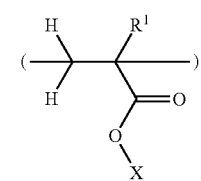

(4)

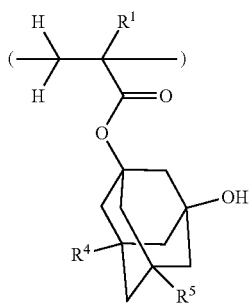

(5)

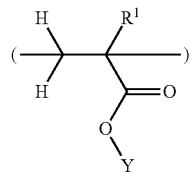

wherein $R^1$ is hydrogen, fluorine, methyl or trifluoromethyl, $R^4$ and $R^5$ are each independently hydrogen or hydroxyl, X is an acid labile group, and Y is a substituent group having a lactone structure;

wherein the recurring unit having the general formula (5) is selected from the group consisting of the following formulae:

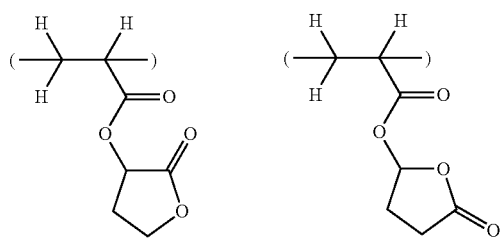

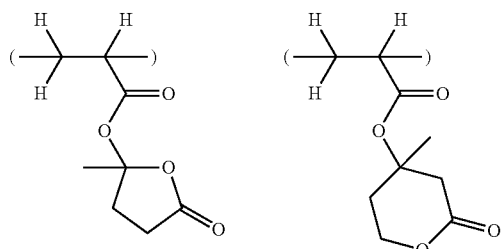

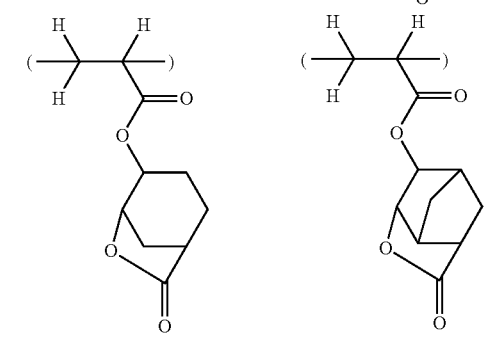

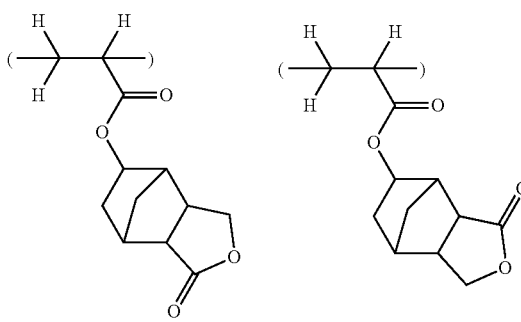

127
-continued
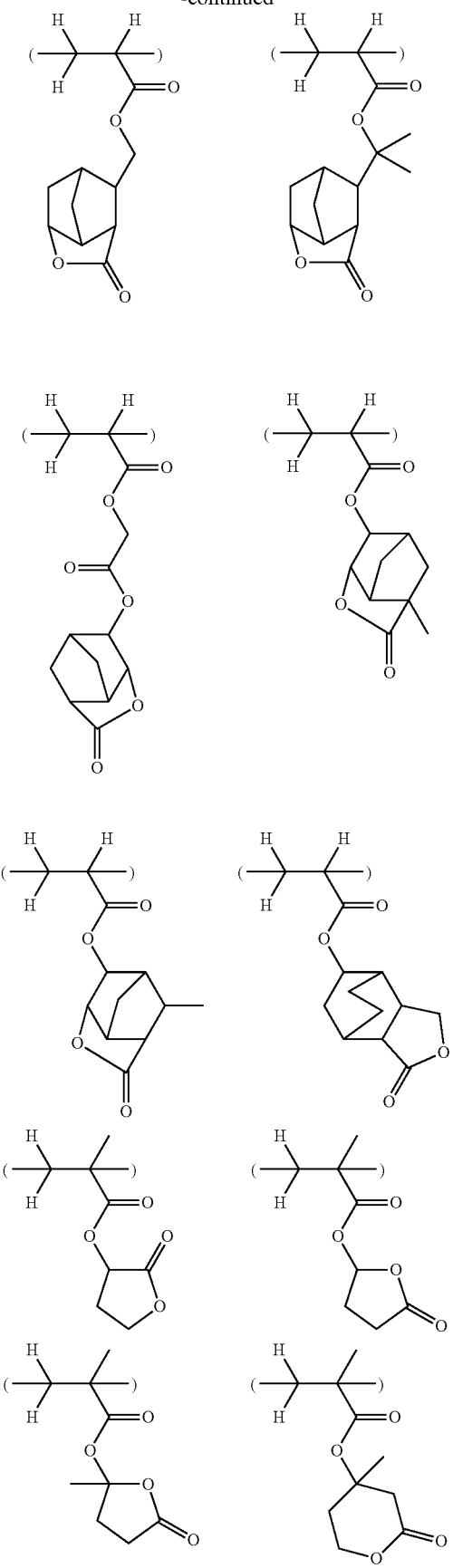
128
-continued
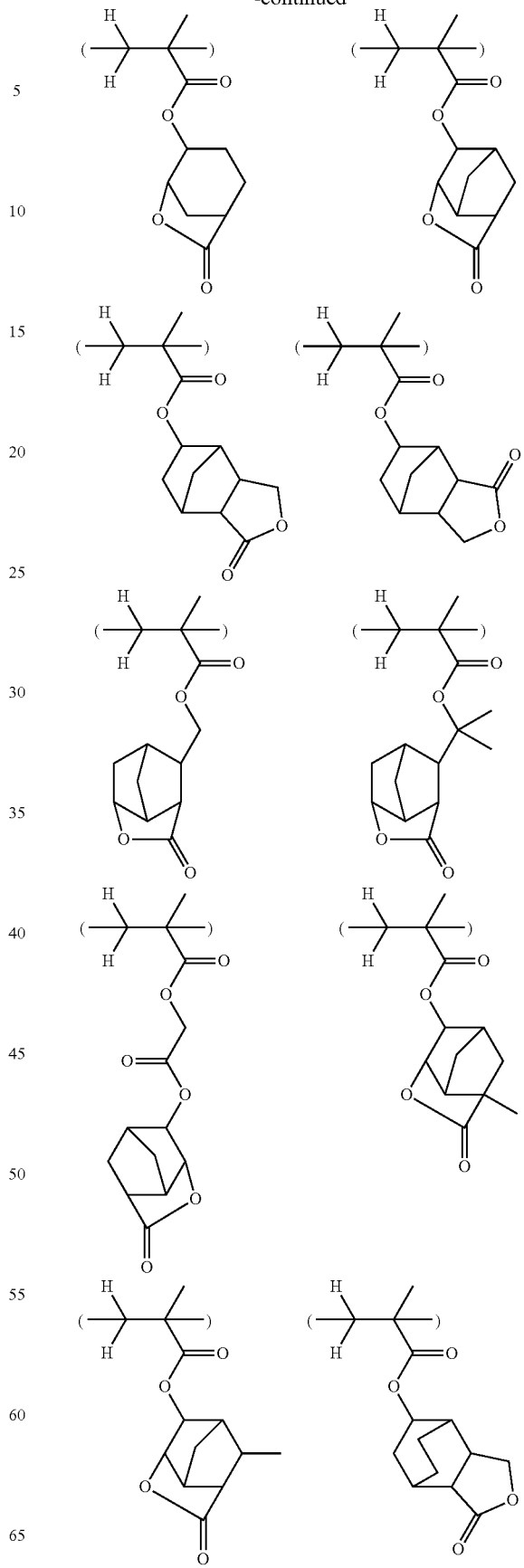

-continued
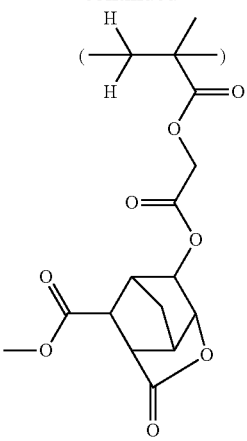
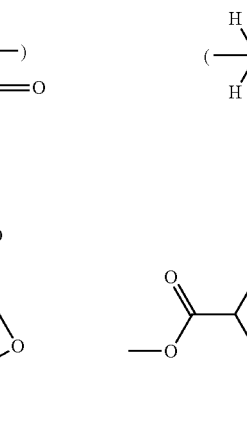 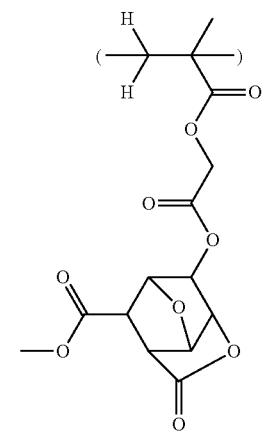
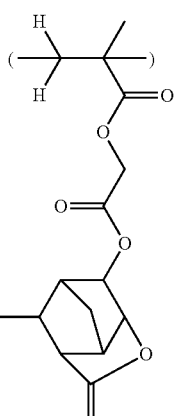
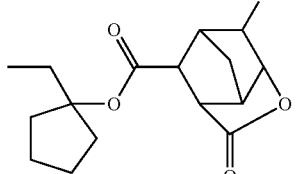
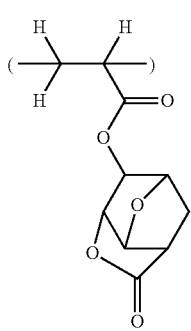 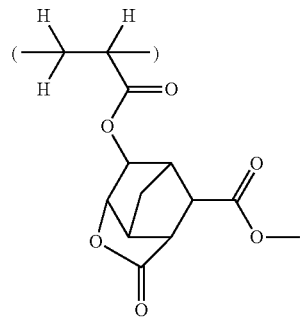
-continued
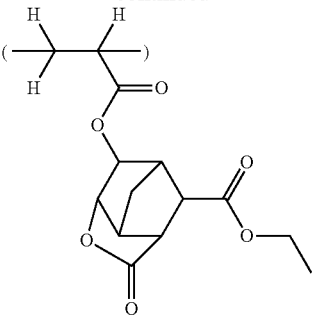
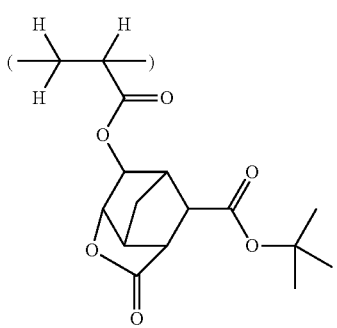
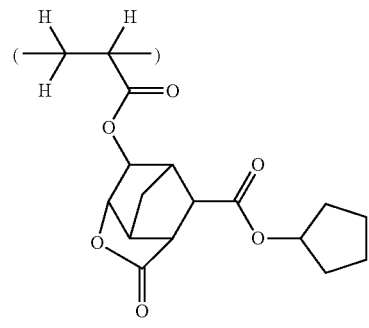
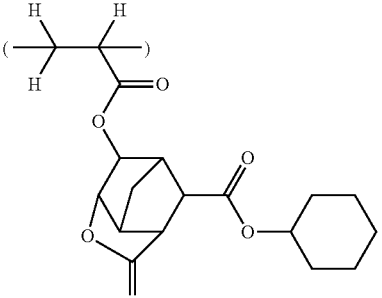
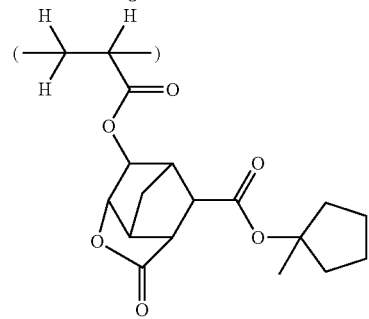

131
-continued
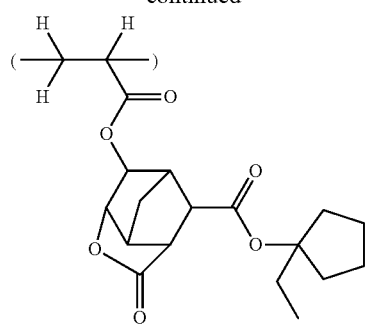
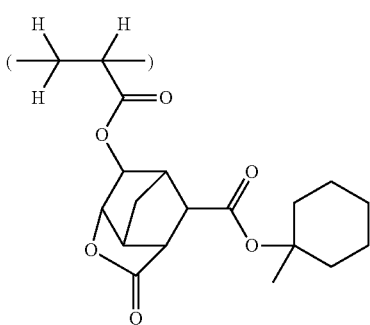
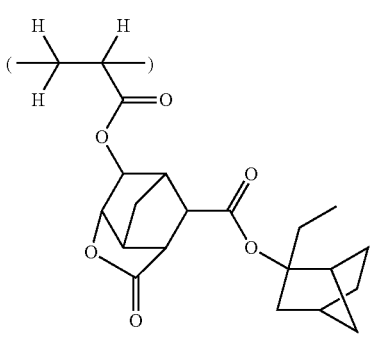
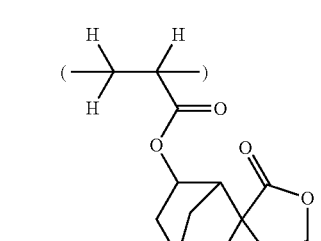
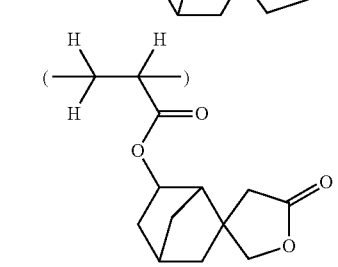
132
-continued
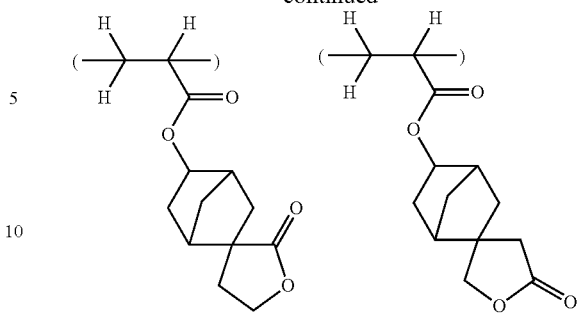
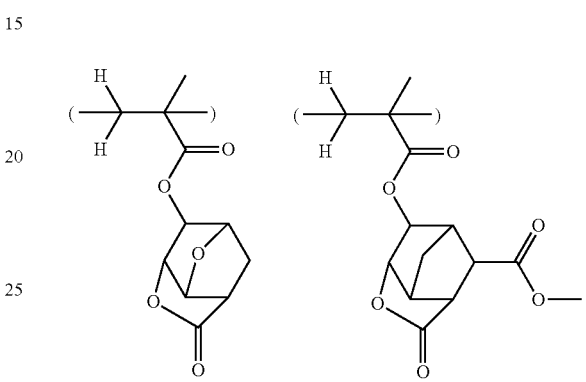
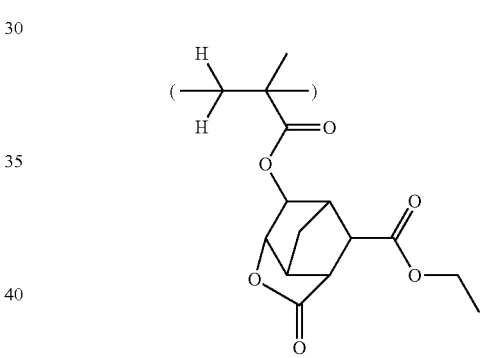
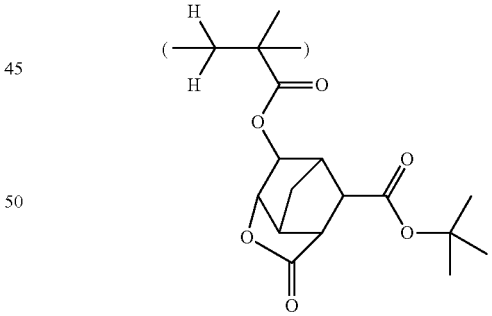
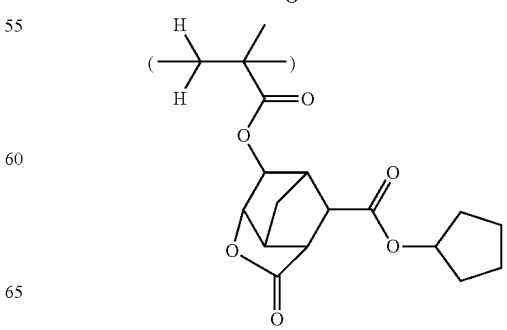

133
-continued
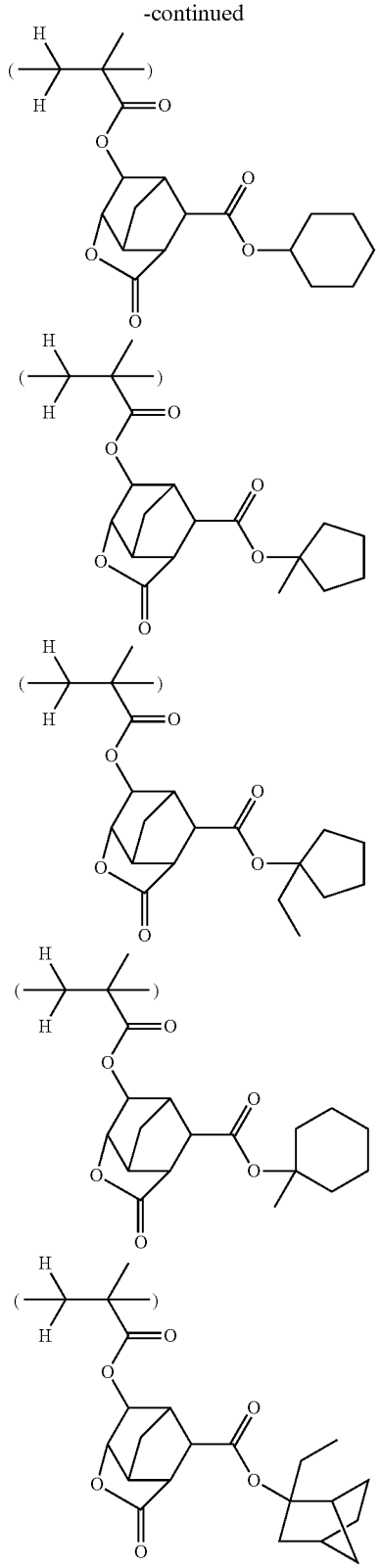
134
-continued
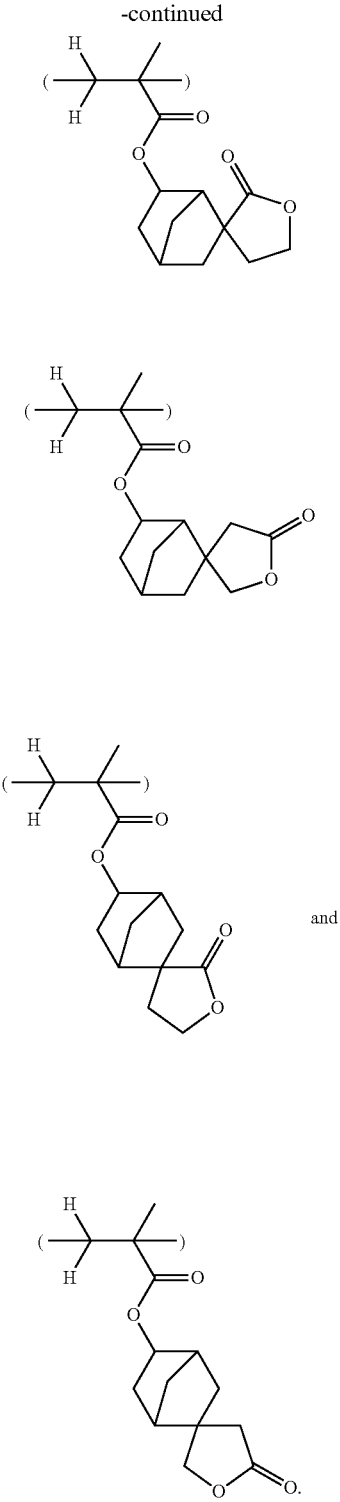
and
* * * * *